(12) United States Patent  (10) Patent No.: US 7,186,870 B2
Singer et al.  (45) Date of Patent: *Mar. 6, 2007

(54) PROCESS FOR THE PREPARATION OF 1,3-SUBSTITUTED INDENES AND ARYL-FUSED AZAPOLYCYCLIC COMPOUNDS

(75) Inventors: Robert A. Singer, Niantic, CT (US); Jason D. Mckinley, Amston, CT (US)

(73) Assignee: Pfizer Inc, New York, NY (US)

( * ) Notice: Subject to any disclaimer, the term of this patent is extended or adjusted under 35 U.S.C. 154(b) by 51 days.

This patent is subject to a terminal disclaimer.

(21) Appl. No.: 11/286,055

(22) Filed: Nov. 23, 2005

(65) Prior Publication Data

US 2006/0079707 A1  Apr. 13, 2006

Related U.S. Application Data

(63) Continuation of application No. 10/124,135, filed on Apr. 17, 2002.

(60) Provisional application No. 60/285,131, filed on Apr. 20, 2001.

(51) Int. Cl.
C07C 321/00 (2006.01)
C07C 323/00 (2006.01)
C07C 381/00 (2006.01)

(52) U.S. Cl. ............... 585/27; 585/269; 585/419; 558/303; 558/311; 560/18; 560/155

(58) Field of Classification Search .......... 585/27, 585/269, 419; 558/303, 311; 560/18, 155
See application file for complete search history.

(56) References Cited

U.S. PATENT DOCUMENTS

| | | | | |
|---|---|---|---|---|
| 6,410,550 | B1 * | 6/2002 | Coe et al. | 514/289 |
| 6,605,610 | B1 * | 8/2003 | Coe et al. | 514/250 |
| 6,699,909 | B1 * | 3/2004 | Curry | 514/567 |
| 2001/0036949 | A1 * | 11/2001 | Coe et al. | 514/299 |
| 2002/0010192 | A1 * | 1/2002 | Coe et al. | 514/300 |
| 2002/0016334 | A1 * | 2/2002 | Coe et al. | 514/303 |
| 2003/0109544 | A1 * | 6/2003 | Harrigan et al. | 514/303 |
| 2003/0130303 | A1 * | 7/2003 | Coe et al. | 514/300 |
| 2003/0133951 | A1 * | 7/2003 | Coe et al. | 424/239.1 |
| 2003/0176457 | A1 * | 9/2003 | Coe et al. | 514/302 |

FOREIGN PATENT DOCUMENTS

| | | | |
|---|---|---|---|
| WO | WO 00/45846 A1 * | 8/2000 |
| WO | WO00/45846 A1 * | 8/2000 |
| WO | W O 01/02340 A2 * | 1/2001 |
| WO | WO01/02340 A2 * | 1/2001 |

OTHER PUBLICATIONS

[R] Mazzochi et al., "Synthesis and Pharmacological Activity of 2,3,4,5-Tetrahydro-1,5-methano-1H-3-benzazepines," *Journal of Medicinal Chemistry*, 22(4), 455-457 (Apr. 1979).*

Mazzocchi et al., "Synthesis and Pharmacological Activity of 2,3,4,5-Tetrahydro-1,5-methano-1H-3-benzazepines," *Journal of Medicinal Chemistry*, 22(4), 455-457 (Apr. 1979).*

* cited by examiner

*Primary Examiner*—L. E. Crane
(74) *Attorney, Agent, or Firm*—Steve T. Zelson; A. David Joran

(57) ABSTRACT

The present invention relates to processes for the preparation of any of the intermediate 1,3-substituted indenes of the formulae (Ia), (Ib) and (Ic) or a mixture thereof:

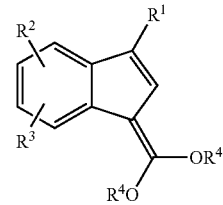

(Ia)

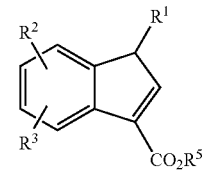

(Ib)

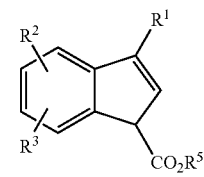

(Ic)

wherein $R^1$, $R^2$, $R^3$, $R^4$, and $R^5$ are defined herein. Compounds of formulae (Ia), (Ib) and (Ic) or mixtures thereof are useful in the preparation of compounds of formula (II):

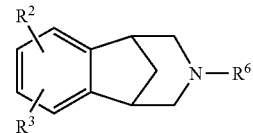

(II)

wherein $R^2$, $R^3$ and $R^6$ are also defined herein.

20 Claims, No Drawings

PROCESS FOR THE PREPARATION OF 1,3-SUBSTITUTED INDENES AND ARYL-FUSED AZAPOLYCYCLIC COMPOUNDS

This application is a continuation of 10/124,135, filed Apr. 17, 2002, now allowed, which claims the benefit under 37 C.F.R.119(e) of provisional application 60/285,131, filed Apr. 20, 2001, now expired.

The present invention relates to a process for the preparation of intermediate 1,3-substituted indenes of the formulae (Ia), (Ib) and (Ic) or mixtures thereof:

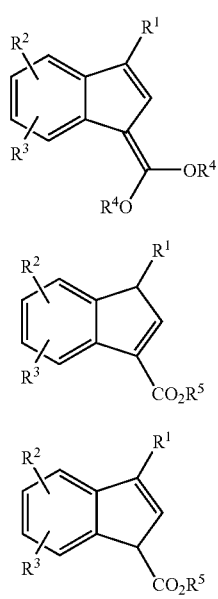

wherein $R^1$, $R^2$, $R^3$, $R^4$, and $R^5$ are defined below.

Compounds of formulae (Ia), (Ib) and (Ic) and mixtures thereof are useful in the preparation of compounds of formula (II):

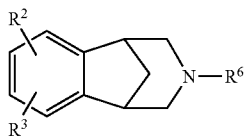

wherein $R^2$, $R^3$ and $R^6$ are also defined below. Processes for the preparation of compounds of formula (II) are set forth in WO 99/35131, corresponding to U.S. Ser. No. 09/402,010, filed Sep. 28, 1999 and U.S. Ser. No. 09/514,002, filed Feb. 25, 2000, both hereby incorporated by reference. The present invention offers a more efficient alternative pathway to the compounds of formula (II) via the use of a palladium-catalyzed cyclization process to prepare intermediate compounds of formulae (Ia), (Ib) and (Ic) which are then further converted to compounds of formula (II).

Compounds of formula (II) bind to neuronal nicotinic acetylcholine specific receptor sites and are useful in modulating cholinergic function. Such compounds are useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

The compounds of this invention may also be used in combination with an antidepressant such as, for example, a tricyclic antidepressant or a serotonin reuptake inhibiting antidepressant (SRI), in order to treat both the cognitive decline and depression associated with AD, PD, stroke, Huntington's chorea or traumatic brain injury (TBI); in combination with muscarinic agonists in order to stimulate both central muscarinic and nicotinic receptors for the treatment, for example, of ALS, cognitive dysfunction, age-related cognitive decline, AD, PD, stroke, Huntington's chorea and TBI; in combination with neurotrophic factors such as NGF in order to maximize cholinergic enhancement for the treatment, for example, of ALS, cognitive dysfunction, age-related cognitive decline, AD, PD stroke, Huntington's chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

SUMMARY OF THE INVENTION

The present invention relates to a process for the preparation of any one of the intermediate 1,3-substituted indenes of the formulae (Ia), (Ib) and (Ic) or mixtures thereof:

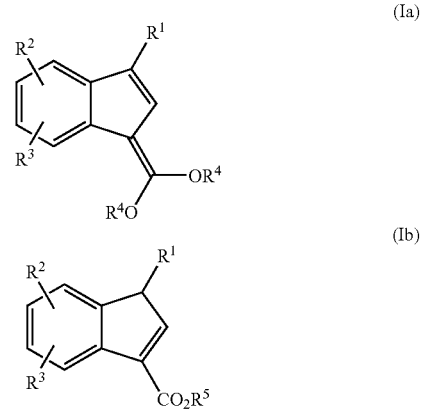

-continued

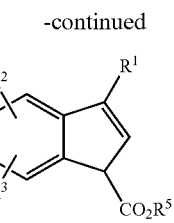
(Ic)

wherein $R^2$ and $R^3$ are selected, independently, from hydrogen, fluoro, chloro, —SO$_q$(C$_1$–C$_6$)alkyl wherein q is zero, one or two, ((C$_1$–C$_6$)alkyl)$_2$amino-, —CO$_2$R$^7$, —CONR$^8$R$^9$, —SO$_2$NR$^{10}$R$^{11}$, aryl-(C$_0$–C$_3$)alkyl- or aryl-(C$_0$–C$_3$)alkyl-O—, wherein said aryl is selected from phenyl and naphthyl, heteroaryl-(C$_0$–C$_3$)alkyl- or heteroaryl-(C$_0$–C$_3$)alkyl-O—, wherein said heteroaryl is selected from five to seven membered aromatic rings containing from one to four heteroatoms selected from oxygen, nitrogen and sulfur; $X^2$(C$_0$–C$_6$)alkyl- and $X^2$(C$_1$–C$_6$)alkoxy-(C$_0$–C$_6$)alkyl-, wherein $X^2$ is absent or $X^2$ is (C$_1$–C$_6$)alkylamino- or ((C$_1$–C$_6$)alkyl)$_2$amino-, and wherein the (C$_0$–C$_6$)alkyl- or (C$_1$–C$_6$)alkoxy-(C$_0$–C$_6$)alkyl- moieties of said $X^2$(C$_0$–C$_6$) alkyl- or $X^2$(C$_1$–C$_6$)alkoxy-(C$_0$–C$_6$)alkyl- contains at least one carbon atom, and wherein from one to three of the carbon atoms of said (C$_0$–C$_6$)alkyl- or (C$_1$–C$_6$)alkoxy-(C$_0$–C$_6$)alkyl-moieties may optionally be replaced by an oxygen, nitrogen or sulfur atom, with the proviso that any two such heteroatoms must be separated by at least two carbon atoms, and wherein any of the alkyl moieties of said (C$_0$–C$_6$)alkyl- or (C$_1$–C$_6$)alkoxy-(C$_0$–C$_6$)alkyl- groups may be optionally substituted with from two to seven fluorine atoms, and wherein one of the carbon atoms of each of the alkyl moieties of said aryl-(C$_0$–C$_3$)alkyl- and said heteroaryl-(C$_0$–C$_3$)alkyl- may optionally be replaced by an oxygen, nitrogen or sulfur atom, and wherein each of the foregoing aryl and heteroaryl groups may optionally be substituted with one or more substituents, preferably from zero to two substituents, independently selected from (C$_1$–C$_6$)alkyl optionally substituted with from one to seven fluorine atoms, (C$_1$–C$_6$)alkoxy optionally substituted with from two to seven fluorine atoms, chloro, fluoro, ((C$_1$–C$_6$)alkyl)$_2$amino-, —CO$_2$R$^7$, —CONR$^8$R$^9$, and —SO$_2$NR$^{10}$R$^{11}$;

or $R^2$ and $R^3$, together with the carbons to which they are attached, form a four to seven membered monocyclic, or a ten to fourteen membered bicyclic, carbocyclic ring that can be saturated or unsaturated, wherein from one to three of the non-fused carbon atoms of said monocyclic rings, and from one to five of the carbon atoms of said bicyclic rings that are not part of the benzo ring shown in formula (II), may optionally and independently be replaced by a nitrogen, oxygen or sulfur, and wherein said monocyclic and bicyclic rings may optionally be substituted with one or more substituents, preferably from zero to two substituents for the monocyclic rings and from zero to three substituents for the bicyclic rings, that are selected, independently, from (C$_0$–C$_6$)alkyl- or (C$_1$–C$_6$)alkoxy-(C$_0$–C$_6$)alkyl-, wherein the total number of carbon atoms does not exceed six and wherein any of the alkyl moieties may optionally be substituted with from one to seven fluorine atoms; oxo, fluoro, chloro, ((C$_1$–C$_6$)alkyl)$_2$amino-, —CO$_2$R$^7$, —CONR$^8$R$^9$, and —SO$_2$NR$^{10}$R$^{11}$;

each $R^7$, $R^8$, $R^9$, $R^{10}$, and $R^{11}$ is selected, independently, from hydrogen and (C$_1$–C$_6$)alkyl, or $R^8$ and $R^9$, or $R^{10}$ and $R^{11}$ together with the nitrogen to which they are attached, form a pyrrolidine, piperidine, morpholine, azetidine, piperazine, —N—(C$_1$–C$_6$)alkylpiperazine or thiomorpholine ring, or a thiomorpholine ring wherein the ring sulfur is replaced with a sulfoxide or sulfone; and each X is, independently, (C$_1$–C$_6$)alkylene;

$R^5$ is C$_1$–C$_6$ alkyl or Si(R$^{12}$)$_3$ $R^1$ is an electron withdrawing group selected from cyano, alkoxycarbonyl, alkylcarbonyl, arylcarbonyl, aryl, nitro, trifluoromethyl, and sulfonyl;

each $R^4$ is independently H, C$_1$–C$_6$, H(L)$_3$N$^+$, or a metal cation, including alkali metal cations of Na, K, Li, or Cs; or two $R^4$ groups together form a C$_2$–C$_3$ alkylene bridge;

each L is independently H, C$_1$–C$_6$ alkyl, phenyl or benzyl; and each $R^{12}$ is independently C$_1$–C$_6$ alkyl or phenyl;

comprising the step of reacting a compound of formula (III)

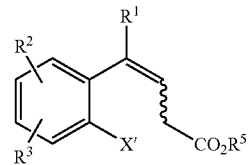
(III)

wherein $R^1$, $R^2$, $R^3$, and $R^5$ are as set forth above; and X' is iodo, bromo, chloro or OSO$_2$R$^{13}$, wherein $R^{13}$ is (C$_1$–C$_6$) alkyl, Si((C$_1$–C$_6$)alkyl)$_3$ or Si(phenyl)$_3$, in the presence of a palladium(0) catalyst and a base.

A preferred embodiment for this process of making indenes is wherein the palladium catalyst is formed from the combination of a palladium compound selected from the group consisting of palladium(II) acetate, palladium(II) chloride, bis-acetonitrile palladium(II) chloride, bis-benzonitrile palladium(II) chloride, palladium(II) bromide, tris (dibenzylideneacetone)dipalladium(0); more preferably selected from palladium(II) acetate; and a phosphine ligand selected from dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)-biphenyl, or 2-dicyclohexylphosphino-2'-(N,N-dimethylamino)biphenyl; more preferably tricyclohexylphosphine or tri-t-butylphosphine. A further preferred embodiment is wherein this step is conducted in the presence of a base selected from sodium tert-butoxide, potassium tert-butoxide, sodium tert-pentoxide, sodium ethoxide, sodium carbonate, potassium carbonate, cesium carbonate, sodium hydride, lithium hydride and potassium hydride; more preferably selected from sodium tert-butoxide and sodium tert-pentoxide. Further, a preferred aspect of the invention is wherein the aforesaid process is conducted in a solvent selected from 1,2-dimethoxyethane, tetrahydrofuran, 2-methyltetrahydrofuran, 1,2-diethoxyethane, 1,4-dioxane, toluene, N-methyl-pyrrolidinone, dimethylacetamide and dimethylformamide; more preferably selected from 1,2-dimethoxyethane and tetrahydrofuran. Further, preferably the aforesaid process step carried out at a temperature between room temperature and 120° C.; more preferably between 40 and 90° C., for a time period of 1 to 48 hours; more preferably for 8 hours.

Another embodiment of the process of the for the preparation of any one of the intermediates of formulae (Ia), (Ib)

and (Ic) and mixtures thereof is that process immediately above further comprising the prior step of reacting a compound of formula (IV):

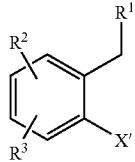
(IV)

wherein X' is iodo, bromo, chloro or $OSO_2R^{13}$, wherein $R^{13}$ is $(C_1-C_6)$alkyl, $Si((C_1-C_6)alkyl)_3$ or $Si(phenyl)_3$, with a compound of formula (V):

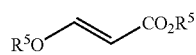
(V)

wherein $R^5$ is defined above; in the presence of a base.

A preferred embodiment for this condensation step is wherein this step is carried out in a solvent selected from tetrahydrofuran, 2-methyltetrahydrofuran, 1,2-dimethoxyethane, 1,2-diethoxyethane, 1,4-dioxane, dimethylsulfoxide, dimethylformamide, dimethylacetamide, N-methylpyrrolidinone, methylene chloride, 1,2-dichloromethane, methanol, ethanol, isopropanol, and propanol; more preferably, the solvent is selected from tetrahydrofuran, 2-methyltetrahydrofuran, and 1,2-dimethoxyethane. Another preferred embodiment of the invention is wherein the base in this step is selected from sodium tert-butoxide, potassium tert-butoxide, sodium methoxide, sodium ethoxide, sodium tert-pentoxide, sodium carbonate, potassium carbonate, cesium carbonate, lithium diisopropylamide, lithium bis(trimethylsilyl)amide, sodium bis(trimethylsilyl)amide, potassium bis(trimethylsilyl)amide, sodium hydride, and lithium hydride; more preferably, the base is selected from sodium tert-butoxide, sodium ethoxide and sodium methoxide. Further, a preferred process is wherein this step is carried out at a temperature between −78° C. and 50° C., more preferably between 0° C. and 30° C., preferably for a period of 1 to 24 hours, more preferably for 6 hours.

A more preferred embodiment is wherein the process for the preparation of any one of the intermediates of formulae (Ia), (Ib) and (Ic) and mixtures thereof is a tandem condensation and palladium-catalyzed cyclization comprising the single step of reacting a compound of formula (IV)

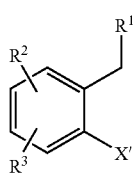
(IV)

wherein X' is iodo, bromo, chloro or $OSO_2R^{13}$, wherein $R^{13}$ is $(C_1-C_6)$alkyl, $Si((C_1-C_6)alkyl)_3$ or $Si(phenyl)_3$, with a compound of formula (V):

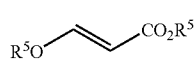
(V)

wherein $R^5$ is defined above; in the presence of a base and a palladium(0) catalyst.

Preferably the tandem condensation and palladium-catalyzed cyclization in a single step is conducted by first dissolving the compounds of formula (IV) and (V) in a solvent such as tetrahydrofuran, 2-methyltetrahydrofuran, 1,2-dimethoxyethane, 1,2-diethoxyethane, 1,4-dioxane, dimethylsulfoxide, dimethylformamide, dimethylacetamide, N-methylpyrrolidinone, methylene chloride, 1,2-dichloromethane, preferably tetrahydrofuran, 2-methyltetrahydrofuran, or 1,2-dimethoxyethane, and then adding the solution to a mixture containing both the base and the palladium(0) catalyst also in one of the above-mentioned solvents. Preferably the base is selected from the group consisting of sodium tert-butoxide, potassium tert-butoxide, sodium methoxide, sodium ethoxide, sodium tert-pentoxide, sodium carbonate, potassium carbonate, cesium carbonate, lithium diisopropylamide, lithium bis(trimethylsilyl)amide, sodium bis(trimethylsilyl)amide, potassium bis(trimethylsilyl)amide, sodium hydride and lithium hydride; more preferably, selected from sodium tert-butoxide, sodium ethoxide and sodium methoxide. Preferably the palladium catalyst is prepared by the combination of a palladium compound selected from palladium(II) acetate, palladium(II) chloride, bis-acetonitrile palladium(II) chloride, bis-benzonitrile palladium(II) chloride, palladium(II) bromide, tris(dibenzylideneacetone)dipalladium(0); more preferably palladium(II) acetate; and a phosphine ligand such as dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)biphenyl, or 2-dicyclohexylphosphino-2'-(N,N-dimethylamino)biphenyl; more preferably tricyclohexylphosphine or tri-t-butylphosphine. Preferably, this single step formation of indenes is performed at a temperature between −78° C. and 50° C.; more preferably between 0° C. and 30° C., for a period of 1 to 24 hours, more preferably for 1 to 5 hours, and then is heated between 25° C. and 120° C.; more preferably between 40° C. and 90° C. for a period of 1 to 24 hours, preferably 8 hours.

A preferred embodiment of the invention relate to processes for the preparation of compounds of any one of the formulae (Ia), (Ib) and (Ic) and mixtures thereof wherein one or both of $R^2$ and $R^3$ is H, $(C_1-C_6)$alkoxy, $CF_3$, fluoro or $C_2F_5$ and $R^1$ is CN. A more preferred embodiment is where $R^2$ and $R^3$ is H; $R^1$ is CN; and X' is Br. Preferably, $R^5$ in the compound of formula (V) is methyl or ethyl.

The present invention also relates to the 1,3-substituted indene compounds of the formulae (Ia), (Ib) and (Ic). Preferred indene compounds of the invention include:

3-(Hydroxy-methoxy-methylene)-5-trifluoromethyl-3H-indene-1-carbonitrile, sodium salt;

3-(Hydroxy-methoxy-methylene)-3H-indene-1-carbonitrile, sodium salt;

3-(Ethoxy-hydroxy-methylene)-3H-indene-1-carbonitrile, sodium salt;

3-(Ethoxy-hydroxy-methylene)-5,6-dimethoxy-3H-indene-1-carbonitrile, sodium salt;

3-(Hydroxy-ethoxy-methylene)-5-trifluoromethyl-3H-indene-1-carbonitrile, sodium salt;

3-(Ethoxy-hydroxy-methylene)-7-fluoro-3H-indene-1-carbonitrile, sodium salt;

3-(Ethoxy-hydroxy-methylene)-5-fluoro-3H-indene-1-carbonitrile, sodium salt;

3-[1,3]Dioxolan-2-ylidene-5-trifluoromethyl-3H-indene-1-carbonitrile;

3-[1,3]Dioxolan-2-ylidene-3H-indene-1-carbonitrile; and

3-Benzenesulfonyl-3H-indene-1-carboxylic acid ethyl ester.

The present invention is also directed to the preparation of compounds of formula (VII):

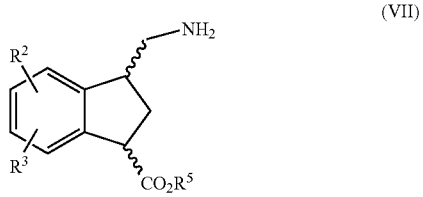

(VII)

wherein $R^2$, $R^3$, and $R^5$ are as defined above; comprising the process as indicated above to prepare compounds of any one of the formulae (Ia), (Ib) and (Ic) where $R^1$ is CN, and mixtures thereof; and further comprising the step of (A) subjecting any one of the compounds of the formulae (Ia)', (Ib)', and (Ic)' or a mixture thereof:

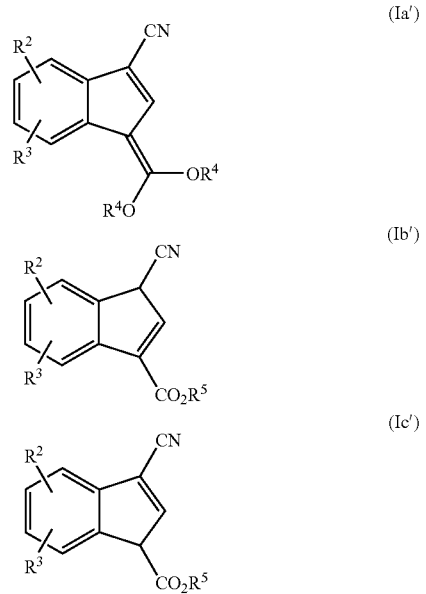

(Ia')

(Ib')

(Ic')

or mixtures thereof to hydrogenolysis conditions.

A preferred embodiment of the invention is wherein the hydrogenation conditions of step (A) are preferably those suitable for effectuating the desired reduction, wherein the hydrogenation catalyst and conditions would be known to one of ordinary skill in the art as reflected in a reference such as Comprehensive Organic Synthesis, Vol. 8, "Reduction," Eds.-in-Chief, B. M. Trost and Ian Fleming (Pergamon Press NY 1991). Nonetheless, a preferred embodiment of the invention is wherein the hydrogenolysis of step (A) is carried out using a hydrogenation catalyst selected from palladium on carbon, palladium hydroxide on carbon, platinum on carbon, platinum oxide, and platinum oxide on carbon; more preferably selected from 5% palladium on carbon, 10% palladium on carbon and 5% platinum on carbon; in the presence of an acid selected from sulfuric acid, hydrochloric acid, methane sulfonic acid, toluenesulfonic acid, trifluoroacetic acid, acetic acid, formic acid, phosphoric acid and perchloric acid, more preferably selected from sulfuric acid, methane sulfonic acid, and a mixture of any of the acids listed above. Preferably, the solvent for the hydrogenolysis is selected from methanol, ethanol, isopropanol, butanol, propanol, ethyl acetate, isopropyl acetate, tetrahydrofuran, toluene, ethylene glycol and a mixture of any of these solvents; more preferably the solvent is selected from ethyl acetate, methanol, ethanol and propanol. The hydrogenolysis step (A) is preferably conducted under a hydrogen atmosphere up to 7 atmospheres (approximately 100 psi), more preferably 3 to 4 atmospheres (approximately 50 psi); preferably for a time period of 1 to 24 hours; more preferably 6 hours. Further, step (iii) is preferably carried out at a temperature between 0 and 60° C.; more preferably between 20 and 40° C.

The present invention also relates to a process for the preparation of a compound of formula (VII), as defined above, wherein step (A) is replaced by the two separate steps of (a) subjecting any one of the compounds of the formulae (Ia)', (Ib)' and (Ic)' or mixtures thereof to hydrogenolysis conditions to obtain a compound of formula (IX):

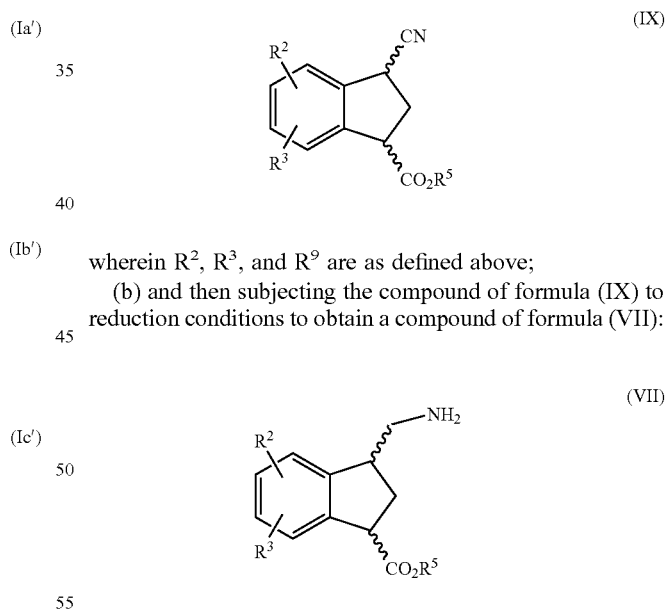

(IX)

wherein $R^2$, $R^3$, and $R^9$ are as defined above;

(b) and then subjecting the compound of formula (IX) to reduction conditions to obtain a compound of formula (VII):

(VII)

wherein $R^2$, $R^3$, and $R^9$ are as defined above.

The hydrogenation conditions of either of steps (a) and (b) are preferably those suitable for effectuating the desired reduction, wherein the hydrogenation catalysts and conditions would be known to one of ordinary skill in the art as reflected in a reference such as Comprehensive Organic Synthesis, Vol. 8, "Reduction," Eds.-in-Chief, B. M. Trost and Ian Fleming (Pergamon Press NY 1991). However, a preferred embodiment of the invention is wherein the hydrogenolysis conditions in step (a) for the reduction of any of the compounds of formulae (Ia)', (Ib)' and (Ic)' or mixtures thereof to one of formula (IX) comprises treatment with a hydrogenation catalyst selected from the group consisting of palladium on carbon, palladium hydroxide on carbon, platinum on carbon, platinum oxide, platinum oxide on carbon; more preferably selected from 5% palladium on carbon, 10% palladium on carbon and 5% platinum on carbon; optionally in the presence of an acid such as acetic acid, formic acid, benzoic acid, or salicylic acid; more preferably, formic acid or acetic acid; in a solvent such as methanol, ethanol, isopropanol, butanol, propanol, ethyl acetate, isopropyl acetate, tetrahydrofuran, toluene, or any mixture of these solvents; more preferably methanol or ethanol; under a hydrogen atmosphere up to 7 atmospheres (approximately 100 psi), more preferably 3 to 4 atmospheres (approximately 50 psi), for a time period of 1 to 48 hours preferably 12 hours. Further, this step is preferably carried out at a temperature between 0 and 60° C.; more preferably between 20 and 30° C.

A further preferred embodiment of the invention is wherein the reduction conditions in step (b) for reducing the nitrile compound of formula (IX) to one of formula (VII) comprises treatment with a hydrogenation catalyst selected from the group consisting of palladium on carbon, palladium hydroxide on carbon, platinum on carbon, platinum oxide, platinum oxide on carbon; more preferably selected from 5% palladium on carbon, 10% palladium on carbon, and 5% platinum on carbon; in the presence of an acid such as sulfuric acid, hydrochloric acid, methane sulfonic acid, toluenesulfonic acid, trifluoroacetic acid, acetic acid, formic acid, phosphoric acid or perchloric acid, preferably sulfuric acid, methane sulfonic acid, or any combination of the acids listed above; in a solvent such as methanol, ethanol, isopropanol, butanol, propanol, ethyl acetate, isopropyl acetate, tetrahydrofuran, toluene, or any mixture of these solvents; preferably methanol or ethanol; under a hydrogen atmosphere up to up to 7 atmospheres (approximately 100 psi), more preferably 3 to 4 atmospheres (approximately 50 psi); for a time period of 1 to 48 hours preferably 6 hours. Further, this step is preferably carried out at a temperature between 0 and 60° C.; more preferably between 20 and 40° C.

The present invention also relates to compounds of formula (IX):

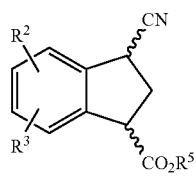

(IX)

wherein $R^2$, $R^3$, and $R^9$ are as defined above. Particularly preferred compounds of formula (IX) are:

3-Cyano-indan-1-carboxylic acid, ethyl ester;
6-Trifluoromethyl-3-cyano-indan-1-carboxylic acid, ethyl ester;
5,6-Dimethoxy 3-cyano-indan-1-carboxylic acid, ethyl ester;
4-Fluoro-3-cyano-indan-1-carboxylic acid, ethyl ester;
6-Fluoro-3-cyano-indan-1-carboxylic acid, ethyl ester; and
3-Benzenesulfonyl-3-Cyano-indan-1-carboxylic acid, ethyl ester.

The present invention also relates to a process for the preparation of a compound of formula (VIII):

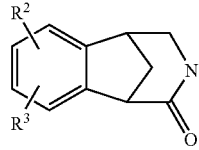

(VIII)

comprising the aforementioned steps relating to the preparation of compounds of formula (VII) immediately above; further comprising the step of (B) subjecting a compound of formula (VII) to basic conditions to effect an amide cyclization.

A preferred process of the invention is wherein the basic conditions of the step (B) consist of treatment with a base selected from the group consisting of sodium tert-butoxide, sodium methoxide, sodium ethoxide, sodium hydroxide, potassium tert-butoxide, potassium methoxide, potassium ethoxide, potassium hydroxide, sodium carbonate, potassium carbonate, cesium carbonate, sodium hydride, triethylamine, methylimidazole, lutidine, pyridine, methylmorpholine, ethylmorpholine, or diisopropylethylamine; more preferably is sodium tert-butoxide or sodium methoxide; in a solvent selected from the group consisting of methanol, ethanol, isopropanol, propanol, butanol, ethylene glycol, ethyl acetate, acetonitrile, toluene, water, and a mixture of any of these solvents; more preferably, the solvent is methanol, ethanol, propanol or any mixture of methanol, ethanol or propanol. Preferably, step (iv) is conducted at a temperature between 0 and 120° C., more preferably at room temperature, preferably for a time period between 30 minutes and 72 hours, more preferably 6 to 12 hours.

The present invention is also directed to the preparation of compounds of formula (II):

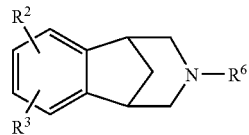

(II)

wherein $R^6$ is hydrogen; and $R^2$ and $R^3$ are as defined above; comprising the aforementioned steps relating to the preparation of compounds of formula (VIII); further comprising the step of (C) reducing the carbonyl group of the compound of formula (VIII) with a reducing agent to obtain a compound of formula (II).

A preferred embodiment of the invention is wherein the reducing step (C) is conducted with a reducing agent selected from the group consisting of borane tetrahydrofuran complex, diborane, borane dimethylsulfide complex, lithium aluminum hydride, and a combination of sodium borohydride and boron trifluoride; more preferably the reducing agent is either borane tetrahydrofuran complex or a combination of sodium borohydride and boron trifluoride. Preferably, the reducing step is conducted in a solvent selected from the group consisting of tetrahydrofuran, 1,2-dimethoxyethane, 1,2-diethoxyethane, 2-methyltetrahydrofuran, 1,4-dioxane and methyl-tert-butyl ether; more preferably, the solvent is tetrahydrofuran. Preferably, the reduction is conducted at a temperature between 0 and 80°

C.; more preferably, 50° C.; for a time period of between 1 and 24 hours; preferably 5 hours.

In a preferred embodiment of the invention, the product of formula (II) may then be isolated by removal of the solvent. More preferably, the product is isolated by crystallization as a salt, most preferably as the salt of an acid such as tosic acid, methane sulfonic acid, hydrochloric acid, oxalic acid, citric acid or acetic acid; more preferably tosic acid is used, in a solvent such as isopropanol, hexane, acetone, ethyl acetate, methyl ethyl ketone or toluene, more preferably isopropanol or ethyl acetate.

The present invention further relates to a process for the preparation of a compound of formula (II), as set forth above, wherein $R^6$ is $R^{6'}$ and $R^{6'}$ is $(C_1-C_6)$alkyl, unconjugated $(C_3-C_6)$alkenyl, benzyl, $-(C_1-C_6)$alkyl-CHO, $-(C_1-C_6)$alkyl-(C=O)-(C_1-C_6)$alkyl or $-CH_2CH_2O-(C_1-C_4)$alkyl; comprising steps as set forth above for preparing a compound of formula (II) where $R^6$ is H; further comprising the step (D) of reacting the product of step (v) with a compound of formula $R^{6'}$—Y wherein Y is a leaving group such as chloro, bromo, iodo or mesylate.

The present invention also relates to a process for the preparation of a compound of formula (II), as set forth above, wherein $R^6$ is $(CH_2)$—$R^{6''}$ and $R^{6''}$ is $(C_1-C_5)$alkyl, unconjugated $(C_3-C_5)$alkenyl, phenyl, $-(C_1-C_5)$alkyl-CHO, $-(C_1-C_5)$alkyl-(C=O)-(C_1-C_6)$alkyl or $-CH_2-O-(C_1-C_4)$alkyl comprising the step of reacting under reductive amination conditions a compound of formula (II) (where $R^6$ is H) with a compound of formula $R^{6''}$—CHO. Preferably, the reductive amination conditions of this process are either catalytic hydrogenation or treatment with several hydride reagents in a reaction-inert solvent. More preferably, the catalytic hydrogenation is carried out in the presence of a metal catalyst such as palladium or Raney nickel. Most preferably, the reductive amination condition are treatment with a hydride reagent selected from borohydrides such as sodium borohydride ($NaBH_4$), sodium cyanoborohydride ($NaBH_3CN$) and sodium triacetoxyborohydride ($NaB(OAc)_3H$), boranes, aluminum-based reagents and trialkylsilanes in a suitable solvent selected from a polar solvent such as methanol, ethanol, methylene chloride, tetrahydrofuran (THF), dioxane and ethyl acetate. Preferably, this reductive amination is carried out at a temperature from −78° C. to reflux temperature of the solvent, more preferably from 0° C. to 25° C. for 5 minutes to 48 hours, most preferably from 0.5 to 12 hours.

Examples of preferred heteroaryl groups within the definition of $R^2$ and $R^3$ are the following: thienyl, oxazoyl, isoxazolyl, pyridyl, pyrimidyl, thiazolyl, tetrazolyl, isothiazolyl, triazolyl, imidazolyl, tetrazolyl, pyrrolyl and the following groups:

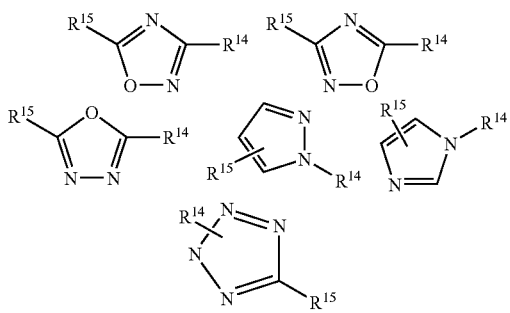

wherein one of $R^{14}$ and $R^{15}$ is hydrogen or $(C_1-C_6)$alkyl, and the other is a bond to the benzo ring of formula (II).

Examples of the bicyclic ring systems that $R^2$ and $R^3$, together with the benzo ring of formula (II), can form may be selected from the following:

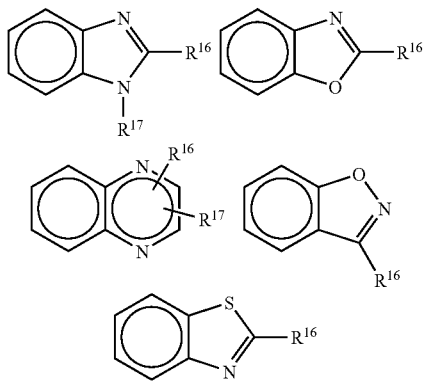

wherein $R^{16}$ and $R^{17}$ are selected, independently, from H, $(C_1-C_6)$alkyl-, $(C_1-C_6)$alkoxy-$(C_0-C_6)$alkyl-, wherein the total number of carbon atoms does not exceed six and wherein any of the alkyl moieties may optionally be substituted with from one to seven fluorine atoms; oxo, fluoro, chloro, $((C_1-C_6)$alkyl)$_2$amino-, $-CO_2R^4$, $-CONR^5R^6$, and $-SO_2NR^7R^8$; wherein $R^4$, $R^5$, $R^6$, $R^7$ and $R^8$ are defined above.

Other embodiments of this invention relate to processes for the preparation of compounds of formula (II), and their pharmaceutically acceptable salts, wherein $R^2$ and $R^3$, together with the benzo ring of formula (II), form a bicyclic or tricyclic ring system selected from the following:

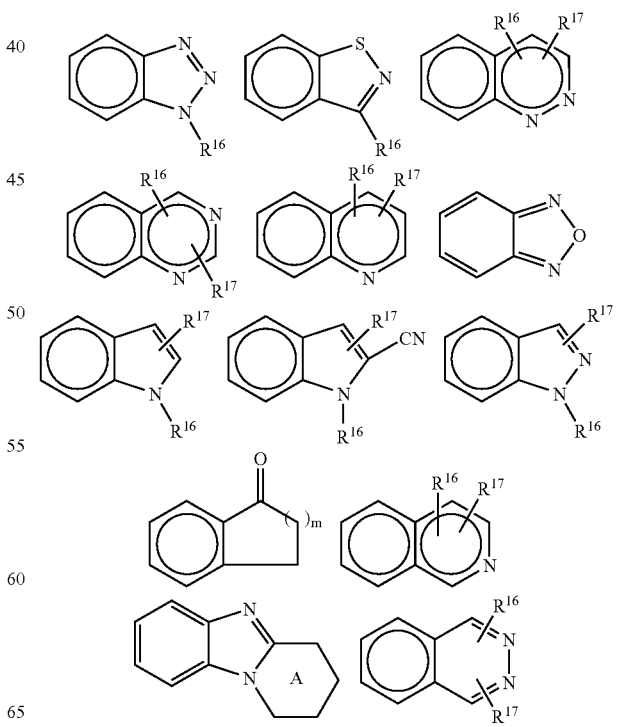

wherein $R^{16}$ and $R^{17}$ are defined as above, and m is zero, one or two, and wherein one of the carbon atoms of ring A can optionally be replaced with oxygen or $N(C_1-C_6)$alkyl.

Other preferred embodiments of this invention relate to processes for the preparation of compounds of the formula (II), and their pharmaceutically acceptable salts, wherein $R^2$ and $R^3$ do not, together with the benzo ring of formula (II), form a bicyclic or tricyclic ring system.

Other preferred embodiments of this invention relate to processes for the preparation of compounds of the formula (II) wherein one or both of $R^2$ and $R^3$ is $(C_1-C_6)$alkoxy, —$CF_3$, fluoro or $C_2F_5$.

Although the compounds of formula (II) may be made with the groups $R^2$ and $R^3$ already in place, in the alternative the compounds of formula (II) may be prepared from a compound of formula (II), where $R^2$ and $R^3$, are both H made by the processes of the present invention, further subjecting the compound of formula (II) wherein $R^2$, $R^3$ and $R^6$ are all H to processes as follows.

The present invention also relates to methods for the preparation of the compounds of formula (II) comprising the further steps of (i) placing a protecting group, Q, on the nitrogen of a compound of formula (II) where $R^2$, $R^3$ and $R^6$ are H:

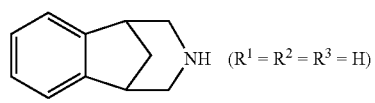

(II)

($R^1 = R^2 = R^3 = H$)

made in accordance with the process set forth above;

(ii) reacting the Q-group protected compound from step (i) with trifluoromethanesulfonic acid ($CF_3SO_2OH$) and equivalents of nitric acid to obtain a compound of formula (XIII-Q):

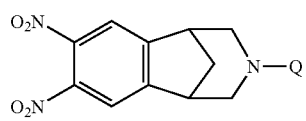

XIII-Q and (iii) reducing the nitro groups of the compound XIII-Q to obtain a compound of formula (XIV-Q):

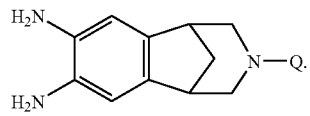

XIV-Q

The nitrogen protecting group Q may be chosen from suitable groups known to those of skill in the art including —$COCF_3$, —$COCCl_3$, —$COOCH_2CCl_3$, —$COO(C_1-C_6)$ alkyl and —$COOCH_2C_6H_5$. These groups may be added or removed by methods described for each in T. W. Greene and G. M. Wuts, *Protective Groups in Organic Synthesis* (John Wiley & Sons, New York, 1991). Preferably, the nitrogen protecting group Q is a trifluoroacetyl or a t-butoxycarbonyl group.

Preferably, step (ii) is carried out in a mixture of 4 or more equivalents of trifluoromethanesulfonic acid ($CF_3SO_2OH$) and 2 to 3 equivalents of nitric acid, in a chlorinated hydrocarbon solvent such as chloroform, dichloroethane (DCE) or methylene chloride. Preferably, the resulting mixture is allowed to react for about 5 to 24 hours, more preferably at a temperature ranging from about −78° C. to about 0° C. for about 2 hours, and then allowed to warm to room temperature for the remaining time. Preferably, step (iii) is accomplished using hydrogen gas and a palladium catalyst such as palladium hydroxide, 5% palladium on carbon or 10% palladium on carbon.

The invention is also directed to a process for the preparation of a compound of formula (IA):

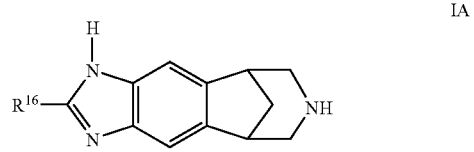

IA wherein $R^{16}$ is defined above, comprising the step of reacting a compound of formula (XIV-Q) made in accordance with the process set forth above:

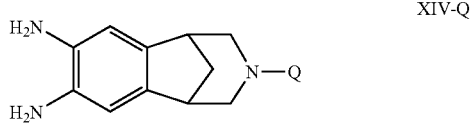

XIV-Q wherein Q is a nitrogen protecting group, with a compound of formula (XXVIII):

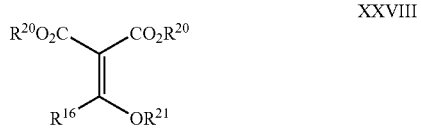

XXVIII wherein $R^{20}$ and $R^{21}$ are each independently $(C_1-C_6)$alkyl, and wherein $R^{16}$ is defined above; and (ii) removing the protecting group Q.

The nitrogen protecting group Q may be chosen from suitable groups known to those of skill in the art including —$COCF_3$, —$COCCl_3$, —$COOCH_2CCl_3$, —$COO(C_1-C_6)$ alkyl and —$COOCH_2C_6H_5$. These groups may be added or removed by methods described for each in T. W. Greene and G. M. Wuts, *Protective Groups in Organic Synthesis* (John Wiley & Sons, New York, 1991). Preferably, the nitrogen protecting group Q is a trifluoroacetyl or a t-butoxycarbonyl group.

The invention also relates to a process for the preparation of a compound of formula (IB):

[Structure IB: benzimidazole fused bicyclic amine with R$^{17}$ on N, R$^{16}$ on C, and NH]

IB wherein R$^{16}$ and R$^{17}$ are defined above, comprising the steps of (i) of reacting a compound of formula (XIV-Q) made in accordance with the process set forth above:

[Structure XIV-Q: diaminobenzene fused bicyclic amine, H$_2$N groups, N—Q]

XIV-Q wherein Q is a nitrogen protecting group, with a compound of formula (XXVIII):

[Structure XXVIII: R$^{20}$O$_2$C, CO$_2$R$^{20}$, R$^{16}$, OR$^{21}$ on alkene]

XXVIII wherein R$^{20}$ and R$^{21}$ are each independently (C$_1$–C$_6$)alkyl, and wherein R$^{16}$ is defined above; and (ii) allowing the product of step (i) to react with a compound of the formula R$^{17}$Z, wherein R$^{17}$ is defined above, and Z is a leaving group, in the presence of a base;

(iii) removing the protecting group Q.

Preferably, in this method to prepare IB the leaving group is selected from the group consisting of halo, halosulfonate, mesylate and tosylate, and the base is an alkali metal hydride, hydroxide or carbonate. Preferably, the protecting group Q is a trifluoroacetyl or a t-butoxycarbonyl group.

The invention also relates to another process for the preparation of a compound of formula (IB):

[Structure IB again]

IB wherein R$^{16}$ and R$^{17}$ are defined above, comprising the steps of (i) reacting a compound of formula (XIV-Q), made in accordance with the procedures set forth above, with one equivalent of a compound of the formula R$^{17}$Z, wherein R$^{17}$ is defined above, and Z is a leaving group, in the presence of a base to form a compound of formula (XX-Q):

[Structure XX-Q: R$^{17}$HN and H$_2$N on benzene ring fused to bicyclic amine, N—Q]

XX-Q wherein Q is a nitrogen protecting group, (ii) reacting the compound of formula XX-Q with a compound of formula (XXVIII):

[Structure XXVIII]

XXVIII wherein R$^{20}$ and R$^{21}$ are each independently (C$_1$–C$_6$)alkyl, and wherein R$^{16}$ is defined above; and (iii) removing the protecting group Q.

Preferably, in this method to prepare IB, the protecting group Q is a trifluoroacetyl or a t-butoxycarbonyl group.

The invention is also directed to a process for preparing a compound of formula (IC)

[Structure IC: quinoxaline fused bicyclic amine with R$^{16}$, R$^{17}$ and NH]

IC wherein R$^{16}$ and R$^{17}$ are as defined above, comprising the steps of (i) allowing a compound of formula (XIV-Q) made in accordance with the procedures set forth above:

[Structure XIV-Q]

XIV-Q wherein Q is a nitrogen protecting group, to react with a compound of formula

[Structure: YO$_3$S–CH(OH)–CH(OH)–SO$_3$Y]

wherein Y is an alkali metal or alkaline earth metal cation; or a compound of formula

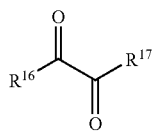

wherein $R^{16}$ and $R^{17}$ are as defined above; and (ii) removing the protecting group Q.

The protecting group Q is preferably a trifluoroacetate group or a t-butoxycarbonyl group. A preferred process of the invention is wherein step (i) is conducted with a compound of formula

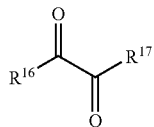

wherein $R^{16}$ and $R^{17}$ are both H. Preferably, step (i) is conducted in a polar solvent, more preferably, water, THF, DMF, DMSO, a mixture of water and any of THF, DMF or DMSO.

Unless otherwise indicated, the term "halo", as used herein, includes fluoro, chloro, bromo and iodo.

Unless otherwise indicated, the term "alkyl", as used herein, includes straight chain moieties, and where the number of carbon atoms suffices, branched and cyclic moieties.

The term "alkoxy", as used herein, means "—O-alkyl" or "alkyl-O—", wherein "alkyl" is defined as above.

The term "alkylene, as used herein, means an alkyl radical having two available bonding sites (i.e., -alkyl-), wherein "alkyl" is defined as above.

Unless otherwise indicated, the term "one or more substituents", as used herein, refers to from one to the maximum number of substituents possible based on the number of available bonding sites.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula (II) as prepared according to the invention may have optical centers and therefore may occur in different enantiomeric configurations. The invention includes all enantiomers, diastereomers, and other stereoisomers of such compounds of formula (II), as well as racemic mixtures thereof. The present invention also relates to all radiolabeled forms of the compounds of the formula (II) prepared by the methods of the invention. Preferred radiolabeled compounds of formula (II) are those wherein the radiolabels are selected from as $^{3}H$, $^{11}C$, $^{14}C$, $^{18}F$, $^{123}I$ and $^{125}I$. Such radiolabeled compounds are useful as research and diagnostic tools in metabolism studies, such as pharmacokinetics studies, etc., and in binding assays in both animals and man.

This invention also relates processes for generating pharmaceutically acceptable acid addition salts of the compounds of formula (II) using the processes of the invention. Examples of pharmaceutically acceptable acid addition salts of the compounds of formula (II) are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malic acid, di-p-toluoyl tartaric acid, and mandelic acid, as well salts formed from other acids known to those of skill in the art to form pharmaceutically acceptable acid addition salts to basic compounds. Other possible acid addition salts are, e.g., salts containing pharmaceutically acceptable anions, such as the hydroiodide, nitrate, sulfate or bisulfate, phosphate or acid phosphate, acetate, lactate, gluconate, saccharate, benzoate, methanesulfonate, ethanesulfonate, benzenesulfonate, and pamoate (i.e., 1.1'-methylene-bis-(2-hydroxy-3-naphthoate) salts).

This invention is also directed to processes of the invention for making isotopically-labeled compounds identical to those recited in formula (II), or pharmaceutically acceptable salts thereof, but for the fact that one or more atoms are replaced therein by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The invention is also directed to methods of preparing compounds of the present invention, prodrugs thereof, and pharmaceutically acceptable salts of said compounds, or of said prodrugs, which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful, for example, in drug and/or substrate tissue distribution assays. Tritiated, i.e., $^{3}H$, and carbon-14, i.e., $^{14}C$, isotopes are particularly preferred for their ease of preparation and detectability. Furthermore, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formulae I of this invention and prodrugs thereof can generally be prepared by carrying out the procedures set forth herein, by substituting a readily available isotopically labeled reagent for a non-isotopically labeled reagent.

DETAILED DESCRIPTION OF THE INVENTION

Compounds of formula (Ia), (Ib) and (Ic) or mixtures thereof may be prepared in accordance with the novel method shown in reaction Scheme 1. Scheme 2 provides an additional alternative route to obtain these compounds. Compounds of formulae (VII), (VIII), (II), (II') and (II") may be prepared according to Schemes 3 and 4. Unless otherwise indicated, the variables $R^1$, $R^2$, $R^3$, $R^4$, $R^5$, $R^6$, $R^{6'}$, $R^{6''}$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{20}$, X, X', L, Q and Z are as described above.

Scheme 1

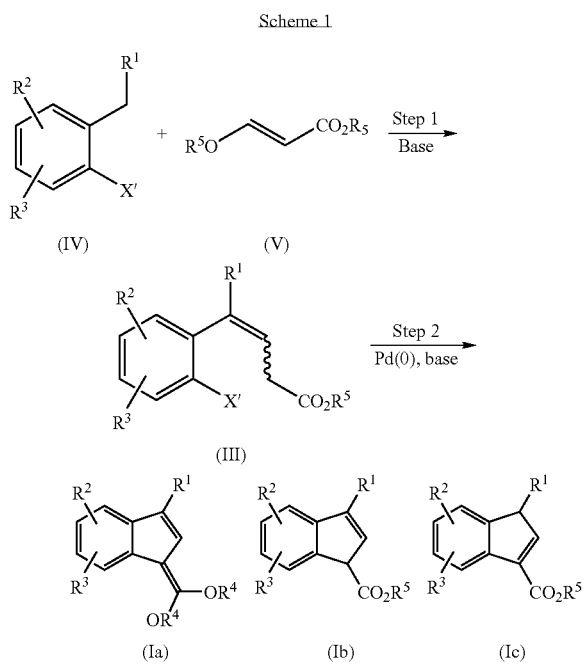

The present invention provides a new means to obtain the skeletal framework of compounds of formula (Ia), (Ib) and (Ic) via the condensation of an aryl derivative with an alkoxyacrylate to afford an intermediate for cyclization in tandem or in separate steps. A palladium catalyst effects cyclization to the corresponding indene derivatives of formulae (Ia), (Ib) and (Ic) or mixtures thereof. Scheme 1 depicts the general process of the invention for the preparation of indenes.

Step 1 of Scheme 1 is a condensation reaction. An aryl derivative of formula (IV) is combined with an alkoxyacrylate of formula (V) in a solvent such as tetrahydrofuran, 2-methyltetrahydrofuran, 1,2-dimethoxyethane, 1,2-diethoxyethane, 1,4-dioxane, dimethylsulfoxide, dimethylformamide, dimethylacetamide, N-methylpyrrolidinone, methylene chloride, 1,2-dichloromethane, methanol, ethanol, isopropanol, or propanol, preferably tetrahydrofuran, 2-methyltetrahydrofuran, or 1,2-dimethoxyethane, and is added to base such as sodium tert-butoxide, potassium tert-butoxide, sodium methoxide, sodium ethoxide, sodium tert-pentoxide, sodium carbonate, potassium carbonate, cesium carbonate, lithium diisopropylamide, lithium bis(trimethylsilyl) amide, sodium bis(trimethylsilyl)amide, potassium bis(trimethylsilyl)amide, sodium hydride, or lithium hydride, preferably sodium tert-butoxide or sodium methoxide, in one of the above mentioned solvents at a temperature between −78° C. and 50° C., preferably between 0° C. and 30° C., for a period of 1 to 24 hours, preferably 6 hours, to afford a compound of formula (III) which may be a mixture of olefin isomers.

Step 2 of Scheme 1 is a palladium-catalyzed cyclization reaction. A compound of formula (III) is treated with a palladium source such as palladium(II) acetate, palladium (II) chloride, bis-acetonitrile palladium(II) chloride, bis-benzonitrile palladium(II) chloride, palladium(II) bromide, tris(dibenzylideneacetone)dipalladium(0), preferably palladium(II) acetate, and a phosphine ligand such as dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)biphenyl, or 2-dicyclohexylphosphino-2'-(N,N-dimethylamino)biphenyl, preferably tricyclohexylphosphine or tri-t-butylphosphine, and a base such as sodium tert-butoxide, potassium tert-butoxide, sodium tert-pentoxide, sodium ethoxide, sodium carbonate, potassium carbonate, cesium carbonate, sodium hydride, lithium hydride, or potassium hydride, preferably sodium tert-butoxide or sodium tert-pentoxide, in a solvent such as 1,2-dimethoxyethane, tetrahydrofuran, 2-methyltetrahydrofuran, 1,2-diethoxyethane, 1,4-dioxane, toluene, N-methylpyrrolidinone, dimethylacetamide, dimethylformamide, preferably 1,2-dimethoxyethane or tetrahydrofuran, at a temperature between room temperature and 120° C., preferably between 50 and 90° C., for a time period of 1 to 48 hours, preferably for 8 hours, to afford a compound of formula (Ia), (Ib) or (Ic) (or a mixture of all), which may be a mixture of olefin regioisomers of (Ib) and (Ic). Palladium catalyzed alpha-arylations of carbonyl compounds is discussed in a number of sources. Kawatsura, M.; Hartwig, J. F. *J. Am. Chem. Soc.* 1999, 121, 1473–1478; U.S. Pat. No. 6,057,456; Hamann, B. C.; Hartwig, J. F. *J. Am. Chem. Soc.* 1997, 119, 12382–12383; Fox, J. M.; Huang, X.; Chieffi, A.; Buchwald, S. L. *J. Am. Chem. Soc.* 2000, 122, 1360–1370; Palucki, M.; Buchwald, S. L. *J. Am. Chem. Soc.* 1997, 119, 11108–11109; WO 00/02887.

Scheme 2

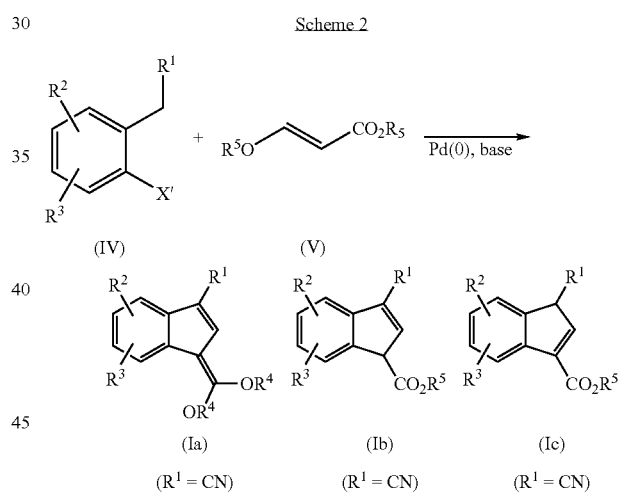

As an alternative to the two steps 1 and 2 in Scheme 1, the single step of Scheme 2 may be carried out in its place. The single step of scheme 2 is a tandem condensation and palladium-catalyzed cyclization. An arene derivative of formula (IV) is combined with an alkoxyacrylate of formula (V) in a solvent such as tetrahydrofuran, 2-methyltetrahydrofuran, 1,2-dimethoxyethane, 1,2-diethoxyethane, 1,4-dioxane, dimethylsulfoxide, dimethylformamide, dimethylacetamide, N-methylpyrrolidinone, methylene chloride, 1,2-dichloromethane, preferably tetrahydrofuran, 2-methyltetrahydrofuran, or 1,2-dimethoxyethane, and is added to a reaction mixture containing base such as sodium tert-butoxide, potassium tert-butoxide, sodium methoxide, sodium ethoxide, sodium tert-pentoxide, sodium carbonate, potassium carbonate, cesium carbonate, lithium diisopropylamide, lithium bis(trimethylsilyl)amide, sodium bis(trimethylsilyl)amide, potassium bis(trimethylsilyl)amide, sodium hydride, or lithium hydride, preferably sodium tert-butoxide or sodium methoxide, a palladium source (could insert palladium catalyst boiler plate here) such as palladium (II) acetate, palladium(II) chloride, bis-acetonitrile palladium(II) chloride, bis-benzonitrile palladium(II) chloride, palladium(II) bromide, tris(dibenzylideneacetone)dipalladium(0), preferably palladium(II) acetate, and a phosphine ligand such as dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)biphenyl, or 2-dicyclohexylphosphino-2'-(N,N-dimethylamino)biphenyl, preferably tricyclohexylphosphine or tri-t-butylphosphine, in one of the above mentioned solvents at a temperature between −78° C. and 50° C., preferably between 0° C. and 30° C., for a period of 1 to 24 hours, preferably for 1 to 5 hours, and then is heated between 25° C. and 120° C., preferably between 50° C. and 90° C. for a period of 1 to 24 hours, preferably 8 hours, to afford any one of the compounds of formulae (Ia), (Ib) or (Ic) (or a mixture of all of them), which may also only be a mixture of olefin regioisomers of formulae (Ib) and (Ic).

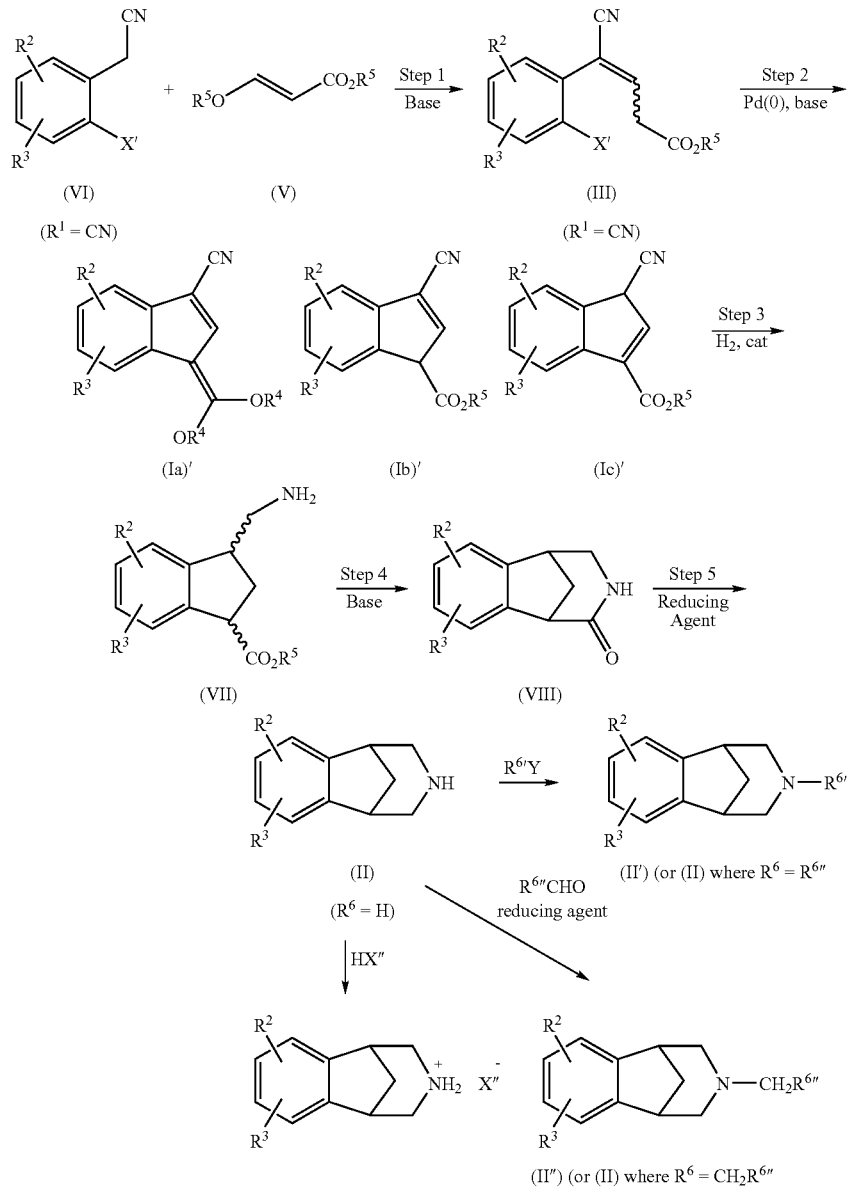

Scheme 3

The present invention also provides a new means to obtain the skeletal framework of compounds of formula (II) employing the indene derivatives of formulae (Ia)', (Ib)' and/or (Ic)' or mixtures thereof (via compounds of formulae (Ia), (Ib) and/or (Ic), where $R^1$ is CN) as shown in Schemes 1 and 2. Scheme 3 provides this new route to compounds of formula (II) using the palladium-catalyzed cyclization methodology. The one-pot cyclization of Scheme 2 may be employed in place of steps 1 and 2 of Scheme 3. After palladium-catalyzed cyclization to the indene intermediate(s), hydrogenolysis (Scheme 4 provides and alternative two-step reduction) and treatment with base leads to efficient construction of the bicyclic core. Reduction of the cyclic amide intermediate leads to the core structure of compounds of formula (II).

lithium hydride, or potassium hydride, preferably sodium tert-butoxide or sodium tert-pentoxide, in a solvent such as 1,2-dimethoxyethane, tetrahydrofuran, 2-methyltetrahydrofuran, 1,2-diethoxyethane, 1,4-dioxane, toluene, N-methylpyrolidinone, dimethylacetamide, dimethylformamide,

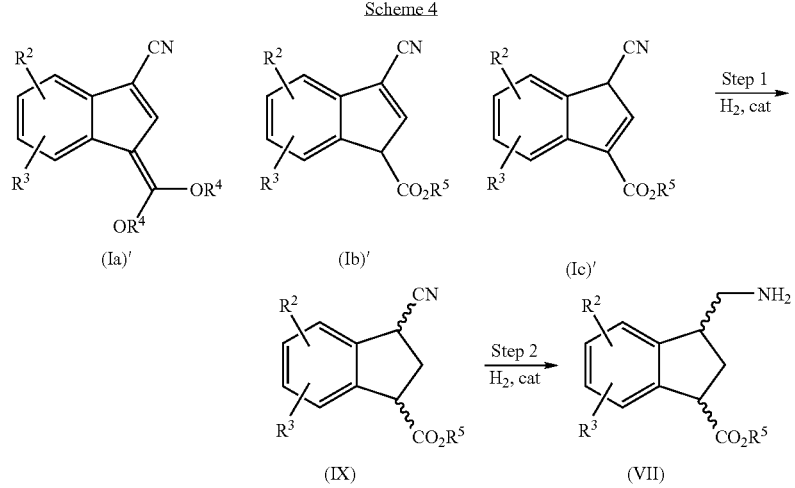

Scheme 4

Step 1 of Scheme 3 is a condensation reaction. An arylacetonitrile derivative of formula (IV) is combined with an alkoxyacrylate of formula (V) in a solvent such as tetrahydrofuran, 2-methyltetrahydrofuran, 1,2-dimethoxyethane, 1,2-diethoxyethane, 1,4-dioxane, dimethylsulfoxide, dimethylformamide, dimethylacetamide, N-methylpyrolidinone, methylene chloride, 1,2-dichloromethane, methanol, ethanol, isopropanol, or propanol, preferably tetrahydrofuran, 2-methyltetrahydrofuran, or 1,2-dimethoxyethane, and is added to base such as sodium tert-butoxide, potassium tert-butoxide, sodium methoxide, sodium ethoxide, sodium tert-pentoxide, sodium carbonate, potassium carbonate, cesium carbonate, lithium diisopropylamide, lithium bis(trimethylsilyl)amide, sodium bis(trimethylsilyl)amide, potassium bis(trimethylsilyl)amide, sodium hydride, or lithium hydride, preferably sodium tert-butoxide or sodium methoxide, in one of the above mentioned solvents at a temperature between −78° C. and 50° C., preferably between 0° C. and 30° C., for a period of 1 to 24 hours, preferably 6 hours, to afford a compound of formula (III) which may be a mixture of olefin isomers.

Step 2 of Scheme 3 is a palladium-catalyzed cyclization reaction. A compound of formula (III) is treated with a palladium source such as palladium(II) acetate, palladium (II) chloride, bis-acetonitrile palladium(II) chloride, bis-benzonitrile palladium(II) chloride, palladium(II) bromide, tris(dibenzylideneacetone)dipalladium(0), preferably palladium(II) acetate, and a phosphine ligand such as dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)biphenyl, or 2-dicyclohexylphosphino-2'-(N,N-dimethylamino)biphenyl, preferably tricyclohexylphosphine or tri-t-butylphosphine, and a base such as sodium tert-butoxide, potassium tert-butoxide, sodium tert-pentoxide, sodium ethoxide, sodium carbonate, potassium carbonate, cesium carbonate, sodium hydride, preferably 1,2-dimethoxyethane or tetrahydrofuran, at a temperature between room temperature and 120° C., preferably between 50 and 90° C., for a time period of 1 to 48 hours, preferably for 8 hours, to afford a compound of formula (Ia)', (Ib)' and/or (Ic)' (or a mixture of any), which may be a mixture of olefin regioisomers of (Ib)' and (Ic)'. Palladium catalyzed alpha-arylations of carbonyl compounds is discussed in a number of sources. Kawatsura, M.; Hartwig, J. F. *J. Am. Chem. Soc.* 1999, 121, 1473–1478; U.S. Pat. No. 6,057,456; Hamann, B. C.; Hartwig, J. F. *J. Am. Chem. Soc.* 1997, 119, 12382–12383; Fox, J. M.; Huang, X.; Chieffi, A.; Buchwald, S. L. *J. Am. Chem. Soc.* 2000, 122, 1360–1370; Palucki, M.; Buchwald, S. L. *J. Am. Chem. Soc.* 1997, 119, 11108–11109; WO 00/02887. As an alternative to steps 1 and 2 in Scheme 3, the single step of Scheme 2 (e.g., where $R^1$ is CN) may be carried out in its place.

Step 3 of Scheme 3 is a hydrogenolysis reaction of a nitrile and an olefin. An indene derivative of formulae (Ia)', (Ib)' or (Ic)' (or a mixture of any of the three) is treated with a hydrogenation catalyst suitable for effectuating the desired reduction. Such catalyst and conditions would be known to one of ordinary skill in the art as reflected in a reference such as *Comprehensive Organic Synthesis*, Vol. 8, "Reduction," Eds.-in-Chief, B. M. Trost and Ian Fleming (Pergamon Press NY 1991). Preferably, the hydrogenation condition are where the catalyst is one such as palladium on carbon, palladium hydroxide on carbon, platinum on carbon, platinum oxide, platinum oxide on carbon, more preferably selected from 5% palladium on carbon, 10% palladium on carbon and 5% platinum on carbon, with an acid such as sulfuric acid, hydrochloric acid, methane sulfonic acid, toluenesulfonic acid, trifluoroacetic acid, acetic acid, formic acid, phosphoric acid or perchloric acid, preferably sulfuric acid, methane sulfonic acid, or a mixture of any of the two acids listed above, in a solvent such as methanol, ethanol, isopropanol, butanol, propanol, ethyl acetate, isopropyl acetate, tetrahydrofuran, toluene, or any mixture of these solvents, preferably methanol or ethanol, under a hydrogen atmosphere up to 7 atmospheres (approximately 100 psi), more preferably 3 to 4 atmospheres (approximately 50 psi), for a time period of 1 to 24 hours preferably 6 hours, to afford a compound of formula (VII) which may be a mixture of diastereomers.

As an alternative to step 3 in Scheme 3, steps 1 and 2 of Scheme 4 may be carried out in its place. Step 1 of Scheme 4 is a hydrogenolysis reaction of an olefin. An indene derivative of formula (Ia)', (Ib)' or (Ic)' (or a mixture of any of the three) is treated with a hydrogenation catalyst suitable for effectuating the desired reduction. Such catalyst and conditions would be known to one of ordinary skill in the art as reflected in a reference such as *Comprehensive Organic Synthesis*, Vol. 8, "Reduction," Eds.-in-Chief, B. M. Trost and Ian Fleming (Pergamon Press NY 1991). Preferably in this instance, the hydrogenation condition are where the catalyst is one such as palladium on carbon, palladium hydroxide on carbon, platinum on carbon, platinum oxide, platinum oxide on carbon, more preferably selected from 5% palladium on carbon, 10% palladium on carbon and 5% platinum on carbon, with an acid such as acetic acid, formic acid, benzoic acid, or salicylic acid, preferably formic acid or acetic acid, in a solvent such as methanol, ethanol, isopropanol, butanol, propanol, ethyl acetate, isopropyl acetate, tetrahydrofuran, toluene, or any mixture of these solvents, preferably methanol or ethanol, under a hydrogen atmosphere up to 7 atmospheres (approximately 100 psi), more preferably 3 to 4 atmospheres (approximately 50 psi), for a time period of 1 to 48 hours preferably 12 hours, to afford a compound of formula (IX) which may be a mixture of diastereomers. The conditions (i.e., choice of acid) for the hydrogenation of Step 1 of Scheme 4 are generally milder and more selective than Step 2, which follows.

Step 2 of Scheme 4 is a hydrogenolysis reaction of a nitrile. An indene derivative of formula (VIII) is treated with a hydrogenation catalyst suitable for effectuating the desired reduction. Such catalyst and conditions would be known to one of ordinary skill in the art as reflected in a reference such as *Comprehensive Organic Synthesis*, Vol. 8, "Reduction," Eds.-in-Chief, B. M. Trost and Ian Fleming (Pergamon Press NY 1991). Preferably, the hydrogenation condition are where the catalyst is one such as palladium on carbon, palladium hydroxide on carbon, platinum on carbon, platinum oxide, platinum oxide on carbon, more preferably selected from 5% palladium on carbon, 10% palladium on carbon and 5% platinum on carbon, with an acid such as sulfuric acid, hydrochloric acid, methane sulfonic acid, toluenesulfonic acid, trifluoroacetic acid, acetic acid, formic acid, phosphoric acid or perchloric acid, preferably sulfuric acid, methane sulfonic acid, or any combination of the acids listed above, in a solvent such as methanol, ethanol, isopropanol, butanol, propanol, ethyl acetate, isopropyl acetate, tetrahydrofuran, toluene, or any mixture of these solvents, preferably methanol or ethanol, under a hydrogen atmosphere up to 7 atmospheres (approximately 100 psi), more preferably 3 to 4 atmospheres (approximately 50 psi), for a time period of 1 to 48 hours preferably 6 hours, to afford a compound of formula (VII) which may be a mixture of diastereomers.

Step 4 of Scheme 3 is an amide formation. An amine of formula (VII) is treated with a base such as sodium tert-butoxide, sodium methoxide, sodium ethoxide, sodium hydroxide, potassium tert-butoxide, potassium methoxide, potassium ethoxide, potassium hydroxide, sodium carbonate, potassium carbonate, cesium carbonate, sodium hydride, triethylamine, methylimidazole, lutidine, pyridine, methylmorpholine, ethylmorpholine, or diisopropylethylamine, preferably sodium tert-butoxide or sodium methoxide, in a solvent such as methanol, ethanol, isopropanol, ethyl acetate, acetonitrile, toluene, water, or a mixture of any of the previously mentioned solvents, preferably methanol or a mixture of methanol and ethyl acetate, at a temperature between 0 and 120° C., preferably at room temperature, for a time period between 30 minutes and 72 hours, preferably 6 hours, to afford a compound of formula (VIII).

Step 5 of Scheme 3 is a reduction of an amide. An amide of formula (VIII) is treated with a reducing agent such as borane tetrahydrofuran complex, diborane, borane dimethylsulfide complex, lithium aluminum hydride, or a combination of sodium borohydride and boron trifluoride, preferably a combination of sodium borohydride and boron trifluoride, in a solvent such as tetrahydrofuran, 1,2-dimethoxyethane, 1,2-diethoxyethane, 2-methyltetrahydrofuran, 1,4-dioxane, or methyl-tert-butyl ether, preferably tetrahydrofuran, at a temperature between 0 and 80° C., preferably 50° C., for time period between 1 and 24 hours, preferably 5 hours. The product is isolated by crystallization as a salt of an acid such as tosic acid, methane sulfonic acid, hydrochloric acid, oxalic acid, citric acid or acetic acid, preferably tosic acid, in a solvent such as isopropanol, hexane, acetone, ethyl acetate, methyl ethyl ketone, or toluene, preferably isopropanol, to afford a compound salt of formula (II).

Also as depicted in Scheme 3, the product of formula (II) (where $R^6$ is now H) may then be isolated by removal of the solvent or isolated by crystallization as a salt, preferably as the salt of an acid such as tosic acid, methane sulfonic acid, hydrochloric acid, oxalic acid, citric acid or acetic acid in a solvent such as isopropanol, hexane, acetone, ethyl acetate, methyl ethyl ketone, or toluene. The use of tosic acid with isopropanol gives very favorable results.

Further in accordance with Scheme 3, a product of formula (II) wherein $R^6$ is $R^{6'}$ and $R^{6'}$ (or formula (II')) is $(C_1-C_6)$alkyl, unconjugated $(C_3-C_6)$alkenyl, benzyl, —$(C_1-C_6)$alkyl-CHO, —$(C_1-C_6)$alkyl-(C=O)—$(C_1-C_6)$alkyl or —$CH_2CH_2$—O—$(C_1-C_4)$alkyl may be recovered by reacting a compound of formula (II) (where $R^6$ is H) with a compound of formula $R^{6'}$—Y wherein Y is a leaving group such as chloro, bromo, iodo or mesylate.

In addition, a product of formula (II) wherein $R^6$ is $(CH_2)$—$R^{6''}$ and $R^{6''}$ (or formula (II")) is $(C_1-C_5)$alkyl, unconjugated $(C_3-C_5)$alkenyl, phenyl, —$(C_1-C_5)$alkyl-CHO, —$(C_1-C_5)$alkyl-(C=O)—$(C_1-C_6)$alkyl or —$CH_2$—O—$(C_1-C_4)$alkyl may be obtained by reacting under reductive amination conditions a compound of formula (II) (where $R^6$ is H) with a compound of formula $R^{6''}$—CHO. Preferably, such a reductive amination can be carried out by catalytic hydrogenation, or with several hydride reagents in a reaction-inert solvent. The catalytic hydrogenation may be carried out in the presence of a metal catalyst such as palladium or Raney nickel. Suitable hydride reagents include borohydrides such as sodium borohydride ($NaBH_4$), sodium cyanoborohydride ($NaBH_3CN$) and sodium triacetoxyborohydride ($NaB(OAc)_3H$), boranes, aluminum-based reagents and trialkylsilanes. Suitable solvents include polar solvents such as methanol, ethanol, methylene chloride, tetrahydrofuran (THF), dioxane and ethyl acetate. This reaction is typically carried out at a temperature from −78° C. to reflux temperature of the solvent, preferably from 0° C. to 25° C. for 5 minutes to 48 hours, preferably from 0.5 to 12 hours.

The process of the invention can be carried out with the $R^2$ and $R^3$ groups, as defined above, already attached to the compound of formula (II). In the alternative, the preparation of a compound of formula (II) may be carried out by first preparing a compound of formula (II) wherein one or both of the $R^2$ and $R^3$ groups is hydrogen, and then adding on additional cyclic structures (i.e., where $R^2$ and $R^3$ together with the carbons to which they are attached, form a four to seven membered monocyclic, or a ten to fourteen membered bicyclic, carbocyclic ring that can be saturated or unsaturated, wherein from one to three of the non-fused carbon atoms of said monocyclic rings, and from one to five of the carbon atoms of said bicyclic rings that are not part of the benzo ring shown in formula (II), may optionally and independently be replaced by a nitrogen, oxygen or sulfur) after carrying out the procedure according to Scheme 3 wherein one or both of the $R^2$ and $R^3$ groups is hydrogen.

General compounds of formula (II) may be made from compounds of formula (II) where $R^2$ and $R^3$ are both H via procedures are set forth in WO 99/35131, corresponding to U.S. Ser. No. 09/402,010, filed Sep. 28, 1999 and U.S. Ser. No. 09/514,002, filed Feb. 25, 2000, both hereby incorporated by reference.

Compounds of formula (II) within the full scope of $R^2$ and $R^3$ as defined may be made in accordance or by analogy to Schemes 5 to 12, below.

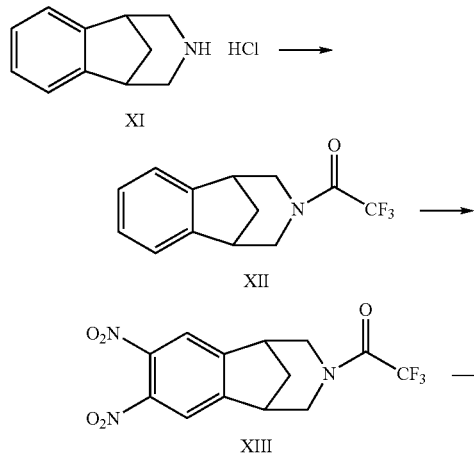

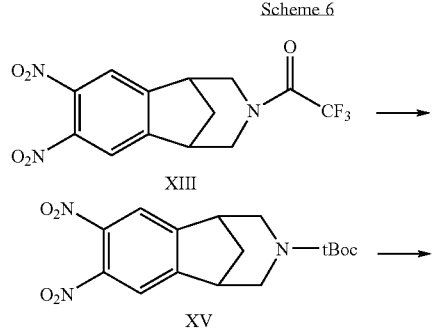

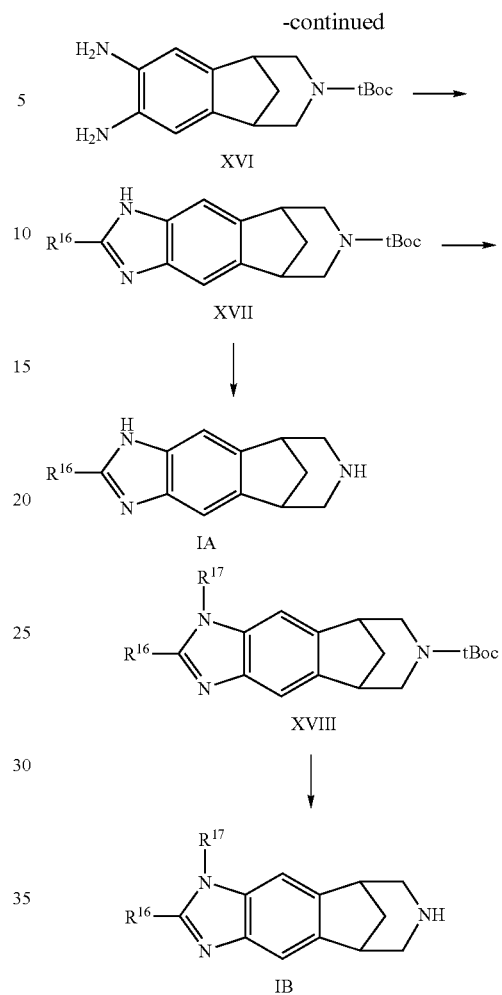

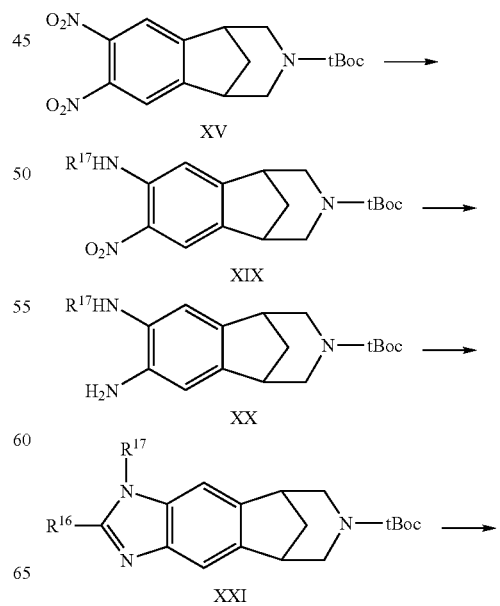

-continued
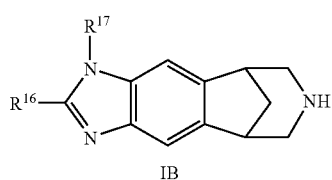
Scheme 8
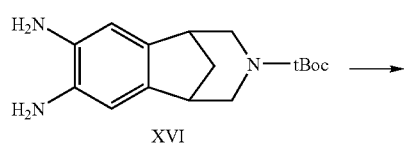
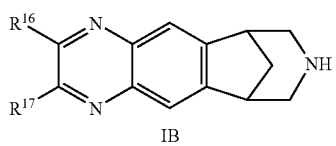
Scheme 9
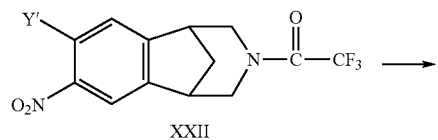
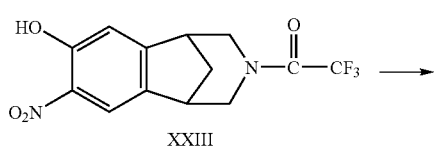
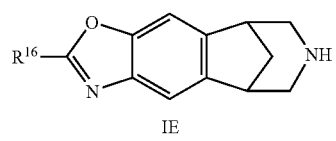
Scheme 10
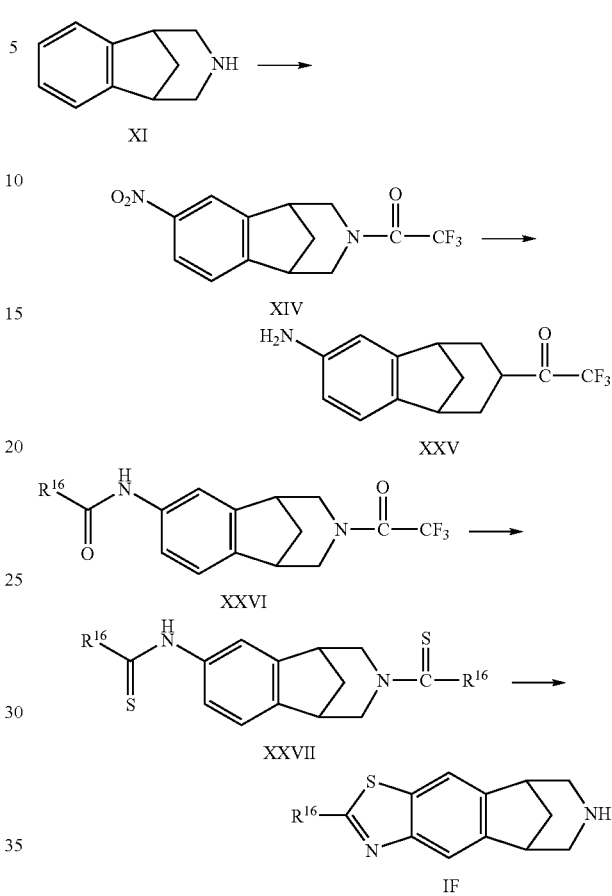
Scheme 11
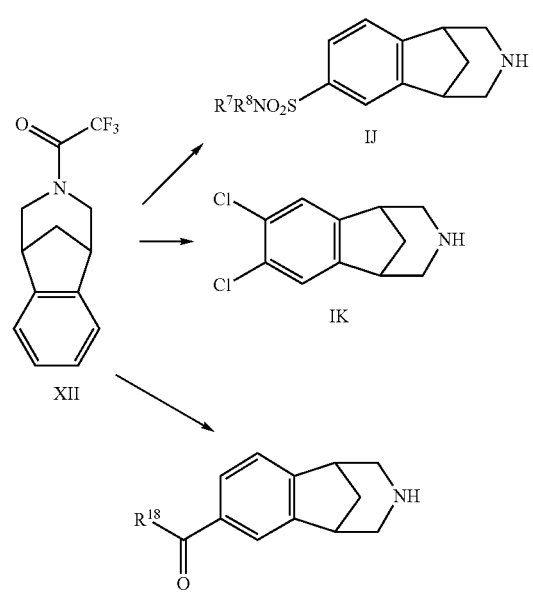

Scheme 12

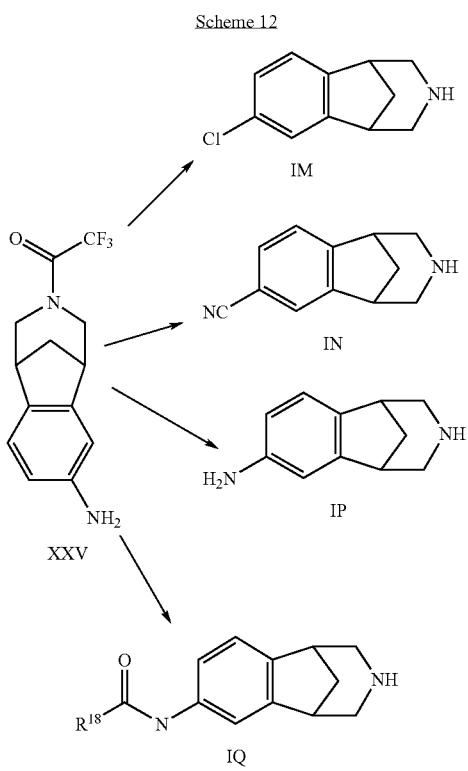

Referring to Scheme 5, the starting material of formula (XI) is reacted with trifluoroacetic anhydride, in the presence of pyridine, to form the compound of formula (XII). This reaction is typically conducted in methylene chloride at a temperature from about 0° C. to about room temperature. Other methods of generating a trifluoroacetate protecting group that may be used are recognized by those of skill in the art.

The compound of formula (XII) is then converted into the dinitro derivative of formula (XIII) by the following process. The compound of the formula (XII) is added to a mixture of 4 or more equivalents of trifluoromethanesulfonic acid ($CF_3SO_2OH$) and 2 to 3 equivalents of nitric acid, in a chlorinated hydrocarbon solvent such as chloroform, dichloroethane (DCE) or methylene chloride. The resulting mixture is allowed to react for about 5 to 24 hours. Both of the foregoing reactions are generally conducted at a temperature ranging from about −78° C. to about 0° C. for about 2 hours, and then allowed to warm to room temperature for the remaining time.

Reduction of the compound of formula (XIII), using methods well known to those of skill in the art, yields the compound of formula (XIV). This reduction can be accomplished, for example, using hydrogen and a palladium catalyst such as palladium hydroxide or palladium on carbon and running the reaction in methanol at about room temperature. The steps of Scheme 5 can also be performed with a nitrogen-protecting group, other than an a trifluoroacetyl group, that would be deemed suitable by those of skill in the art. Other suitable nitrogen protecting groups that can be used in the procedures described throughout this document include —$COCF_3$, —$COCCl_3$, —$COOCH_2CCl_3$, —COO($C_1$–$C_6$)alkyl and —$COOCH_2C_6H_5$. These groups may be added or removed by methods described for each in T. W. Greene and G. M. Wuts, *Protective Groups in Organic Synthesis* (John Wiley & Sons, New York, 1991).

Referring to Scheme 6, the compound of formula (XIII) is converted into the corresponding compound wherein the trifluoroacetyl protecting group is replaced by a t-Boc protecting group (formula (XV)) by reacting it first with an alkali metal or alkaline earth metal (or ammonium) hydroxide or carbonate, and then reacting the isolated product from the foregoing reaction with di-t-butyldicarbonate. Although t-Boc is used in this instance, other appropriate nitrogen-protecting groups known to those of skill in the art may be used. The reaction with the alkali or alkaline earth metal (or ammonium) hydroxide or carbonate is generally carried out in an aqueous alcohol, dioxane or tetrahydrofuran (THF) at a temperature from about room temperature to about 70° C., preferably at about 70° C., for about one to about 24 hours. The reaction of the isolated, unprotected amine or an acid addition salt of such amine, from the above reaction with di-t-butyldicarbonate is preferably carried out in a solvent such as THF, dioxane or methylene chloride at a temperature from about 0° C. to about room temperature. This reaction may or may not be conducted in the presence of a base. When the reactant is a salt of the amine, use of a base is preferred. The resulting compound of formula (XV) can be converted into the corresponding diamino derivative of formula (XVI) using the procedure described above for converting the dinitro compound of formula (XIII) into the corresponding diamino compound of formula (XIV), or other generally accepted nitro group reduction methods known to those of skill in the art, e.g., zinc-, tin-, or iron-mediated reductions, etc.

The conversion of the compound of formula (XVI) into the desired compound of the formula (XVII) can be accomplished by reacting the compound of formula (XVI) with a compound of the formula (XXVIII)

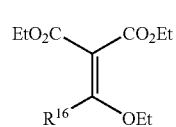

XXVIII wherein $R^{16}$ is hydrogen, ($C_1$–$C_6$)alkyl optionally substituted with from one to seven fluorine atoms, aryl-($C_0$–$C_3$)alkyl wherein said aryl is selected from phenyl and naphthyl, or heteroaryl-($C_0$–$C_3$)alkyl wherein said heteroaryl is selected from five to seven membered aromatic rings containing from one to four heteroatoms selected from oxygen, nitrogen and sulfur, and wherein each of the foregoing aryl and heteroaryl groups may optionally be substituted with one or more substituents, preferably from zero to two substituents, independently selected from ($C_1$–$C_6$)alkyl optionally substituted with from one to seven fluorine atoms, ($C_1$–$C_6$)alkoxy optionally substituted with from one to seven fluorine atoms. The preferred solvent for this reaction is a 10:1 mixture of ethanol/acetic acid. The reaction temperature can range from about 40° C. to about 100° C. It is preferably about 60° C. Other appropriate solvents include acetic acid, ethanol and isopropanol.

Alternate methods of preparing compounds of the formula (XVII) and formula (XVI) are described by Segelstein et al., *Tetrahedron Lett.*, 1993, 34, 1897.

Removal of the t-Boc protecting group from the compound of formula (XVII) yields corresponding compound of formula (IA). The protecting group can be removed using methods well known to those of skill in the art. For example, the compound of formula (XVII) can be treated with an anhydrous acid such as hydrochloric acid, hydrobromic acid, methanesulfonic acid, or trifluoroacetic acid, preferably hydrochloric acid in ethyl acetate, at a temperature from about 0° C. to about 100° C., preferably from about room temperature to about 70° C., for about one to 24 hours.

The compound of formula (XVII) can be converted into the corresponding compound of formula (IB) by reacting it with a compound of the formula $R^{17}Z$, wherein $R^{17}$ is defined as $R^{16}$ is defined above, and Z is a leaving group such as a halo or sulfonate (e.g., chloro, bromo, mesylate or tosylate), in the presence of a base such as an alkali metal hydride, hydroxide or carbonate, preferably potassium hydroxide, in a polar solvent such as water, dimethylsulfoxide (DMSO), THF or DMF, preferably a mixture of DMSO and water, and then removing the protecting group as described above. The reaction with $R^{17}Z$ is generally carried out at a temperature from about room temperature to about 100° C., preferably at about 50° C., for about five hours.

Scheme 7 illustrates an alternate method of preparing compounds of the formula (IB) from the compound of formula (XV). This method is the preferred method of making compounds of the formula (IB) wherein $R^{17}$ is a bulky group such as an aryl or heteroaryl containing group, or when $R^{17}$ can not be attached, as illustrated in Scheme 6, by alkylation or aryl substitution methods. Referring to Scheme 7, the compound of formula (XV) is reacted with the appropriate compound of formula $R^{17}NH_2$ in a polar solvent such as THF, DMF or DMSO, preferably THF, at a temperature from about room temperature to about 100° C., preferably at the reflux temperature, for about four to eighteen hours. The resulting compound of formula (XIX) is then converted into the corresponding compound of the formula (XX) by reducing the nitro group to an amino group using methods well known to those of skill in the art. Such methods are referred to above for the conversion of the compounds of the formula (XIII) into a compound of the formula (XIV) in Scheme 1, and exemplified in experimental Examples 22B and 28B. Closure to the imidazole ring to form the corresponding compound of formula (XXI) can then be accomplished by reacting the compound of formula (XX) from the above reaction with a compound of the formula (XXVIII):

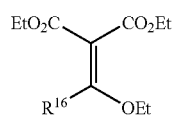

XXVIII wherein $R^{16}$ is defined as above, as described above for converting compounds of the formula (XVI) into those of the formula (XVII).

Removal of the protecting group from the compound of formula (XXI) yields the corresponding compound of formula (IB). This can be accomplished using methods well known in the art, for example, as described above for forming compounds of the formula (IA) from the corresponding compounds of the formula (XVII).

Scheme 8 illustrates a method of preparing compounds of the formula (IC), wherein $R^{16}$ and $R^{17}$ are as defined above. Referring to Scheme 8, the compound of formula (XVI), or analogously formula (XIV) in Scheme 5, is reacted with a compound of the formula

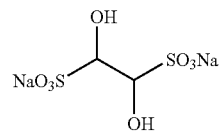

(sodium bisulfite ethane dione addition adduct) in water or another polar solvent such as THF, DMF or DMSO, preferably a mixture of water and a water miscible solvent such as THF, for about one to four hours. The reaction temperature can range from about 40° C. to about 100° C., and is preferably at about the reflux temperature.

Alternatively, the compound of formula (XVI) can be reacted with a compound of the formula

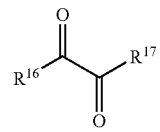

(double condensation reaction) in a polar solvent such as THF, water, or acetic acid, preferably a mixture of water and THF. This reaction is typically carried out at a temperature from about 40° C. to about 100° C., preferably at the reflux temperature, for about two to four hours. The desired quinoxoline of formula (IC) can then be formed by deprotecting the compound formed in either of the foregoing reactions, using the method described above for converting a compound of the formula (XVII) into one of the formula (IA). Alternatively, in place of compound (XVI) in Scheme 8, the compound (XIV) of Scheme 5 may be used analogously in this procedure with deprotection/reprotection as outlined in Scheme 6 (i.e., the process of transforming (XIII) to (XV)) in order to arrive at ultimately the compound (IC). In general, alternative nitrogen protection groups are equally suited to the procedure of Scheme 8.

Scheme 9 illustrates a method of preparing compounds of the formula (II) wherein $R^2$ and $R^3$, together with the benzo ring to which they are attached, form a benzoxazole ring system. Such a compound, wherein $R^1$ is hydrogen, is depicted in Scheme 9 as chemical formula (IE). Referring to Scheme 9, the compound of formula (XXII), wherein Y' is nitro, halo, trifluoromethanesulfonate or a diazonium salt, is reacted with potassium acetate or another alkali or alkaline earth metal carboxylate in a solvent such as dimethylsulfoxide (DMSO), DMF or acetonitrile, preferably DMSO. This reaction is generally allowed to run for about 12–24 hours. Appropriate reaction temperatures range from about 70° C. to about 140° C. Approximately 10° C. is preferred.

The above reaction yields the compound of formula (XXIII), which can then be converted into the desired compound having formula (IE) by the following procedure. First, the compound of formula (XXIII) is reduced by reaction with hydrogen and a palladium or platinum catalyst such as palladium hydroxide in methanol at a temperature from about 0° C. to about 70° C., preferably at about room temperature, to form the corresponding amino derivative. The product of this reaction is then reacted with an acid chloride of the formula $R^{16}COCl$ or an acid anhydride of the formula $(R^{16}CO)_2O$ wherein $R^{16}$ is $(C_1-C_6)$alkyl, or a compound of the formula $R^{16}C(OC_2H_5)_3$, in an appropriate inert solvent such as decalin, chlorobenzene or xylenes. A mixture of xylenes is preferred. This reaction is typically conducted at a temperature from about 120–150° C., preferably at about 140° C. When $R^{16}COCl$ is used as a reactant, it is preferable to add a stoichiometric amount of triethylamine (TEA) or another organic tertiary amine base and a catalytic amount of pyridinium p-toluenesulfonic acid or pyridinium p-toluenesulfonate (PPTs) to the reaction mixture. When $R^{16}C(OC_2H_5)_3$ is used as a reactant, it is preferable to add a catalytic amount of PPTs to the reaction mixture.

Removal of the trifluoroacetyl nitrogen protecting group yields the desired compound of the formula (IE). This can be accomplished using methods well known to those of skill in the art, for example, reacting the protected compound with a lower alkanol and an aqueous alkali or alkaline earth metal (or ammonium) hydroxide or carbonate, aqueous sodium carbonate, at a temperature from about 50° C. to about 100° C., preferably at about 70° C., for about two to six hours.

Scheme 10 illustrates the preparation of compounds of the formula (II) wherein $R^1$ is hydrogen and $R^2$ and $R^3$, together with the benzo ring to which they are attached, form a benzothiazole ring system. Referring to Scheme 10, the compound of formula (XI) is reacted with trifluoroacetic anhydride to form the corresponding compound wherein the ring nitrogen is protected by a trifluoroacetyl group, and the resulting nitrogen protected compound is then reacted with two equivalents of trifluoromethanesulfonic anhydride and one equivalent of nitric acid to form the corresponding compound of formula (XXIV), wherein there is a single nitro substituent on the benzo ring. The reaction with trifluoroacetic acid is typically conducted in the presence of pyridine. Both of the above reactions are typically conducted in a reaction inert solvent such as a chlorinated hydrocarbon solvent, preferably methylene chloride, at a temperature from about 0° C. to about room temperature, preferably at about room temperature.

The above transformation can also be accomplished using other nitration methods known to those skill in the art. Reduction of the nitro group to an amine group can be accomplished as described above to provide a compound of the formula (XXV).

The compound of formula (XXV) is then reacted with a carboxylic acid halide or anhydride of the formula $R^{16}COX'''$ or $(R^{16}CO)_2O$, wherein $X'''$ is halo and $R^{16}$ is hydrogen or $(C_1-C_6)$alkyl, and pyridine, TEA or another tertiary amine base, to form a compound of the formula (XXVI), which can then be converted to the desired compound having formula (XXVII) by reacting it with Lawesson's reagent:

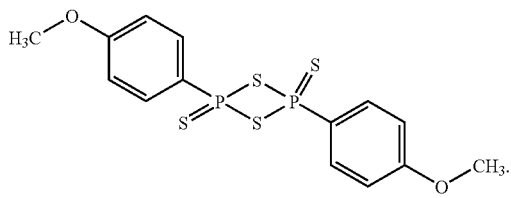

The reaction with $R^{16}COX'''$, wherein $X'''$ is halo, or $(R^{16}CO)_2O$ is generally carried out at a temperature from about 0° C. to about room temperature, preferably at about room temperature. The reaction with Lawesson's reagent is generally carried out in a reaction inert solvent such as benzene or toluene, preferably toluene, at a temperature from about room temperature to about the reflux temperature of the reaction mixture, preferably at about the reflux temperature.

Closure to the benzothiazole ring and nitrogen deprotection to form the desired compound of formula (IF) can be accomplished by reacting the compound of formula (XXVII) with potassium ferricyanide and sodium hydroxide in a mixture of water and methanol ($NaOH/H_2O/CH_3OH$), at a temperature from about 50° C. to about 70° C., preferably at about 60° C. for about 1.5 hours.

Schemes 11 and 12 illustrate methods of preparing compounds of the formula (II) wherein $R^1$ is hydrogen, and $R^2$ and $R^3$ represent a variety of different substituents, as defined above, but do not form a ring.

Scheme 11 illustrates methods of preparing compounds of the formula (II) wherein: (a) $R^1$ is hydrogen and $R^2$ is $R^7R^8NO_2S$—; (b) $R^1$ and $R^2$ are both chloro; and (c) $R^1$ is hydrogen and $R^2$ is $R^3C(=O)$—. These compounds are referred to in Scheme 11, respectively, as compounds of formulas IJ, IK and IL.

Referring to Scheme 11, compounds of the formula (IJ) can be prepared by reacting the compound of formula (XII) with two or more equivalents of a halosulfonic acid, preferably chlorosulfonic acid, at a temperature from about 0° C. to about room temperature. Reaction of the chlorosulfonic acid derivative so formed with an amine having the formula $R^7R^8NH$, wherein $R^7$ and $R^8$ are defined as above, followed by removal of the nitrogen protecting group, yields the desired compound having formula (IJ).

Compounds of the formula (IK) can be prepared by reacting the compound of formula (XII) with iodine trichloride in a chlorinated hydrocarbon solvent, followed by removal of the nitrogen protecting group. The reaction with iodine trichloride is typically carried out at a temperature from about 0° C. to about room temperature, and is preferably carried out at about room temperature. In a similar fashion, the analogous mono- or di-brominated or mono- or di-iodinated compounds can be prepared by reacting the compound of XII with N-iodosuccinamide or N-bromosuccinimide in a trifluoromethanesulfonic acid solvent, followed by removal of the nitrogen protecting group as described above.

Reaction of the compound of XII with an acid halide of the formula $R^{18}COCl$ or an acid anhydride of the formula $(R^{18}CO)_2O$, where $R^{18}$ is H or $(C_1-C_6)$alkyl, with or without a reaction inert solvent such as a chlorinated hydrocarbon solvent, preferably methylene chloride, in the presence of Lewis acid such as aluminum chloride, at a temperature from about 0° C. to about 100° C., followed by nitrogen deprotection, yields the compound of formula (IL). The reaction with the acid halide or anhydride can be carried out using other known Lewis acids or other Friedel-Crafts acylation methods that are known in the art.

The reactions described herein in which —$NO_2$, —$SO_2NR^7R^8$, —$COR^{18}$, I, Br or Cl are introduced on the compound of formula (XII), as depicted in Scheme 11 and described above, can be performed on any analogous compound wherein $R^2$ is hydrogen, $(C_1-C_6)$alkyl, halo, $(C_1-C_6)$alkoxy or —$NHCONR^7R^8$, producing compounds of the formula (II) wherein $R^2$ and $R^3$ are defined as in the definition of compounds of the formula (II) above.

Compounds that are identical to those of the formula (IL), but which retain the nitrogen protecting group, can be converted into the corresponding O-acyl substituted compounds, i.e., those wherein the —$C(=O)R^{18}$ group of formula (IL) is replaced with a —O—$C(=O)R^{18}$ group, using Baeyer-Villiger processes well known to those skilled in the art. The resulting compounds can be partially hydrolyzed to yield the corresponding hydroxy substituted compounds, and then alkylated to form the corresponding alkoxy-substituted compounds. Also, such O-acyl substituted compounds can be used to prepare variably substituted benzisoxazoles.

Scheme 12 illustrates methods of making compounds of the formula (II) wherein: (a) $R^1$ is hydrogen and $R^2$ is chloro; (b) $R^1$ is hydrogen and the benzo ring is substituted with cyano; (c) $R^1$ is hydrogen and the benzo ring is substituted with amino; and (d) $R^1$ is hydrogen and the benzo ring is substituted with $R^{18}C(=O)N(H)$—. These compounds are referred to in Scheme 12, respectively, as compounds of the formulae (IM), (IN), (IP) and (IQ).

Compounds of formula (IM) can be prepared from compounds of the formula (XXV) by generation of a diazonium salt with, for instance, an alkali metal nitrite and strong mineral acid (e.g., hydrochloric acid, sulfuric acid, hydrobromic acid) in water, followed by reaction with a copper halide salt, such as copper (II) chloride. Nitrogen deprotection by the methods described above yields the desired compound of formula (IM). Alternative methods for the generation of diazonium salts, as known and practiced by those of skill in the art, can also be used. The foregoing reaction is generally carried out by temperatures ranging from about 0° C. to about 60° C., preferably about 60° C. for about 15 minutes to one hour.

Reaction of the diazodium salt, prepared as described above, with potassium iodide in an aqueous medium provides the analogous iodide derivative. This reaction is generally carried out at a temperature from about 0° C. to about room temperature, preferably at about room temperature. The resulting compound, or its analogous N-tert-butylcarbonate protected form, can be used to prepare the corresponding cyano derivative by reaction with copper (II) cyanide and sodium cyanide in DMF, N,N-dimethylpropylurea (DMPU) or DMSO, preferably DMF, at a temperature from about 50° C. to about 180° C., preferably about 150° C. Nitrogen deprotection as described above provides the desired compound of formula (IM).

The above described iodide derivative can also be used to access a variety of other substituents such as aryl, acetylene and vinyl substituents, as well as the corresponding carbonyl esters and amides, by palladium and nickel catalyzed processes known to those of skill in the art, such as Heck, Suzuki and Stille couplings and Heck carbonylations. These compounds and others, wherein $R^2$ is halo, alkyl, alkoxy, etc., may be similarly functionalized to generate compounds wherein $R^2$ and $R^3$ are as defined above.

Nitrogen deprotection of the compound of formula (XXV) provides the compound of the formula (IP). The compound of formula (XXV) can be reacted with a acyl group having the formula $R^{18}COCl$ or $(R^{18}CO)_2O$ using the methods described above, followed by nitrogen deprotection to provide compounds of the formula (IQ). In a similar fashion, treatment of the protected amine with a compound having the formula $R^{18}SO_2X''''$, when $X''''$ is chloro or bromo, followed by nitrogen deprotection, provides the corresponding sulfonamide derivative.

As noted above, suitable amine protecting groups that can be used, alternatively, in the procedures described throughout this document include —$COCF_3$, —$COCCl_3$, —$COOCH_2CCl_3$, —$COO(C_1-C_6)alkyl$ and —$COOCH_2C_6H_5$. These groups may be removed by methods described for each in Greene et al.'s Protective Groups in Organic Chemistry, referred to above. Instances where protecting groups would be modified under the reaction conditions, such as, e.g., a —$COOCH_2C_6H_5$ group during nitration, still permit said procedures to operate as described with said modified protecting group. Modifying the order of protecting group incorporation and/or methods of functional group introduction or modification may also be applied where appropriate.

In each of the reactions discussed above, or illustrated in Schemes 5–12, above, pressure is not critical unless otherwise indicated. Pressures from about 0.5 atmospheres to about 5 atmospheres are generally acceptable, with ambient pressure, i.e., about 1 atmosphere, being preferred as a matter of convenience.

Biological Assay

The effectiveness of the active compounds made by the processes of the present invention in suppressing nicotine binding to specific receptor sites is determined by the following procedure which is a modification of the methods of Lippiello, P. M. and Fernandes, K. G. (in *The Binding of L-[$^3$H]Nicotine To A Single Class of High-Affinity Sites in Rat Brain Membranes*, Molecular Pharm., 29, 448–54, (1986)) and Anderson, D. J. and Americ, S. P. (in *Nicotinic Receptor Binding of $^3$H-Cystisine, $^3$H-Nicotine and $^3$H-Methylcarmbamylcholine In Rat Brain*, European J. Pharm., 253, 261–67 (1994)).

The compounds of the formula (II) and their pharmaceutically acceptable salts (hereafter "the active compounds") prepared by the methods of the invention can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds prepared by the methods of the invention can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds prepared by the methods of the invention topically and this can be done by way of creams, a patch, jellies, gels, pastes, ointments and the like, in accordance with standard pharmaceutical practice.

The preparation of other compounds of the present invention not specifically described in the foregoing experimental section can be accomplished using combinations of the reactions described above that will be apparent to those skilled in the art. Intermediate compounds of invention referred to above may contain chiral centers, and therefore may exist in different enantiomeric and diastereomeric forms; this invention is directed to all such optical and stereoisomers of said intermediate compounds, as well as mixtures thereof.

EXAMPLES

The present invention is illustrated by the following examples. It will be understood, however, that the invention is not limited to the specific details of these examples.

Example 1

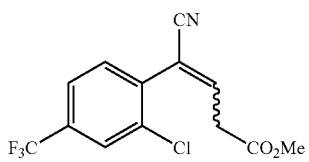

4-(2-CHLORO-4-TRIFLUOROMETHYL-PHENYL)-4-CYANO-BUT-3-ENOIC ACID METHYL ESTER

To a solution of sodium tert-butoxide (3.28 g, 34.2 mmol) in tetrahydrofuran (20 mL) at 0° C. was added a solution of methyl 3-methoxyacrylate (2.65 g, 22.8 mmol) and (2-chloro-4-trifluoromethyl-phenyl)-acetonitrile (5.00 g, 22.8 mmol) in tetrahydrofuran (20 mL) dropwise over 45 minutes. The red solution was stirred at 0° C. for 3 hours and then allowed to warm to 10° C. over another 2 hours. The reaction was then treated with 0.2 M aqueous citric acid (50 mL) and extracted with a 2:1 mixture of methyl tert-butyl ether and hexanes (75 mL). The organic layer was washed with an aqueous saturated solution of sodium chloride (50 mL). The organic solution was passed through a short column of silica gel, washing the residual material through the pad with additional methyl tert-butyl ether. The filtrate was concentrated in vacuo to afford 4-(2-chloro-4-trifluoromethyl-phenyl)-4-cyano-but-3-enoic acid methyl ester as a red oil (6.74 g, 97%). Major olefin isomer: $^1$HNMR (400 MHz, CDCl$_3$) δ 7.71 (s, 1H), 7.58 (d, 1H, J=8.3), 7.49 (d, 1H, J=8.3), 6.89 (t, 1H, J=7.1), 3.78 (s, 3H), 3.69 (d, 2H, J=7.1); $^{13}$C NMR (100 MHz, CDCl$_3$) δ 169.4, 145.9, 136.1, 133.7, 133.0 (q, J=33.5), 131.5, 127.6 (q, J=3.8), 124.5 (q, J=3.8), 123.2 (q, J=292), 115.4, 114.7, 52.7, 36.7; IR (ATR, neat) 2957, 2224, 1740, 1438, 1395, 1319, 1268, 1172, 1128, 1080, 1010, 963, 892, 831, 719, 655 cm$^{-1}$. Minor olefin isomer: $^1$H-NMR (400 MHz, CDCl$_3$) δ 7.76 (s, 1H), 7.61 (d, 1H, J=7.8), 7.43 (d, 1H, J=7.8), 7.02 (t, 1H, J=7.8), 3.71 (s, 3H), 3.11 (d, 2H, J=7.8).

Example 2

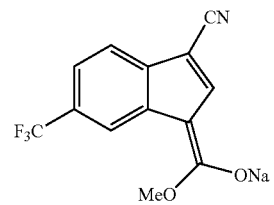

3-(HYDROXY-METHOXY-METHYLENE)-5-TRIFLUOROMETHYL-3H-INDENE-1-CARBONITRILE, SODIUM SALT

A solution of 4-(2-chloro-4-trifluoromethyl-phenyl)-4-cyano-but-3-enoic acid methyl ester (1.00 g, 3.29 mmol), palladium (II) acetate (37.0 mg, 0.165 mmol), and tricyclohexylphosphine (55 mg, 0.197 mmol) in ethylene glycol dimethyl ether (8.0 mL) was stirred for 10 minutes at room temperature under a nitrogen atmosphere and then sodium tert-butoxide (791 mg, 8.23 mmol) was added. The reaction mixture was heated to a reflux for 48 hours. The reaction was cooled to room temperature and partitioned between methyl tert-butyl ether (25 mL) and 0.25 M aqueous potassium dihydrogen phosphate (25 mL). The aqueous layer was separated and treated with ethyl acetate (30 mL) and 4.0 M aqueous hydrochloric acid (3 mL). The ethyl acetate extract was washed with a saturated aqueous solution of sodium chloride (20 mL), diluted with methanol (10 mL) and stirred with potassium carbonate (25 mg, 0.181 mmol) for 1 hour. The organic solution was concentrated in vacuo to afford 3-(hydroxy-methoxy-methylene)-5-trifluoromethyl-3H-indene-1-carbonitrile, sodium salt, as a foamy, red solid (727 mg, 83%). $^1$H-NMR (400 MHz, CD$_3$OD) δ 8.29 (s, 1H), 7.73 (s, 1H), 7.50 (d, 1H, J=8.3), 7.12 (d, 1H, J=8.3), 3.82 (s, 3H); $^{13}$C NMR (100 MHz, CD$_3$OD) δ 169.1, 138.7, 134.7, 132.2, 127.9 (q, J=270), 123.4, 121.8 (q, J=30.5), 118.5 (q, J=4.3), 118.3, 115.7 (q, J=3.8), 105.2, 81.0, 50.9; IR (ATR, neat) 2953, 2179, 1612, 1466, 1325, 1389, 1325, 1283, 1194, 1153, 1101, 1073, 1014, 900, 838, 814, 777, 753, 708, 644 cm$^{-1}$.

Example 3

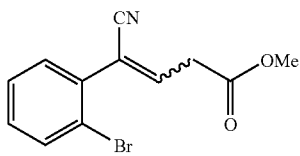

4-(2-BROMO-PHENYL)-4-CYANO-BUT-3-ENOIC ACID METHYL ESTER

A solution of 2-bromo-phenylacetonitrile (6.62 mL, 51.0 mmol) and methyl-3-methoxyacrylate (5.32 mL, 49.5 mmol) in tetrahydrofuran (10 ml) was added to a suspension of sodium tert-butoxide (5.05 g, 51.0 mmol) in tetrahydrofuran (70 mL) at 0° C. over 10 minutes under a stream of nitrogen. The reaction mixture was warmed to room temperature and after 15 minutes diluted with methyl tert-butyl ether (240 mL). To the mixture was added 0.2 N aqueous citric acid until the aqueous layer had a pH of 2 (80 mL). The organic layer was separated and washed with a saturated aqueous solution of sodium chloride (2×80 mL), dried over anhydrous sodium sulfate, filtered through a pad of Celite and silica (4:1) and concentrated in vacuo to provide 4-(2-bromo-phenyl)-4-cyano-but-3-enoic acid methyl ester as a pale yellow oil (13.8 g, 96%). Major isomer $^1$H NMR (400 MHz, CDCl$_3$) δ 7.59 (dd, 1H, J=7.6, 1.2), 7.57–719 (m, 3H), 6.71 (t, 1H, J=7.1), 3.71 (s, 3H), 3.61 (d, 2H, J=7.1); $^{13}$C NMR (100 MHz, CDCl$_3$) δ 169.7, 144.4, 133.7, 131.4, 131.1, 128.3, 122.5, 118.1, 117.3, 115.3, 52.7, 36.6; IR (ATR, neat) 1737, 1434, 1319, 1199, 1171, 1026, 755 cm$^{-1}$. Minor isomer $^1$H NMR (400 MHz, CDCl$_3$) δ 7.61 (dd, 1H, J=7.6, 1.0), 7.57–7.19 (m, 3H), 6.9 (t, 1H, J=7.5), 3.64 (s, 3H), 3.06 (d, 2H, J=7.5).

Example 4

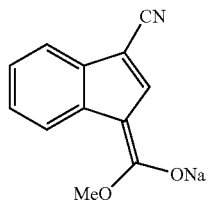

3-(HYDROXY-METHOXY-METHYLENE)-3H-INDENE-1-CARBONITRILE, SODIUM SALT

A solution of 4-(2-bromo-phenyl)-4-cyano-but-3-enoic acid methyl ester (12.4 g, 44.4 mmol) in ethylene glycol dimethyl ether (100 mL) was purged with nitrogen for 10 minutes and charged with tricyclohexylphosphine (311 mg, 1.11 mmol) and followed by palladium (II) acetate (199 mg, 0.890 mmol). The mixture was stirred at room temperature until reaction was a homogeneous solution and charged with sodium tert-butoxide (11.0 g, 111 mmol). The reaction mixture was heated to 85° C. and stirred for 5 hours, then cooled to room temperature and diluted with methyl tert-butyl ether (300 mL). To the cloudy mixture was added a 0.25 M aqueous solution of potassium dihydrogen phosphate (300 mL) and the aqueous layer was separated and acidified with 4.0 M aqueous hydrochloric acid (50 mL) then extracted with ethyl acetate (300 mL). The organic layer was separated and washed with a saturated aqueous solution of sodium chloride (2×200 mL), diluted with methanol (150 mL) and dried over potassium carbonate (2.00 g). After 2 hours the heterogeneous suspension was filtered through a pad of Celite and the crude product concentrated in vacuo to provide 3-(hydroxy-methoxy-methylene)-3H-indene-1-carbonitrile, sodium salt, as a dark brown solid (6.80 g, 77%). The crude solid was dissolved in anhydrous MeOH (30 mL) and stored as a solution. $^1$H NMR (400 MHz, d$_4$-MeOH) δ 7.82–7.30 (m, 5H), 3.66 (s, 3H); $^{13}$C NMR (100 MHz, d$_4$-MeOH) δ 168.3, 135.7, 132.3, 131.9, 123.2, 120.2, 119.3, 118.6, 117.2, 102.7, 79.4, 49.6; IR (ATR, neat) 2175, 1608, 1453, 1385, 1322, 1256, 1189, 1065, 1013, 751, 632 cm$^{-1}$.

Example 5

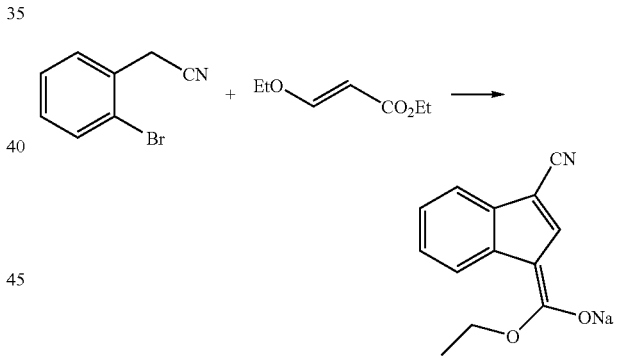

3-(ETHOXY-HYDROXY-METHYLENE)-3H-INDENE-1-CARBONITRILE, SODIUM SALT

A solution of tricyclohexylphosphine (21.5 mg, 0.0770 mmol) in ethylene glycol dimethyl ether (10 mL) under nitrogen was charged with palladium (II) acetate (11.5 mg, 0.0510 mmol). The reaction was stirred at room temperature until the solution was homogenous (approx. 15 minutes), cooled to 0° C. and charged with sodium tert-butoxide (2.53 g, 25.5 mmol). After 5 minutes a solution of 2-bromo-phenylacetonitrile (1.32 mL, 10.2 mmol) and ethyl-3-ethoxyacrylate (1.47 mL, 10.2 mmol) in ethylene glycol dimethyl ether (10 ml) was added dropwise over 10 minutes. Upon complete addition, the reaction was warmed to room temperature then heated to 85° C. for 1 hour. The reaction was cooled to room temperature then diluted with ethyl acetate (50 mL) and poured into aqueous potassium dihydrogen phosphate (0.25 M, 50 mL), pH=7. The aqueous layer was saturated by addition of sodium chloride as solid and the organic layer separated and washed with aqueous saturated sodium chloride (1×50 mL), dried over anhydrous sodium sulfate, filtered and concentrated in vacuo affording 3-(ethoxy-hydroxy-methylene)-3H-indene-1-carbonitrile, sodium salt, as a dark brown oil (1.74 g, 84%) which solidifies on standing. $^1$H NMR (400 MHz, CD$_3$CN) δ 8.04 (d, 1H, J=6.0), 7.58 (s, 1H), 7.43 (d, 1H, J=6.0), 6.98–6.91 (m, 2H), 4.25 (q, 2H, J=7.2), 1.35 (t, 3H, J=7.2); $^{13}$C NMR (100 MHz, CD$_3$CN) δ 166.7, 135.5, 132.3, 131.3, 122.8, 120.5, 119.0, 118.4, 117.7, 103.3, 79.2, 58.2, 14.6; IR (ATR, neat) 2176, 1597, 1465, 1257, 1195, 1068, 1029, 754 cm$^{-1}$.

Example 6

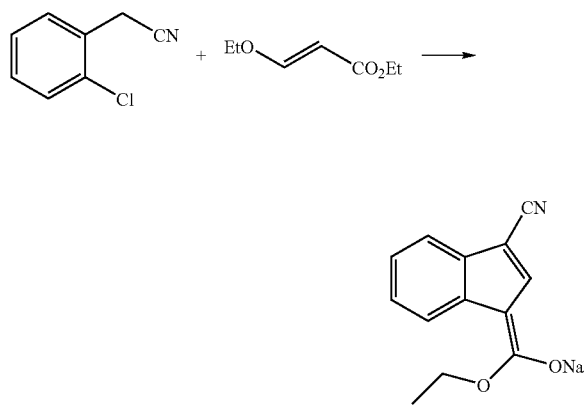

3-(ETHOXY-HYDROXY-METHYLENE)-3H-INDENE-1-CARBONITRILE, SODIUM SALT

A solution of tricyclohexylphosphine (204 mg, 0.720 mmol) in ethylene glycol dimethyl ether (10 mL) under nitrogen was charged with palladium (II) acetate (148 mg, 0.660 mmol). The reaction was stirred at room temperature until the solution was homogenous (approx. 25 minutes), cooled to 0° C. and charged with sodium tert-butoxide (1.63 g, 16.6 mmol). After 10 minutes a solution of 2-chlorophenylacetonitrile (1.00 g, 6.60 mmol) and ethyl-3-transethoxy-acrylate (953 μL, 6.60 mmol) in ethylene glycol dimethyl ether (10 ml) was added dropwise over 5 minutes. Upon complete addition, the reaction was warmed to room temperature and then heated to 85° C. for 22 hours. The reaction was cooled to room temperature then diluted with methyl tert-butyl ether (30 mL) and poured into aqueous potassium dihydrogenphosphate (0.25 M, 40 mL), pH=7. The aqueous layer was separated then saturated by addition of solid sodium chloride and extracted with ethyl acetate (1×50 mL). The organic layer was separated and washed with aqueous saturated sodium chloride (2×30 mL), dried over sodium sulfate, filtered and concentrated in vacuo affording 3-(ethoxy-hydroxy-methylene)-3H-indene-1-carbonitrile, sodium salt, as a light orange oil (1.06 g, 5.0 mmol, 75%). For physical data see Example 5 above.

Example 7

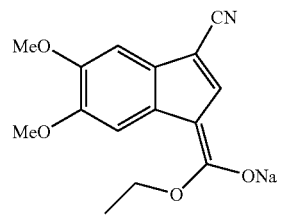

3-(ETHOXY-HYDROXY-METHYLENE)-5,6-DIMETHOXY-3H-INDENE-1-CARBONITRILE, SODIUM SALT

A solution of tricyclohexylphosphine (82.0 mg, 0.293 mmol) in ethylene glycol dimethyl ether (10 mL) under nitrogen was charged with palladium (II) acetate (43.7 mg, 0.195 mmol). The reaction was stirred at room temperature until the solution was homogeneous (approx. 15 minutes) and stirred an additional 5 minutes before cooling to 0° C. and charging with sodium tert-butoxide (996 mg, 9.75 mmol). After 5 minutes a solution of 2-bromo-4,5-dimethoxyphenylacetonitrile (1.00 g, 3.90 mmol) and ethyl-3-ethoxyacrylate (0.564 ml, 3.90 mmol) in ethylene glycol dimethyl ether (5 ml) was added dropwise over 10 minutes. Upon complete addition the reaction mixture was warmed to room temperature and then heated to 85° C. for 16 hours. The reaction was cooled to room temperature then diluted with methyl tert-butyl ether (50 mL) and poured into aqueous potassium dihydrogenphosphate (0.25 M, 100 mL). The aqueous layer was separated and solid sodium chloride was added to the aqueous layer until saturated. The aqueous layer was extracted with ethyl acetate (1×125 mL) and this organic layer was washed with aqueous saturated sodium chloride 12×35 ml), dried over sodium sulfate, filtered and concentrated in vacuo affording 3-(ethoxy-hydroxy-methylene)-5,6-dimethoxy-3H-indene-1-carbonitrile, sodium salt, as a dark brown oil (906 mg, 3.3 mmol, 85%) which crystallized on standing. $^1$H NMR (400 MHz, d$_4$-MeOH) δ 7.64 (s, 1H), 7.46 (s, 1H), 6.99 (s, 1H), 4.56 (q, 2H, J=7.1), 3.86 (s, 6H), 1.38 (t, 3H, J=7.05); $^{13}$C NMR (100 MHz, d$_4$-MeOH) δ 167.8, 145.0, 144.5, 130.2, 129.4, 126.4, 123.3, 112.5, 104.0, 102.6, 100.7, 79.0, 58.4, 55.6, 14.1; IR (ATR, neat) 3499, 2164, 1629, 1482, 1449, 1282, 1207, 1157, 1124, 1076, 845, 769 cm$^{-1}$.

Example 8

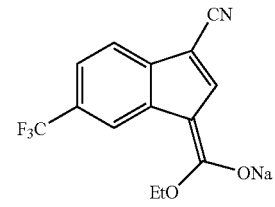

3-(HYDROXY-ETHOXY-METHYLENE)-5-TRIF-LUOROMETHYL-3H-INDENE-1-CARBONI-TRILE, SODIUM SALT

A solution of palladium (II) acetate (102 mg, 0.454 mmol), and tricyclohexylphosphine (153 mg, 0.546 mmol) in ethylene glycol dimethyl ether (10 mL) was stirred for 15 minutes at room temperature under a nitrogen atmosphere and then sodium tert-butoxide (2.19 g, 22.8 mmol) was added. The reaction mixture was cooled to 0° C. and a solution of 2-chloro-4-trifluoromethyl-phenyl)-acetonitrile (2.00 g, 9.11 mmol) and ethyl 3-ethoxyacrylate (1.45 mL, 10.0 mmol) in ethylene glycol dimethyl ether (10 mL) was added dropwise. Once addition was complete the reaction mixture was allowed to warm to room temperature and stir for 4 hours. The reaction was then heated to 60° C. for 18 hours. The reaction was cooled to room temperature and partitioned between methyl tert-butyl ether (45 mL), hexane (20 mL) and 0.25 M aqueous potassium dihydrogenphosphate (60 mL). The aqueous layer was separated, saturated with sodium chloride and extracted with ethyl acetate (60 mL). The ethyl acetate extract was dried over anhydrous sodium sulfate and concentrated in vacuo to afford 3-(hydroxy-ethoxy-methylene)-5-trifluoromethyl-3H-indene-1-carbonitrile, sodium salt, as a foamy, red solid (1.86 g, 67%). $^1$HNMR (400 MHz, CD$_3$OD) δ 8.31 (s, 1H), 7.70 (s, 1H), 7.49 (d, 1H, J=7.9), 7.11 (d, 1H, J=7.9), 4.28 (q, 2H, J=7.1), 1.39 (t, 3H, J=7.1); $^{13}$C NMR (100 MHz, CD$_3$OD) δ 167.6, 137.4, 133.4, 131.0, 126.7 (q, J=201), 122.1, 120.5 (q, J=22.7), 117.3 (q, J=3.3), 117.1, 114.3 (q, J=2.5), 104.2, 79.6, 58.7, 14.0; IR (ATR, neat) 2986, 2943, 2180, 1606, 1465, 1326, 1284, 1197, 1156, 1105, 1076, 1027, 900, 853, 814, 778, 753, 708, 645 cm$^{-1}$.

Example 9

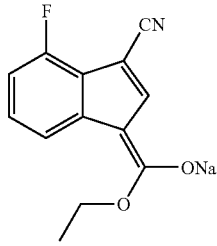

3-(ETHOXY-HYDROXY-METHYLENE)-7-FLUORO-3H-INDENE-1-CARBONITRILE, SODIUM SALT

A solution of tricyclohexylphosphine (248 mg, 0.880 mmol) in ethylene glycol dimethyl ether (5 mL) under nitrogen was charged with palladium (II) acetate (132 mg, 0.590 mmol). The reaction was stirred at room temperature until the solution was homogenous (approx. 15 minutes), cooled to 0° C. and charged with sodium tert-butoxide (1.46 g, 14.7 mmol). After 5 minutes a solution of 2-chloro-6-fluorophenylacetonitrile (1.00 g, 5.90 mmol) and ethyl-3-ethoxyacrylate (877 μL, 5.90 mmol) in ethylene glycol dimethyl ether (5 ml) was added dropwise over 5 minutes. Upon complete addition the reaction was warmed to room temperature and then heated to 60° C. for 17 hours. The reaction was cooled to room temperature then diluted with methyl tert-butyl ether (30 mL) and poured into aqueous potassium dihydrogenphosphate (0.25 M, 40 mL), pH=7. The aqueous layer was separted then saturated by addition of solid sodium chloride and extracted with ethyl acetate (1×40 mL). The organic layer was separated and washed with aqueous saturated sodium chloride (2×25 mL), dried over sodium sulfate, filtered and concentrated in vacuo affording 3-(ethoxy-hydroxy-methylene)-7-fluoro-3H-indene-1-carbonitrile, sodium salt, as a light orange oil (1.21 g, 4.8 mmol, 81%) which solidifies on standing. Trituration in CH$_2$Cl$_2$ (10 ml) for 2 hours and filtering afforded 3-(ethoxy-hydroxy-methylene)-7-fluoro-3H-indene-1-carbonitrile, sodium salt, as a white solid (1.09 g, 4.4 mmol, 74%). $^1$H NMR (400 MHz, CD$_3$CN) δ 7.81 (d, 1H, J=7.9), 7.46 (s, 1H), 6.82 (q, 1H, J=2.5), 6.52 (dd, 1H, J=7.5, 11.2), 4.20 (q, 2H, J=7.5), 1.32 (t, 3H, J=7.1); $^{13}$C NMR (100 MHz, d$_4$-MeOH) 167.8, 156.3, 135.8, 132.8, 123.5, 122.3, 119.3, 116.2, 104.0, 102.8, 75.5, 58.6, 14.0; IR (ATR, neat) 2194, 1628, 1546, 1484, 1462, 1238, 1219, 1095, 1019, 925, 788, 737 cm$^{-1}$.

Example 10

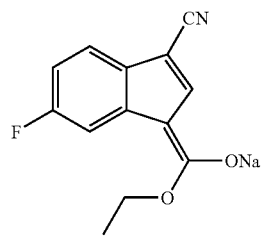

3-(ETHOXY-HYDROXY-METHYLENE)-5-FLUORO-3H-INDENE-1-CARBONITRILE, SODIUM SALT

A solution of tricyclohexylphosphine (248 mg, 0.880 mmol) in ethylene glycol dimethyl ether (5 mL) under nitrogen was charged with palladium (II) acetate (132 mg, 0.590 mmol). The reaction was stirred at room temperature until the solution was homogenous (approx. 15 minutes), cooled to 0° C. and charged with sodium tert-butoxide (1.46 g, 14.7 mmol). After 5 minutes a solution of 2-chloro-6-fluorophenylacetonitrile (1.00 g, 5.90 mmol) and ethyl-3-ethoxyacrylate (877 μL, 5.90 mmol) in ethylene glycol dimethyl ether (5 ml) was added dropwise over 5 minutes. Upon complete addition the reaction was warmed to room temperature and then heated to 60° C. for 16 hours. The reaction was cooled to room temperature then diluted with methyl tert-butyl ether (30 mL) and poured into aqueous potassium dihydrogenphosphate (0.25 M, 40 mL), pH=7. The aqueous layer was separated then saturated by addition of solid sodium chloride and extracted with ethyl acetate (1×40 mL). The organic layer was separated and washed with aqueous saturated sodium chloride (2×25 mL), dried over sodium sulfate, filtered and concentrated in vacuo affording 3-(ethoxy-hydroxy-methylene)-5-fluoro-3H-indene-1-carbonitrile, sodium salt, as a light orange oil (1.29 g, 5.1 mmol, 86%) which solidifies on standing. Trituration in CH$_2$Cl$_2$ (10 ml) for 3 hours and filtering afforded 3-(ethoxy-hydroxy-methylene)-5-fluoro-3H-indene-1-carbonitrile, sodium salt, as a yellow-white solid (1.21 g, 4.8 mmol, 82%). $^1$H NMR (400 MHz, d$_4$-MeOH) δ 7.63 (dd, 1H, J=2.5, 11.4), 7.60 (s, 1H), 7.32 (dd, 1H, J=5.2, 8.5), 6.67

(dt, 1H, J=2.5, 7.1), 4.26 (q, 2H, J=7.1), 1.38 (t, 3H, J=7.1); $^{13}$C NMR (100 MHz, d$_4$-MeOH) 168.1, 159.2, 132.65, 131.92, 122.92, 117.7, 112.5, 106.4, 105.2, 102.8, 79.8, 58.7, 14.1. IR (ATR, neat) 2179, 1602, 1558, 1465, 1250, 1196, 1108, 1061, 1026, 775 cm$^{-1}$; mp 250–260° C.

Example 11

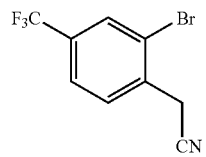

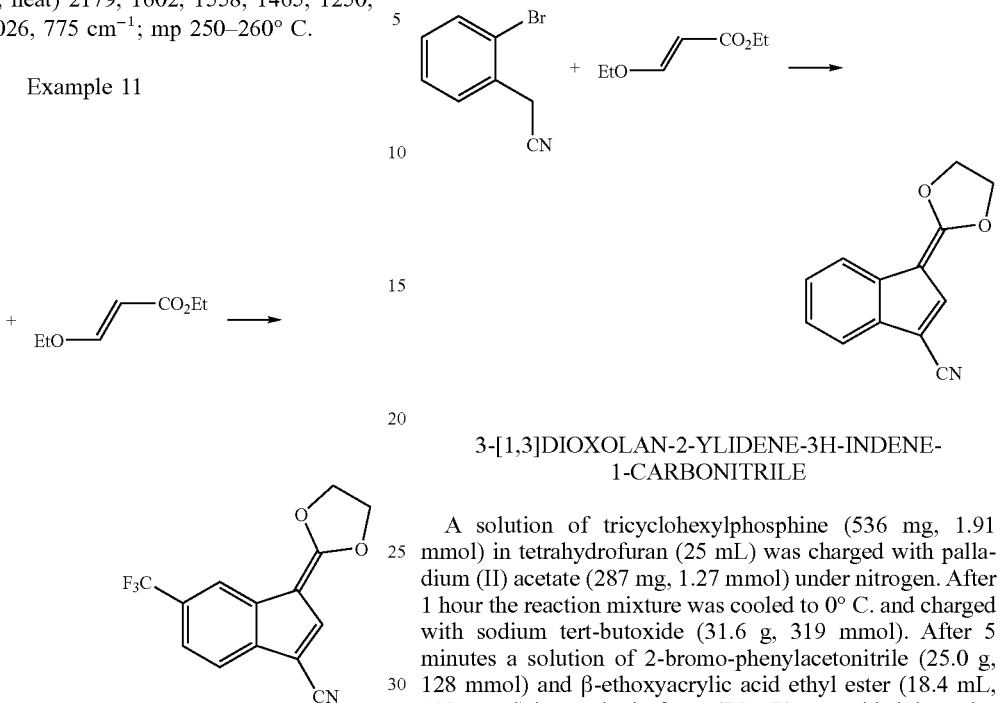

3-[1,3]DIOXOLAN-2-YLIDENE-5-TRIFLUO-ROMETHYL-3H-INDENE-1-CARBONITRILE

A solution of palladium (II) acetate (79.2 mg, 0.353 mmol), and tricyclohexylphosphine (148 mg, 0.527 mmol) in tetrahydrofuran (5 mL) was stirred for 30 minutes at room temperature under a nitrogen atmosphere and then sodium tert-butoxide (1.69 g, 17.5 mmol) was added. The reaction mixture was cooled to 0° C. and a solution of 2-bromo-4-trifluoromethyl-phenyl)-acetonitrile (2.00 g, 7.04 mmol) and ethyl 3-ethoxyacrylate (1.12 g, 7.77 mmol) in tetrahydrofuran (5 mL) was added dropwise. Once addition was complete the reaction mixture was allowed to warm to room temperature and stir for 4½ hours. The reaction was then heated to 60° C. for 18 hours. The reaction was cooled to room temperature and ethylene glycol (20 mL) was added followed by dropwise addition of concentrated sulfuric acid (3 mL). After stirring the reaction mixture over night the product had precipitated from solution. The reaction mixture was filtered to isolate the solid and the solid was triturated with 15 mL of toluene (to remove color). Obtained 3-[1,3] dioxolan-2-ylidene-5-trifluoromethyl-3H-indene-1-carbonitrile as a pale yellow solid (1.22 g, 62%). $^1$HNMR (400 MHz, CD$_3$CN) δ 8.15 (d, 1H, J=0.9), 7.90 (s, 1H), 7.75 (d, 1H, J=8.1), 7.57 (dd, 1H, J=8.1, 0.9), 5.06–5.00 (m, 2H), 4.94–4.88 (m, 2H); $^{13}$C NMR (100 MHz, d$_8$-THF) 169.5, 141.4, 138.5, 134.6, 127.5 (q, J=271), 127.4 (q, J=31.6), 121.6 (q, J=3.8), 121.3, 119.1 (q, J=4.1), 117.9, 100.8, 94.6, 72.6, 71.4; IR (ATR, neat) 2205, 1605, 1330, 1268, 1235, 1216, 1161, 1101, 1065, 1015, 985, 914, 859, 828, 704, 639, 545, 531 cm$^{-1}$.

Example 12

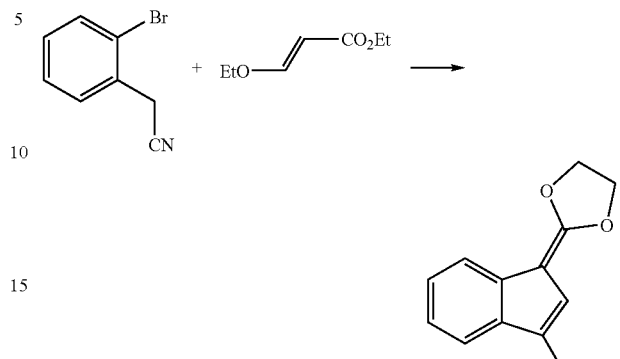

3-[1,3]DIOXOLAN-2-YLIDENE-3H-INDENE-1-CARBONITRILE

A solution of tricyclohexylphosphine (536 mg, 1.91 mmol) in tetrahydrofuran (25 mL) was charged with palladium (II) acetate (287 mg, 1.27 mmol) under nitrogen. After 1 hour the reaction mixture was cooled to 0° C. and charged with sodium tert-butoxide (31.6 g, 319 mmol). After 5 minutes a solution of 2-bromo-phenylacetonitrile (25.0 g, 128 mmol) and β-ethoxyacrylic acid ethyl ester (18.4 mL, 128 mmol) in tetrahydrofuran (75 mL) was added dropwise over 15 minutes. The reaction was heated to 60° C. After 2 hours 30 minutes the reaction mixture was cooled to room temperature and charged with ethylene glycol (200 mL) over 5 minutes and then charged with sulfuric acid (18.8 M, 36 mL) added dropwise over 15 minutes. After 15 hours the reaction was diluted with water (90 ml) and a solid product was filtered through a glass frit. The solid was dried under vacuum affording 3-[1,3]dioxolan-2-ylidene-3H-indene-1-carbonitrile (21.6 g, 102 mmol, 80%) as a light tan solid. The crude material was slurried in isopropanol (50 mL) for 2 hours, filtered and dried under vacuum affording 3-[1,3] dioxolan-2-ylidene-3H-indene-1-carbonitrile (20.8 g, 98.5 mmol, 77%) as a light tan solid. $^1$H NMR (400 MHz, d$_6$-DMSO) δ 7.75 (s, 1H), 7.74 (d, 1H, J=7.9), 7.50 (d, 1H, J=7.1), 7.22 (m, 2H), 4.97 (t, 2H, J=7.8), 4.85 (t, 2H, J=7.8); $^{13}$C NMR (100 MHz, d$_6$-DMSO) 167.4, 136.7, 135.7, 133.1, 124.7, 123.9, 121.1, 119.4, 118.1, 97.8, 92.7, 71.1, 69.9; mp (decomposition) 228° C.

Example 13

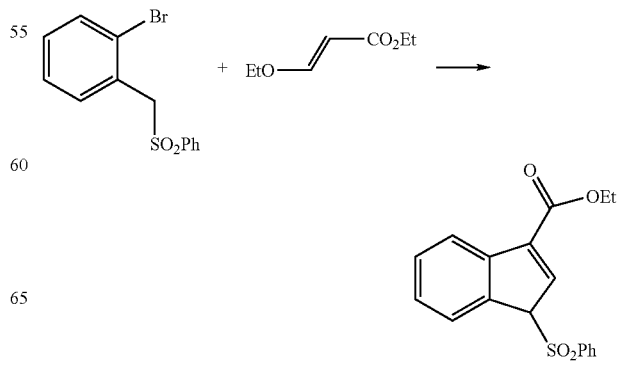

3-BENZENESULFONYL-3H-INDENE-1-CARBOXYLIC ACID ETHYL ESTER

A solution of tricyclohexylphophine (46 mg, 0.164 mmol) in tetrahydrofuran (2.5 mL) under nitrogen was charged with palladium (II) acetate (24.5 mg, 0.109 mmol). The reaction mixture was stirred for 45 minutes, then cooled to 0° C. and charged with sodium tert-butoxide (270 mg, 2.73 mmol). After 5 minutes a solution of β-ethoxyacrylic acid ethyl ester (158 μL, 1.09 mmol) and 2-bromobenzyl phenyl sulfone (340 mg, 1.09 mmol) in tetrahydrofuran (2.5 mL) was added dropwise over 2 minutes. Upon complete addition the reaction was warmed to room temperature and then heated to 60° C. for 2 hours. The reaction was cooled to room temperature, then diluted with methyl tert-butyl ether (25 mL) and poured into aqueous potassium dihydrogen phosphate (0.25 M, 25 mL), pH=7. The aqueous layer was separated and saturated by addition of solid sodium chloride and extracted with ethyl acetate (2×50 mL). The organic layer was separated and washed twice with aqueous saturated sodium chloride (2×30 mL), dried over sodium sulfate, filtered and concentrated in vacuo affording 3-benzenesulfonyl-3H-indene-1-carboxylic acid ethyl ester as a light orange oil (304 mg, 0.925 mmol, 85%). $^1$H NMR (400 MHz, CDCl$_3$) δ 7.88–7.86 (m, 1H), 7.75–7.72 (m, 1H), 7.49–7.43 (m, 3H), 7.36–7.32 (m, 2H), 7.27–7.25 (m, 3H), 5.15 (d, 1H, J=2.1), 4.27 (q, 2H, J=7.1), 1.34 (t, 3H, J=7.1); IR (ATR, neat) 1709, 1649, 1463, 1444, 1314, 1271, 1247, 1188, 1133, 1081, 1044, 773, 752, 722, 686, 575, 528.

Example 14

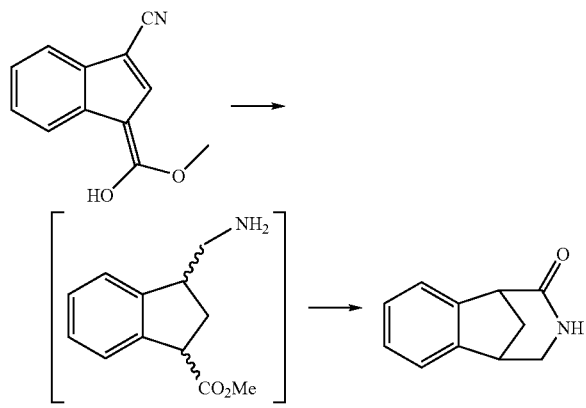

2,3,4,5-TETRAHYDRO-1,5-METHANO-2-OXO-1H-3-BENZAZEPINE

A solution of 3-cyano-1H-indene-1-carboxylic acid methyl ester (6.40 g, 32.2 mmol) in MeOH (30 mL) in a pressure reactor was purged with nitrogen for 5 minutes and charged with 5% palladium on carbon (6.84 g, 1.61 mmol) and concentrated sulfuric acid (3.57 mL, 64.3 mmol). The pressure reactor was purged with nitrogen and evacuated three times, then purged with hydrogen and evacuated three times before charging the bomb with hydrogen to a pressure of 50 psi (3.4 atmospheres) and mechanically shaking. After 5 minutes the hydrogen pressure decreased to 15 psi (approximately 1 atmosphere), and the reaction vessel was charged with hydrogen to increase pressure to 50 psi (3.4 atmospheres). After 16 hours the reactor was evacuated and purged with nitrogen three times before filtering the reaction mixture through a nylon disk. Methanol was displaced by isopropanol and stripped to dryness three times with isopropanol to remove water. The concentrated solution was dissolved in anhydrous methanol and charged with sodium tert-butoxide (15.9 g, 161 mmol) at 0° C. and the suspension was stirred under nitrogen while gradually warming to room temperature. After 24 hours at room temperature, the reaction mixture was concentrated in vacuo and the resultant solid dissolved in ethyl acetate (60 mL) and quenched with 0.5 M aqueous potassium dihydrogen phosphate (100 mL). The organic layer was washed with a saturated aqueous solution of sodium chloride (2×125 mL) and dried over anhydrous sodium sulfate. The organic solution was concentrated in vacuo affording 2,3,4,5-tetrahydro-1,5-methano-2-oxo-1H-3-benzazepine as a brown solid (4.02 g, 72%). $^1$H NMR (400 MHz, CDCl$_3$): δ 7.33 (d, 1H, J=7.6), 7.31 (d, 1H, J=7.6), 7.22 (t, 1H, J=7.6), 7.18 (t, 1H, J=7.6), 5.62 (s, 1H), 3.68 (dd, 1H, J=11.2, 4.1), 3.55 (d, 1H, J=3.7), 3.43–3.37 (m, 1H), 3.18 (d, 1H, J=11.2), 2.52–2.45 (m, 1H), 2.32 (d, 1H, J=11.2); $^{13}$C NMR (100 MHz, CDCl$_3$): δ 173.6, 144.7, 144.6, 128.0, 127.7, 123.2, 122.9, 49.3, 47.9, 39.1, 38.4; IR (neat) 3218, 2949, 2872, 1666, 1485, 1459, 1400, 1328, 1303, 1288, 1250, 1215, 1122, 1104, 1045, 1004, 946, 910, 756, 730, 643, 613 cm$^{-1}$.

Example 15

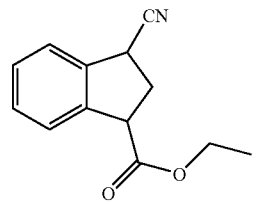

3-CYANO-INDAN-1-CARBOXYLIC ACID ETHYL ESTER

A solution of 3-(ethoxy-hydroxy-methylene)-3H-indene-1-carbonitrile, sodium salt, (1.00 g, 4.70 mmol) in ethanol (40 mL) in a pressure reactor was purged with nitrogen for 5 minutes and charged with 5% palladium on carbon (1.00 g, 0.230 mmol) and formic acid (0.180 mL, 4.70 mmol), pH=5 at reaction initiation. The pressure reactor was purged with nitrogen and evacuated three times, then purged with hydrogen and evacuated three times before charging the bomb with hydrogen at a pressure of 50 psi (3.4 atmospheres) and mechanically shaking. After 2 hours the reactor was evacuated and purged with nitrogen three times before filtering the reaction mixture through a nylon disk. Azeotropic removal of formic acid in vacuo with ethanol and concentrating in vacuo afforded 3-cyano-indan-1-carboxylic acid ethyl ester as a light yellow solid (880 mg, 87%). $^1$H NMR (400 MHz, CD$_3$CN) δ 7.47–7.45 (m, 2H), 7.37–7.35 (m, 2H), 4.28 (t, 1H, J=8.0), 4.20 (m, 2H), 4.16 (t, 1H, J=3), 2.80 (m, 1H), 2.60 (m, 1H), 1.27 (t, 3H, J=7.2); $^{13}$C NMR (100 MHz, CD$_3$CN) δ 172.3, 140.8, 138.5, 129.0, 128.7, 125.4, 124.7, 117.6, 61.3, 48.9, 33.4, 33.3, 13.8; $^{13}$C NMR (100 MHz, d$_4$-MeOH) δ 172.6, 140.4, 138.1, 129.0, 128.8, 125.4, 124.7, 120.9, 61.4, 48.9, 33.2, 33.1, 13.4; IR (ATR, neat) 1732, 1478, 1457, 1370, 1324, 1263, 1208, 1180, 1035, 747.

Example 16

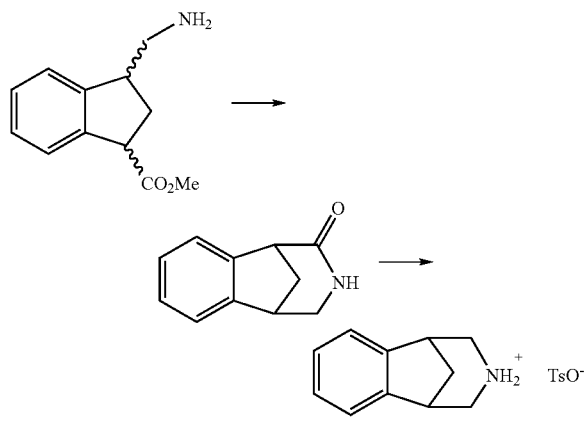

10-AZA-TRICYCLO[6.3.1.0$^{2,7}$]DODECA-2(7),3,5-TRIENE TOSYLATE

A) 9-Oxo-10-aza-tricyclo[6.3.1.0$^{2,7}$]dodeca-2(7),3,5-triene

To a solution of 3-aminomethyl-indan-1-carboxylic acid methyl ester (assume 20.0 mmol, 1 equivalent) in 50 mL of methanol was added 3.84 g of sodium tert-butoxide (40.0 mmol, 2.0 equivalent). The reaction mixture was heated to a reflux for 2 hours. The reaction was cooled to room temperature and concentrated in vacuo. The residue was partitioned between 60 mL of ethyl acetate and 40 mL of 5% aqueous solution of sodium bicarbonate. *The aqueous layer was extracted twice more with 50 mL of ethyl acetate. The combined organic layers were dried over anhydrous sodium sulfate and concentrated to provide a solid material. Recrystallization of the solid from 10 mL of toluene provided white crystals of the title compound (1.78 g, 51%). mp=172–173° C.; $^1$H NMR (400 MHz, CDCl$_3$): δ 7.33 (d, J=7.6 Hz, 1H), 7.31 (d, J=7.6 Hz, 1H), 7.22 (t, J=7.6 Hz, 1H), 7.18 (t, J=7.6 Hz, 1H), 5.62 (s, 1H), 3.68 (dd, J=11.2, 4.1 Hz, 1H), 3.55 (d, J=3.7 Hz, 1H), 3.43–3.37 (m, 1H), 3.18 (d, J=11.2 Hz, 1H), 2.52–2.45 (m, 1H), 2.32 (d, J=11.2 Hz, 1H); $^{13}$C NMR (100 MHz, CDCl$_3$): δ 173.6, 144.7, 144.6, 128.0, 127.7, 123.2, 122.9, 49.3, 47.9, 39.1, 38.4; IR (neat, cm$^{-1}$): 3218, 2949, 2872, 1666, 1485, 1459, 1400, 1328, 1303, 1288, 1250, 1215, 1122, 1104, 1045, 1004, 946, 910, 756, 730, 643, 613; Anal. Calcd for C$_{11}$H$_{21}$NO: C, 76.28; H, 6.40; N, 8.09; Found: C, 75.94; H, 6.27; N, 7.99.

B) 10-Aza-tricyclo[6.3.1.0$^{2,7}$]dodeca-2(7),3,5-triene tosylate

To a solution of 1.38 g of 9-oxo-10-aza-tricyclo [6.3.1.0$^{2,7}$]dodeca-2(7),3,5-triene (8.00 mmol, 1 equivalent) in 8 mL of tetrahydrofuran was added 603 mg of sodium borohydride (16.0 mmol, 2.0 equivalent) followed by slow addition of 2.77 mL of boron trifluoride diethyl etherate (21.6 mmol, 2.7 equivalent). Once the effervescence subsided, the reaction mixture was heated to 50° C. for 5 hours. The reaction was then cooled to room temperature for addition of 10 mL of methanol (added dropwise at first) and 0.125 mL of concentrated hydrochloric acid. Heating was resumed at a reflux for 12 hours. The reaction mixture was then cooled to room temperature and concentrated in vacuo. The residue was diluted with 20 mL of 20% aqueous sodium hydroxide followed by 30 mL of methyl-tert-butyl ether. The mixture was stirred for 30 minutes and then the aqueous layer was extracted with another 30 mL of methyl-tert-butyl ether. The combined organic layers were washed with 40 mL of a saturated aqueous sodium chloride solution and dried over anhydrous sodium sulfate. After concentrating in vacuo, 1.67 g of p-toluenesulfonic acid monohydrate (8.80 mmol, 1.1 equivalent) was added with 20 mL of isopropanol. The solution was heated until homogeneous and then allowed to gradually cool to room temperature with stirring. White crystals of the title compound formed and were collected by filtration (2.17 g, 81%). mp: 207–208° C.; $^1$H NMR (400 MHz, CD$_3$OD): δ 7.69 (d, J=7.9 Hz, 2H), 7.43–7.32 (m, 4H), 7.23 (d, J=7.9 Hz, 2H), 3.37 (d, J=11.2 Hz, 4H), 3.30 (bs, 2H), 3.15 (d, J=12.4 Hz, 2H), 2.36 (s, 3H), 2.40–2.35 (m, 1H), 2.08 (d, J=11.2 Hz, 1H); $^{13}$C NMR (100 MHz, CD$_3$OD): δ 140.8, 140.5, 139.1, 127.2, 127.2, 124.3, 122.3, 45.1, 39.7, 37.3, 18.7; IR (KBr, cm$^{-1}$): 3438, 3021, 2958, 2822, 2758, 2719, 2683, 2611, 2424, 1925, 1606, 1497, 1473, 1428, 1339, 1302, 1259, 1228, 1219, 1176, 1160, 1137, 1122, 1087, 1078, 945, 914, 876, 847, 829, 818, 801, 710, 492; Anal. Calcd for C$_{18}$H$_{21}$NO$_3$S: C, 65.23; H, 6.39; N, 4.23; Found: C, 65.05; H, 6.48; N, 4.26.

Example 17

4-NITRO-10-AZATRICYCLO[6.3.1.0$^{2,7}$]DODECA-2(7),3,5-TRIENE HYDROCHLORIDE

A) 1-(10-Aza-tricyclo[6.3.1.0$^{2,7}$]dodeca-2(7),3,5-trien-10-yl)-2,2,2-trifluoro-ethanone 10-Aza-tricyclo[6.3.1.0$^{2,7}$]dodeca-2(7),3,5-triene hydrochloride salt (12.4 g, 63.9 mmol) was stirred in CH$_2$Cl$_2$ (200 mL). This was cooled (ice bath) and treated with pyridine (12.65 g, 160 mmol) followed by trifluoroacetic anhydride (TFAA) (16.8 g, 11.3 mL, 80 mmol) from an addition funnel over 10 minutes. After ~3 hours, the solution was poured into 0.5N aqueous HCl (200 mL) and the layers separated. The aqueous layer was extracted with CH$_2$Cl$_2$ (3×50 mL) and the combined organic layer was washed with 0.5N aqueous HCl (50 mL), H$_2$O (2×50 mL) and saturated aqueous NaHCO$_3$ solution (50 mL). This solution was dried through a cotton plug, then diluted with ~3% ethyl acetate and filtered through a 2 inch Silica pad eluted with ~3% ethyl acetate/CH$_2$Cl$_2$. Concentration afforded a clear oil which crystallized to give white needles (15.35 g, 60.2 mmol, 94%). (TLC 30% ethyl acetate/hexanes R$_f$ 0.53). $^1$H NMR (400 MHz, CDCl$_3$ δ7.18 (m, 4H), 4.29 (br d, J=12.6 Hz, 1H), 3.84 (br d, J=12.6 Hz, 1H), 3.51 (dd, J=12.6, 1.5 Hz, 1H), 3.21 (br s, 1H), 3.10 (br s, 1H), 3.10 (br d, J=12.6 Hz, 1H), 2.37 (m, 1H), 1.92 (d, J=10.8 Hz, 1H). GCMS m/e 255 (M$^+$). M.p. 67–68° C.

B) 1-(4-Nitro-10-aza-tricyclo[6.3.1.0$^{2,7}$]dodeca-2(7),3,5-trien-10-yl)-2,2,2-trifluoro-ethanone (Based on the method described by Coon, C. L.; Blucher, W. G.; Hill, M. E. *J. Org. Chem.* 1973, 25, 4243.) To a solution of trifluoromethanesulfonic acid (2.4 ml, 13.7 mmol) in CH$_2$Cl$_2$ (10 ml) stirred at 0° C. was slowly added nitric acid (0.58 ml, 27.4 mmol) generating a white precipitate. After 10 minutes the resulting mixture was cooled to −78° C. and treated with 1-(10-aza-tricyclo[6.3.1.0$^{2,7}$]dodeca-2(7),3,5-trien-10-yl)-2,2,2-trifluoro-ethanone (3.5 g, 13.7 mmol) in CH$_2$Cl$_2$ (15 ml) dropwise from an addition funnel over 5 minutes. The reaction was stirred at −78° C. for 30 minutes then warmed to 0° C. for 1 hour. The reaction mixture was poured into a vigorously stirred ice (100 g). The layers were separated and the aqueous layer extracted with CH$_2$Cl$_2$ (3×30 ml). The organic layer was combined and washed with H$_2$O (3×30 ml). The combined organic layer was washed with saturated aqueous NaHCO$_3$ solution (20 mL) and H$_2$O (20 mL) then dried through a cotton plug and concentrated to give an orange oil that solidified on standing (4.2 g). Chromatography yielded pure product as a crystalline solid (3.2 g, 78%). (TLC 30% ethyl acetate/hexanes R$_f$ 0.23). $^1$H NMR (400 MHz, CDCl$_3$ δ8.12 (br d, J=8.0 Hz, 1H), 8.08 (br s, 1H), 7.37 (br d, J=8.0 Hz, 1H), 4.38 (br d, J=12.6 Hz, 1H), 3.94 (br d, J=12.6 Hz, 1H), 3.59 (br d, J=12.6 Hz, 1H), 3.43–3.35 (m, 2H), 3.18 (br d, J=12.6 Hz, 1H), 2.48 (m, 1H), 2.07 (d, J=10.8 Hz, 1H). GCMS m/e 300 (M$^+$).

C) 4-Nitro-10-azatricyclo[6.3.1.0$^{2,7}$]dodeca-2(7),3, 5-triene hydrochloride 1-(4-Nitro-10-aza-tricyclo[6.3.1.0$^{2,7}$]dodeca-2(7),3,5-trien-10-yl)-2,2,2-trifluoro-ethanone (182 mg, 0.61 mmol) was stirred with Na$_2$CO$_3$ (160 mg, 1.21 mmol) in methanol (3 mL) and H$_2$O (1 mL) at 70° C. for 18 hours. The mixture was concentrated, water was added and the product was extracted with CH$_2$Cl$_2$. The organic layer was extracted with 1N aqueous HCl (3×20 mL) and the acidic layer washed with CH$_2$Cl$_2$ (2×20 mL). The aqueous layer was basified to pH ~10 with Na$_2$CO$_3$(s) and product was extracted with CH$_2$Cl$_2$ (3×30 mL). The organic layer was dried through a cotton plug and concentrated to an oil. This was dissolved in methanol and treated with 1N HCl in methanol, concentrated to solids which were recrystallized from methanol/ Et$_2$O to afford product as a white solid (73 mg, 50%). (TLC 5% methanol/CH$_2$Cl$_2$ (NH$_3$) R$_f$ 0.38). $^1$H NMR (400 MHz, DMSO-d$_6$ δ8.21 (s, 1H), 8.18 (dd, J=8.0, 2.0 Hz, 1H), 7.59 (d, J=8.0 Hz, 1H), 3.43 (br s, 2H), 3.28 (m, 2H), 3.07 (dd, J=13.0, 13.0 Hz, 2H), 2.24 (m, 1H), 2.08 (d, J=11.5 Hz, 1H). APCI MS m/e 205.1 [(M+1)$^+$] M.p. 265–270° C.

Example 18

4-AMINO-10-AZATRICYCLO[6.3.1.0$^{2,7}$] DODECA-2(7),3,5-TRIENE HYDROCHLORIDE

4-Nitro-10-azatricyclo[6.3.1.0$^{2,7}$]dodeca-2(7),3,5-triene (500 mg, 2.08 mmol) was stirred in 1,4-dioxane (40 mL) and treated with saturated aqueous Na$_2$CO$_3$ solution (15 mL). To this was added di-t-butyldicarbonate (1.8 g, 8.31 mmol). After stirring 18 hours the reaction was treated with H$_2$O (50 mL), extracted with CH$_2$Cl$_2$ (4×30 mL), dried through a cotton plug and concentrated to provide an oil (500 mg, 91%).

This oil (500 mg, 1.64 mmol) was dissolved in methanol (30 mL), treated with 10% Pd/C (~50 mg) and hydrogenated under a hydrogen atmosphere (45 psi, or approximately 3 atmospheres) for 1 hour. The mixture was filtered through a Celite pad and concentrated to a clear oil (397 mg, 88%).

This oil (50 mg, 0.18 mmol) was stirred in 3N HCl in ethyl acetate (3 mL) for 2 hours then concentrated to a white solid (25 mg, 56%). $^1$H NMR (400 MHz, DMSO-d$_6$)δ7.38–7.10 (3H), 3.60 (br s, 2H), 3.25 (m, 2H), 2.98 (m, 2H), 2.18 (m, 1H), 1.98 (d, J=11.5 Hz, 1H). APCI MS m/e 175.1 [(M+1)$^+$] M.p. 189–192° C.

Example 19

N$^1$-[10-AZATRICYCLO[6.3.1.0$^{2,7}$]DODECA-2(7), 3,5-TRIEN-4-YL]-ACETAMIDE HYDROCHLORIDE

A) 1-(4-Amino-10-aza-tricyclo[6.3.1.0$^{2,7}$]dodeca-2 (7),3,5-trien-10-yl)-2,2,2-trifluoro-ethanone Hydrogenation of 1-(4-nitro-10-aza-tricyclo[6.3.1.0$^{2,7}$] dodeca-2(7),3,5-trien-10-yl)-2,2,2-trifluoro-ethanone (2.0 g, 6.66 mmol) under a hydrogen atmosphere (40 psi, or approximately 2.7 atmospheres) and 10% Pd/C (200 mg) in methanol over 1.5 hours, filtration through Celite and concentration affords a yellow oil (1.7 g). (TLC 50% ethyl acetate/hexanes R$_f$ 0.27). $^1$H NMR (400 MHz, CDCl$_3$)δ6.99 (m, 1H), 6.64 (br s, 1H), 6.57 (m, 1H), 4.25 (m, 1H), 3.82 (m, 1H), 3.50 (m, 1H), 3.17–3.07 (m, 3H), 2.35 (m, 1H), 1.90 (d, J=10.8 Hz, 1H). GCMS m/e 270 (M$^+$).

B) N-(10-Trifluoroacetyl-10-aza-tricyclo[6.3.1.0$^{2,7}$] dodeca-2(7),3,5-trien-4-yl)-acetamide 1-(4-Amino-10-aza-tricyclo[6.3.1.0$^{2,7}$]dodeca-2(7),3,5-trien-10-yl)-2,2,2-trifluoro-ethanone (850 mg, 3.14 mmol) was stirred in CH$_2$Cl$_2$ (5 mL) and treated with triethyl amine (0.53 mL, 3.76 mmol) and acetyl chloride (0.23 mL, 3.2 mmol) then stirred 18 hours. Standard NaHCO$_3$ work-up yielded an oil which was chromatographed to provide a clear oil (850 mg, 87%). (50% ethyl acetate/hexanes R$_f$ 0.28).

C) N$^1$-[10-Azatricyclo[6.3.1.0$^{2,7}$]dodeca-2(7),3,5-trien-4-yl]acetamide hydrochloride N-(10-Trifluoroacetyl-10-aza-tricyclo[6.3.1.0$^{2,7}$]dodeca-2(7),3,5-trien-4-yl)-acetamide (100 mg, 0.32 mmol) was stirred with Na$_2$CO$_3$ (70 mg, 0.64 mmol) in methanol (10 mL) and H$_2$O (2 mL) at 70° C. for 18 hours. The mixture was concentrated, water was added and the product was extracted with ethyl acetate. The organic layer was extracted with 1N aqueous HCl (3×20 mL) and the acidic layer washed with ethyl acetate (2×20 mL). The aqueous layer was basified to pH ~10 with Na$_2$CO$_3$ (s) and product was extracted with ethyl acetate (3×20 mL). The organic layer was dried (sodium sulfate (Na$_2$SO$_4$)) and concentrated to an oil. This material was dissolved in methanol and treated with 3N HCl ethyl acetate (3 mL), concentrated and recrystallized from methanol/Et$_2$O to provide a solid (40 mg, 50%). $^1$H NMR (400 MHz, DMSO-d$_6$)δ9.98 (s, 1H), 9.02 (br m, NH), 7.65 (s, 1H), 7.55 (br s, NH), 7.38 (d, J=8.0 Hz, 1H), 7.20 (d, J=8.0 Hz, 1H), 3.33 (m, 4H), 2.96 (m, 2H), 2.13 (m, 1H), 2.00 (s, 3H), 1.96 (d, J=10.5 Hz, 1H). APCI MS m/e 217.2 [(M+1)$^+$]. M.p. 225–230° C.

Example 20

6-METHYL-5-THIA-7,13-DIAZATETRACYCLO [9.3.1.0$^{2,10}$.0$^{4,8}$]PENTADECA-2(10),3,6,8-TETRAENE HYDROCHLORIDE

A) N-(10-Trifluorothioacetyl-10-aza-tricyclo [6.3.1.0$^{2,7}$]dodeca-2(7),3,5-trien-4-yl)-thioacetamide N-(10-Trifluoroacetyl-10-aza-tricyclo[6.3.1.0$^{2,7}$]dodeca-2(7),3,5-trien-4-yl)-acetamide (850 mg, 2.72 mmol) and 2,4-bis(4-methoxyphenyl)-1,3-dithia-2,4-diphosphetane-2, 4-disulfide (Lawesson's reagent) (1.1 g, 2.72 mmol) were combined in toluene (10 mL) and brought to reflux for 1.5 hours. After cooling the reaction was worked up with ethyl acetate/saturated aqueous $NaHCO_3$ solution. The organic layer was dried ($Na_2SO_4$), filtered, concentrated and chromatographed on Silica gel to produce product (410 mg, 44%). (50% ethyl acetate/hexanes $R_f$ 0.38)

B) 6-Methyl-5-thia-7,13-diazatetracyclo [9.3.1.0$^{2,10}$.0$^{4,8}$]pentadeca-2(10),3,6,8-tetraene hydrochloride The above oil, 2,2,2-trifluoro-N-(10-trifluorothioacetyl-10-aza-tricyclo[6.3.1.0$^{2,7}$]dodeca-2(7),3,5-trien-4-yl)-thioacetamide, (360 mg, 1.05 mmol) was dissolved in methanol (10 mL) and 1N NaOH (5 mL) and added to potassium ferricyanide ($K_3Fe(CN)_6$)(1.72 g, 5.23 mmol) in $H_2O$ (10 mL). This mixture was warmed to 60° C. for 1.5 hours, cooled, concentrated and worked up with ethyl acetate/$H_2O$. This material was stirred in dioxane (20 mL) and treated with $H_2O$ (50 mL) and $Na_2CO_3$ to achieve pH 10. To this was added di-t-butyldicarbonate (436 mg, 2.0 mmol) and the mixture was stirred for 18 hours. The reaction was concentrated, treated with $H_2O$ and extracted with $CH_2Cl_2$. The product was chromatographed (Silica 30% ethyl acetate/ hexanes $R_f$ 0.41) to yield an oil (100 mg).

The above product was treated with 3N HCl/ethyl acetate (3 mL) and warmed to reflux for ~15 minutes then concentrated to a solid which was azeotroped with $CH_2Cl_2$ (two times). These solids were dissolved in a minimum amount of methanol then saturated with $Et_2O$ and stirred. The resulting white crystalline powder was collected by filtration (40 mg, 14%). $^1$H NMR (400 MHz, DMSO-d$_6$)δ9.46 (s, NH), 7.65 (s, 1H), 7.82 (s, 1H), 7.65 (br m, NH), 3.36 (m, 2H), 3.24 (m, 2H), 3.02 (m, 2H), 2.76 (s, 3H), 2.23 (m, 1H), 2.06 (d, J=10.8 Hz, 1H). APCI MS m/e 231.1 [(M+1)$^+$]. M.p. 183–184° C.

Example 21

4,5-DINITRO-10-AZA-TRICYCLO[6.3.1.0$^{2,7}$] DODECA-2(7),3,5-TRIENE

A) 1-(4,5-Dinitro-10-aza-tricyclo[6.3.1.0$^{2,7}$]dodeca-2(7),3,5-trien-10-yl)-2,2,2-trifluoro-ethanone (Based on the method described in Coon, C. L.; Blucher, W. G.; Hill, M. E. *J. Org. Chem.* 1973, 25, 4243. For an additional related example of dinitration see: Tanida, H.; Ishitobi, H.; Irie, T.; Tsushima, T. *J. Am. Chem. Soc.* 1969, 91, 4512.)

To a solution of trifluoromethanesulfonic acid (79.8 ml, 902.1 mmol) in $CH_2Cl_2$ (550 ml) stirred at 0° C. was slowly added nitric acid (19.1 ml, 450.9 mmol) generating a white precipitate. After 10 minutes, 1-(10-aza-tricyclo[6.3.1.0$^{2,7}$] dodeca-2(7),3,5-trien-10-yl)-2,2,2-trifluoro-ethanone (50 g, 196 mmol) in $CH_2Cl_2$ (300 ml) was added dropwise from an addition funnel over 30 minutes. The reaction was stirred at 0° C. for 2.5 hours and then stirred at room temperature for 24 hours. The reaction mixture was poured into a vigorously stirred mixture of $H_2O$ (500 ml) and ice (400 g). The layers were separated and the aqueous layer back extracted with $CH_2Cl_2$ (3×300 ml). The organic layer was combined and washed with $H_2O$ (3×300 ml). The combined aqueous layers were re-extracted with $CH_2Cl_2$ (2×100 ml). The organic layer was combined and washed with saturated aqueous $NaHCO_3$ solution (200 mL) and $H_2O$ (200 mL) then dried through a cotton plug and concentrated to solids. Trituration with ethyl acetate/hexanes produced off white solids which were filtered and dried (52 g, 151 mmol, 77%. The mother liquor was chromatographed to give an additional 4.0 g for a total of 56.0 g (82.8%). (TLC 50% ethyl acetate/hexanes $R_f$ 0.29) $^1$H NMR (400 MHz, CDCl$_3$)δ7.77 (s, 1H), 7.75 (s, 1H), 4.39 (br d, J=13.0 Hz, 1H), 3.98 (br d, J=13.0 Hz, 1H), 3.65 (d, J=13.0 Hz, 1H), 3.49 (br s, 1H), 3.44 (br s, 1H), 3.24 (br d, J=12.6 Hz, 1H), 2.53 (m, 1H), 2.14 (d, J=11.5 Hz, 1H). GCMS m/e 345 (M$^+$).

B) 4,5-Dinitro-10-aza-tricyclo[6.3.1.0$^{2,7}$]dodeca-2 (7),3,5-triene 1-(4,5-Dinitro-10-aza-tricyclo[6.3.1.0$^{2,7}$]dodeca-2(7),3, 5-trien-10-yl)-2,2,2-trifluoro-ethanone (3.7 g, 10.7 mmol) and $Na_2CO_3$ (2.3 g, 21.4 mmol) were combined in methanol (50 mL) and $H_2O$ (20 mL) then warmed to reflux for 18 hours. The reaction was cooled, concentrated, treated with $H_2O$ and extracted with $CH_2Cl_2$ (3×50 mL) then dried through a cotton plug. After concentration, the residue was chromatographed to provide brown solids. (1.9 g, 71%). (TLC 5% methanol/$CH_2Cl_2$ (NH$_3$) $R_f$ 0.36). $^1$H NMR (400 MHz, CDCl$_3$)δ7.69 (s, 2H), 3.17 (br s, 2H), 3.11 (d, J=12.6 Hz, 2H), 2.53 (m, 1H), 2.07 (d, J=11.0 Hz, 1H). GCMS m/e 249 (M$^+$).

Example 22

6-METHYL-7-PROPYL-5,7,13-TRIAZATETRA-CYCLO[9.3.1.0$^{2,10}$.0$^{4,8}$]-PENTADECA-2(10),3,5,8-TETRAENE HYDROCHLORIDE

A) 4,5-Dinitro-10-aza-tricyclo[6.3.1.0$^{2,7}$]dodeca-2 (7),3,5-triene-10-carboxylic acid tert-butyl ester 4,5-Dinitro-10-aza-tricyclo[6.3.1.0$^{2,7}$]dodeca-2(7),3,5-triene, (1.9 g, 7.6 mmol) was stirred in 1,4-dioxane (75 mL) and treated with saturated aqueous $Na_2CO_3$ solution (10 mL). To this was added di-t-butyldicarbonate (3.31 g, 15.2 mmol). After stirring 6 hours the reaction was treated with $H_2O$ (50 mL) and extracted with ethyl acetate (4×25 mL), dried ($Na_2SO_4$), filtered, concentrated and chromatographed to provide product (1.9 g, 71%). (TLC 30% ethyl acetate/ hexanes (NH$_3$) $R_f$ 0.58). $^1$H NMR (400 MHz, CDCl$_3$)δ7.77 (br s, 1H), 7.72 (br s, 1H), 4.08 (m, 1H), 3.92 (m, 1H), 3.39 (br s, 1H), 3.27 (br s, 1H), 3.25 (m, 1H), 3.18 (m, 1H), 2.46 (m, 1H), 2.02 (d, J=11.0 Hz, 1H).

B) 4,5-Diamino-10-aza-tricyclo[6.3.1.0$^{2,7}$]dodeca-2 (7),3,5-triene-10-carboxylic acid tert-butyl ester 4,5-Dinitro-10-aza-tricyclo[6.3.1.0$^{2,7}$]dodeca-2(7),3,5-triene-10-carboxylic acid tert-butyl ester (1.9 g, 5.44 mmol) was hydrogenated in methanol under a $H_2$ atmosphere (45 psi, or approximately 3 atmospheres) over 10% Pd/C (100 mg) for 1.5 hours then filtered through a Celite pad and concentrated to white solids (1.57 g, 100%). (TLC 5% methanol/$CH_2Cl_2$ (NH$_3$) $R_f$ 0.14).

C) 6-Methyl-5,7,13-triazatetracyclo[9.3.1.0$^{2,10}$.0$^{4,8}$] pentadeca-2(10),3,5,8-tetraene-13-carboxylic acid tert-butyl ester (For conditions, see; Segelstein, B. E.; Chenard, B. L.; Macor, J. E.; Post, R. J. *Tetrahedron Lett.* 1993, 34, 1897.)

4,5-Diamino-10-aza-tricyclo[6.3.1.0$^{2,7}$]dodeca-2(7),3,5-triene-10-carboxylic acid tert-butyl ester (700 mg, 2.42 mmol) was dissolved in ethanol (10 mL) and acetic acid (HOAc) (1 mL) and treated with 1-ethoxyethylenemalononitrile (329 mg, 2.42 mmol). The resulting mixture was warmed to 60° C. and stirred 18 hours. The reaction was cooled, concentrated treated with H$_2$O and saturated aqueous Na$_2$CO$_3$ solution and extracted with ethyl acetate (3×50 mL), then dried (Na$_2$SO$_4$). After filtration and concentration, the residue was chromatographed to provide brown solids (247 mg, 36%). (TLC 5% methanol/CH$_2$Cl$_2$ (NH$_3$) R$_f$ 0.28).

D) 6-Methyl-7-propyl-5,7,13-triazatetracyclo[9.3.1.0$^{2,10}$.0$^{4,8}$]pentadeca-2(10),3,5,8-tetraene-13-carboxylic acid tert-butyl ester (For conditions, see; Pilarski, B. *Liebigs Ann. Chem.* 1983, 1078.) 6-Methyl-5,7,13-triazatetracyclo[9.3.1.0$^{2,10}$.0$^{4,8}$]pentadeca-2(10),3,5,8-tetraene-13-carboxylic acid tert-butyl ester (80 mg, 0.267 mmol) was stirred in 50% aqueous NaOH solution (3 mL) and DMSO (1 mL) then treated with 1-iodopropane (0.03 mL, 0.321 mmol). This mixture was warmed to 40° C. for 2 hours then cooled, treated with H$_2$O and extracted with ethyl acetate. The organic layer was washed with H$_2$O (3 times) then dried (Na$_2$SO$_4$), filtered and concentrated to an oil (90 mg, 0.253 mmol). (TLC 5% methanol/CH$_2$Cl$_2$ (NH$_3$) R$_f$ 0.15).

E) 6-Methyl-7-propyl-5,7,13-triazatetracyclo[9.3.1.0$^{2,10}$.0$^{4,8}$]pentadeca-2(10),3,5,8-tetraene hydrochloride 6-Methyl-7-propyl-5,7,13-triazatetracyclo[9.3.1.0$^{2,10}$.0$^{4,8}$]pentadeca-2(10),3,5,8-tetraene-13-carboxylic acid tert-butyl ester (90 mg, 0.253 mmol) was dissolved in 3N HCl ethyl acetate (5 mL) and warmed to 100° C. for ½ hour. The mixture was cooled, concentrated, slurried in ethyl acetate, and filtered to provide a white solid (25 mg, 34%). $^1$H NMR (400 MHz, DMSO-d$_6$) δ9.56 (s, NH), 7.91 (s, 1H), 7.83 (br m, NH), 7.74 (s, 1H), 4.38 (m, 2H), 3.48 (m, 2H), 3.32 (m, 2H), 3.10 (m, 2H), 2.87 (s, 3H), 2.28 (m, 1H), 2.15 (d, J=11.0 Hz, 1H) 1.85 (m, 2H), 0.97 (m, 3H). M.p. 147–150° C.

Example 23

5,7,13-TRIAZATETRACYCLO[9.3.1.0$^{2,10}$.0$^{4,8}$]-PENTADECA-2(10),3,5,8-TETRAENE HYDROCHLORIDE

A) 5,7,13-Triazatetracyclo[9.3.1.0$^{2,10}$.0$^{4,8}$]pentadeca-2(10),3,5,8-tetraene-13-carboxylic acid tert-butyl ester (For conditions, see; Segelstein, B. E.; Chenard, B. L.; Macor, J. E.; Post, R. J. *Tetrahedron Lett.* 1993, 34, 1897.)

4,5-Diamino-10-aza-tricyclo[6.3.1.0$^{2,7}$]dodeca-2(7),3,5-triene-10-carboxylic acid tert-butyl ester (1.0 g, 3.45 mmol) was dissolved in ethanol (10 mL) and HOAc (1 mL) and treated with ethoxymethylenemalononitrile (421 mg, 3.45 mmol). The resulting mixture was warmed to 60° C. and stirred 18 hours. The reaction was cooled, concentrated treated with H$_2$O and saturated aqueous Na$_2$CO$_3$ solution and extracted with ethyl acetate (3×50 mL), then dried (Na$_2$SO$_4$). After filtration and concentration, the residue was chromatographed to provide brown solids (580 mg, 56%). (TLC 5% methanol/CH$_2$Cl$_2$ (NH$_3$) R$_f$ 0.28)

B) 5,7,13-triazatetracyclo[9.3.1.0$^{2,10}$.0$^{4,8}$]pentadeca-2(10),3,5,8-tetraene hydrochloride 5,7,13-Triazatetracyclo[9.3.1.0$^{2,10}$.0$^{4,8}$]pentadeca-2(10),3,5,8-tetraene-13-carboxylic acid tert-butyl ester was converted to the title compound by the methods described in Example 22E. $^1$H NMR (400 MHz, D$_2$O) δ8.95 (s, 1H), 7.67 (s, 2H), 3.45 (br s, 2H), 3.31 (d, J=12.5 Hz, 2H), 3.13 (d, J=12.5 Hz, 2H), 2.30 (m, 1H), 1.99 (d, J=11.5 Hz, 1H). APCI MS m/e 200.1 [(M+1)$^+$]. M.p. >250° C.

Example 24

7-METHYL-5,7,13-TRIAZATETRACYCLO[9.3.1.0$^{2,10}$.0$^{4,8}$]PENTADECA-2(10),3,5,8-TETRAENE HYDROCHLORIDE

Utilizing the methods described in Example 22D, 5,7,13-triazatetracyclo[9.3.1.0$^{2,10}$.0$^{4,8}$]pentadeca-2(10),3,5,8-tetraene-13-carboxylic acid tert-butyl ester was converted to the title compound by reaction with iodomethane followed by deprotection as described in Example 12E. $^1$H NMR (400 MHz, D$_2$O) δ8.97 (s, 1H), 7.71 (s, 1H), 7.67 (s, 1H), 3.94 (s, 3H), 3.48 (m, 2H), 3.33 (d, J=12.2 Hz, 2H), 3.14 (d, J=12.2 Hz, 2H), 2.34 (m, 1H), 2.03 (d, J=11.5 Hz, 1H). APCI MS m/e 214.2 [(M+1)$^+$].

Example 25

6-METHYL-5,7,13-TRIAZATETRACYCLO[9.3.1.0$^{2,10}$.0$^{4,8}$]-PENTADECA-2(10),3,5,8-TETRAENE HYDROCHLORIDE

6-Methyl-5,7,13-triazatetracyclo[9.3.1.0$^{2,10}$.0$^{4,8}$]pentadeca-2(10),3,5,8-tetraene-13-carboxylic acid tert-butyl ester was converted to the title compound by the methods described in Example 22E. $^1$H NMR (400 MHz, DMSO-d$_6$) δ9.40 (br m, NH), 7.77 (br m, NH), 7.70 (s, 1H), 3.44 (m, 2H), 3.30 (m, 2H), 3.05 (br d, J=11.0 Hz, 2H), 2.79 (s, 3H), 2.23 (m, 1H), 2.10 (d, J=10.8 Hz, 1H). GCMS m/e 213.5 (M$^+$).

Example 26

6,7-DIMETHYL-5,7,13-TRIAZATETRACYCLO[9.3.1.0$^{2,10}$.0$^{4,8}$]-PENTADECA-2(10),3,5,8-TETRAENE HYDROCHLORIDE

Utilizing the methods described in Example 22D, 6-methyl-5,7,13-triazatetracyclo[9.3.1.0$^{2,10}$.0$^{4,8}$]pentadeca-2(10),3,5,8-tetraene-13-carboxylic acid tert-butyl ester was converted to the title compound by reaction with iodomethane followed by deprotection as described in Example 22E. $^1$H NMR (400 MHz, DMSO-d$_6$) δ9.52 (s, NH), 7.84 (s, 1H), 7.82 (br m, NH), 7.72 (s, 1H), 3.90 (s, 3H), 3.45 (m, 2H), 3.28 (m, 2H), 3.04 (m, 2H), 2.82 (s, 3H), 2.23 (m, 1H), 2.12 (d, J=11.0 Hz, 1H). APCI MS m/e 228.2 [(M+1)$^+$]. M.p. 225–230° C.

Example 27

7-PROPYL-5,7,13-TRIAZATETRACYCLO[9.3.1.0$^{2,10}$.0$^{4,8}$]-PENTADECA-2(10),3,5,8-TETRAENE HYDROCHLORIDE

Utilizing the methods described in Example 22D, 5,7,13-triazatetracyclo[9.3.1.0$^{2,10}$.0$^{4,8}$]pentadeca-2(10),3,5,8-tetraene-13-carboxylic acid tert-butyl ester was converted to the title compound by reaction with iodopropane followed by deprotection as described in Example 22E. $^1$H NMR (400 MHz, DMSO-d$_6$)δ9.52 (s, 1H), 9.45 (br s, NH), 7.97 (s, 1H), 7.85 (s, 1H), 7.83 (br m, NH), 4.43 (m, 2H), 3.49 (m, 2H), 3.33 (m, 2H), 3.08 (m, 2H), 2.28 (m, 1H), 2.15 (d, J=11.0 Hz, 1H), 1.92 (m, 2H), 0.93 (m, 3H). APCI MS m/e 242.2 [(M+1)$^+$]. M.p. 170–171° C. (subl.).

Example 28

7-BUTYL-5,7,13-TRIAZATETRACYCLO[9.3.1.0$^{2,10}$.0$^{4,8}$]-PENTADECA-2(10),3,5,8-TETRAENE HYDROCHLORIDE

A) 4-Butylamino-5-nitro-10-aza-tricyclo[6.3.1.0$^{2,7}$]dodeca-2(7),3,5-triene-10-carboxylic acid tert-butyl ester (For conditions, see; Senskey, M. D.; Bradshaw, J. D.; Tessier, C. A.; Youngs, W. J. *Tetrahedron Lett.* 1995, 36, 6217.)
4,5-Dinitro-10-aza-tricyclo[6.3.1.0$^{2,7}$]dodeca-2(7),3,5-triene-10-carboxylic acid tert-butyl ester (500 mg, 1.43 mmol) and 1-butylamine (1.42 mL, 14.3 mmol) were combined in THF (5 mL) and stirred 4 hours. The mixture was diluted with ethyl acetate (50 mL) and washed with H$_2$O (3×30 mL) then dried (Na$_2$SO$_4$), filtered and concentrated to an oil. This oil was passed through a Silica gel filter column to remove baseline impurities eluting with 30% ethyl acetate/hexanes (510 mg, 1.41 mmol, 99%).

B) 4-Butylamino-5-amino-10-aza-tricyclo[6.3.1.0$^{2,7}$]dodeca-2(7),3,5-triene-10-carboxylic acid tert-butyl ester 4-Butylamino-5-nitro-10-aza-tricyclo[6.3.1.0$^{2,7}$]dodeca-2(7),3,5-triene-10-carboxylic acid tert-butyl ester (460 mg, 1.27 mmol) was treated with ammonium formate (850 mg, 12.7 mmol) and 10% Pd(OH)$_2$/C (50 mg) in methanol (20 mL) and brought to reflux for 1 hour then filtered through a Celite pad and concentrated. The solids were treated with saturated aqueous Na$_2$CO$_3$ solution, extracted with CH$_2$Cl$_2$ (3×30 mL) and dried by filtration through a cotton plug to give an oil (440 mg, 100%).

C) 7-Butyl-5,7,13-triazatetracyclo[9.3.1.0$^{2,10}$.0$^{4,8}$]pentadeca-2(10),3,5,8-tetraene-13-carboxylic acid tert-butyl ester 4-Butylamino-5-amino-10-aza-tricyclo[6.3.1.0$^{2,7}$]dodeca-2(7),3,5-triene-10-carboxylic acid tert-butyl ester (440 mg, 1.27 mmol) was dissolved in ethanol (20 mL) and HOAc (2 mL) and treated with ethoxymethylenemalononitrile (186 mg, 1.52 mmol). The resulting mixture was warmed to 60° C. and stirred 18 hours. The reaction was cooled, concentrated, treated with H$_2$O and saturated aqueous Na$_2$CO$_3$ solution then extracted with ethyl acetate (3×50 mL) and dried (Na$_2$SO$_4$). After filtration and concentration, the residue was chromatographed to provide a yellow oil. (400 mg, 89%). (TLC 5% methanol/CH$_2$Cl$_2$ (NH$_3$) R$_f$ 0.70).

D) 7-Butyl-5,7,13-triazatetracyclo[9.3.1.0$^{2,10}$.0$^{4,8}$]pentadeca-2(10),3,5,8-tetraene hydrochloride 7-Butyl-5,7,13-triazatetracyclo[9.3.1.0$^{2,10}$.0$^{4,8}$]pentadeca-2(10),3,5,8-tetraene-13-carboxylic acid tert-butyl ester was converted to the title compound by the methods described in Example 22E. $^1$H NMR (400 MHz, DMSO-d$_6$)δ9.93 (brs, NH), 9.68 (s, 1H), 7.99 (s, 1H), 7.92 (br m, NH), 7.87 (s, 1H), 4.50 (m, 2H), 3.49 (m, 2H), 3.30 (m, 2H), 3.08 (m, 2H), 2.26 (m, 1H), 2.15 (d, J=11.0 Hz, 1H), 1.88 (m, 2H), 1.32 (m, 2H), 0.82 (t, J=7.0 Hz, 3H). APCI MS m/e 256.2 [(M+1)$^+$]. M.p. 204–208° C.

Example 29

7-ISOBUTYL-5,7,13-TRIAZATETRACYCLO[9.3.1.0$^{2,10}$.0$^{4,8}$]-PENTADECA-2(10),3,5,8-TETRAENE HYDROCHLORIDE 4,5-Dinitro-10-aza-tricyclo[6.3.1.0$^{2,7}$]dodeca-2(7),3,5-triene-10-carboxylic acid tert-butyl ester and isobutylamine were converted to the title compound utilizing the methods described in Example 28A–D. $^1$H NMR (400 MHz, CDCl$_3$)δ7.74 (s, 1H), 7.52 (s, 1H), 7.14 (s, 1H), 3.90 (dd, J=7.5,2.0 Hz, 2H), 3.04–2.97 (m, 4H), 2.70 (dd, J=12.8,2.3 Hz, 2H), 2.42 (m, 1H), 2.19 (m, 1H), 1.98 (d, J=10.5 Hz, 1H), 0.93 (m, 6H). APCI MS m/e 256.2 [(M+1)$^+$]. M.p. 147–150° C. (subl.).

Example 30

6-METHYL-7-ISOBUTYL-5,7,13-TRIAZATETRACYCLO[9.3.1.0$^{2,10}$.0$^{4,8}$]-PENTADECA-2(10),3,5,8-TETRAENE HYDROCHLORIDE

A) 6-Methyl-7-isobutyl-5,7,13-triazatetracyclo[9.3.1.0$^{2,10}$.0$^{4,8}$]Pentadeca-2(10),3,5,8-tetraene-13-carboxylic acid tert-butyl ester 4-Amino-5-isobutylamino-10-aza-tricyclo[6.3.1.0$^{2,7}$]dodeca-2(7),3,5-triene-10-carboxylic acid tert-butyl ester (250 mg, 0.74 mmol) from Example 29B was dissolved in ethanol (10 mL) and HOAc (2 mL) and treated with 1-ethoxyethylenemalononitrile (118 mg, 0.87 mmol). The reaction proceeded as in Example 28C (18 h) and was worked up similarly to provide product (TLC 3% methanol/CH$_2$Cl$_2$ (NH$_3$) R$_f$ 0.57).

B) 6-Methyl-7-isobutyl-5,7,13-triazatetracyclo[9.3.1.0$^{2,10}$.0$^{4,8}$]pentadeca-2(10),3,5,8-tetraene hydrochloride 6-Methyl-7-isobutyl-5,7,13-triazatetracyclo[9.3.1.0$^{2,10}$.0$^{4,8}$]pentadeca-2(10),3,5,8-tetraene-13-carboxylic acid tert-butyl ester was converted to the title compound by the methods described in Example 22E. APCI MS m/e 270.3 [(M+1)$^+$]. M.p. 129–130° C. (subl.).

Example 31

7-PHENYL-5,7,13-TRIAZATETRACYCLO [9.3.1.0$^{2,10}$.0$^{4,8}$]-PENTADECA-2(10),3,5,8-TETRAENE HYDROCHLORIDE

Utilizing the methods described in Example 28A, 4,5-dinitro-10-azatricyclo[6.3.1.0$^{2,7}$]dodeca-2(7),3,5-triene-10-carboxylic acid tert-butyl ester and aniline were converted to 4-phenylamino-5-nitro-10-aza-tricyclo[6.3.1.0$^{2,7}$]dodeca-2 (7),3,5-triene-10-carboxylic acid tert-butyl at 75° C. for 4 hours in the coupling step. This was then converted to the title compound utilizing the methods described in Example 28B,C,D. $^1$H NMR (400 MHz, DMSO-d$_6$)δ9.08 (1H), 7.78–7.57 (m, 7H), 3.47–3.00 (m, 6H), 2.23 (m, 1H), 2.09 (d, J=11.5 Hz, 1H). APCI MS m/e 276.2 [(M+1)$^+$]. M.p. 210–213° C.

Example 32

6-METHYL-7-PHENYL-5,7,13-TRIAZATETRACYCLO[9.3.1.0$^{2,10}$.0$^{4,8}$]-PENTADECA-2(10),3,5,8-TETRAENE HYDROCHLORIDE

Utilizing the methods described in Example 31 and Example 30, 4,5-dinitro-10-aza-tricyclo[6.3.1.0$^{2,7}$]dodeca-2 (7),3,5-triene-10-carboxylic acid tert-butyl ester and aniline were converted to the title compound. $^1$H NMR (400 MHz, DMSO-d$_6$)δ7.79 (s, 1H), 7.73–7.56 (m, 5H), 7.32 (s, 1H), 3.46–2.99 (m, 6H), 2.66 (s, 3H), 2.23 (m, 1H), 2.08 (d, J=11.0 Hz, 1H). APCI MS m/e 290.2 [(M+1)$^+$]. M.p. >250° C.

Example 33

7-NEOPENTYL-5,7,13-TRIAZATETRACYCLO [9.3.1.0$^{2,10}$.0$^{4,8}$]-PENTADECA-2(10),3,5,8-TETRAENE HYDROCHLORIDE

Utilizing the methods described in Example 28A-D, 4,5-dinitro-10-aza-tricyclo[6.3.1.0$^{2,7}$]dodeca-2(7),3,5-triene-10-carboxylic acid tert-butyl ester and neopentylamine were converted to the title compound. t-Boc precursor GCMS m/e 369 (M$^+$). (HCl salt) M.p. >250° C.

Example 34

6-METHYL-7-NEOPENTYL-5,7,13-TRIAZATETRACYCLO[9.3.1.0$^{2,10}$.0$^{4,8}$]-PENTADECA-2(10),3, 5,8-TETRAENE HYDROCHLORIDE

Utilizing the methods described in Examples 21 and 20, 4,5-dinitro-10-aza-tricyclo[6.3.1.0$^{2,7}$]dodeca-2(7),3,5-triene-10-carboxylic acid tert-butyl ester and neopentylamine were converted to the title compound. $^1$H NMR (400 MHz, DMSO-d$_6$)δ7.31 (s,1H), 7.27 (s, 1H), 7.02 (br s, NH), 4.41 (t, J=13.0 Hz, 2H), 3.90 (s, 3H), 3.47–3.26 (m, 6H), 2.20 (m, 1H), 2.00 (d, J=11.5 Hz, 1H), 0.90 (s, 9H). t-Boc precursor APCI MS m/e 384.2 [(M+1)$^+$]. M.p. >250° C.

Example 35

6,7-DIMETHYL-5,8,14-TRIAZATETRACYCLO [10.3.1.0$^{2,11}$.0$^{4,9}$]-HEXADECA-2(11),3,5,7,9-PENTAENE HYDROCHLORIDE (Based on the following procedure: Jones, R. G.; McLaughlin, K. C. Org. Syn. 1963, 4, 824. b) Ehrlich, J., Bobert, M. T. J. Org. Chem. 1947, 522.) 4,5-Diamino-10-aza-tricyclo[6.3.1.0$^{2,7}$]dodeca-2(7),3,5-triene-10-carboxylic acid tert-butyl ester (100 mg, 0.35 mmol) was warmed to 80° C. in H$_2$O (5 mL). To this butane 2,3-dione (0.034 mL, 0.38 mmol) was added under N$_2$ for 2 hours. The reaction was cooled to room temperature and extracted with ethyl acetate (3×40 ml). The combined organic layer was washed with H$_2$O (2×30 ml), dried (Na$_2$SO$_4$), filtered, concentrated and chromatographed on Silica gel to provide an oil (120 mg, 100%). The oil was dissolved in 2N HCl methanol (5 mL) and warmed to reflux for 30 minutes, then concentrated. Recrystallization from methanol/Et$_2$O provided a white powder (50 mg, 43%). (TLC ethyl acetate R$_f$ 0.14). $^1$H NMR (400 MHz, DMSO-d$_6$)δ7.85 (s, 2H), 3.50 (br s, 2H), 3.32 (d, J=12.5 Hz, 2H), 3.10 (d, J=12.5 Hz, 2H), 2.64 (s, 6H), 2.24 (m, 1H), 2.13 (d, J=11.0 Hz, 1H). t-Boc precursor APCI MS m/e 340.3 [(M+1)$^+$].

Example 36

5,8,14-TRIAZATETRACYCLO[10.3.1.0$^{2,11}$.0$^{4,9}$]-HEXADECA-2(11),3,5,7,9-PENTAENE HYDROCHLORIDE

A) 1-(4,5-Diamino-10-aza-tricyclo[6.3.1.0$^{2,7}$] dodeca-2(7),3,5-trien-10-yl)-2,2,2-trifluoro-ethanone 1-(4,5-Dinitro-10-aza-tricyclo[6.3.1.0$^{2,7}$]dodeca-2(7),3, 5-trien-10-yl)-2,2,2-trifluoro-ethanone (3.0 g, 8.70 mmol) was hydrogenated in methanol (30 ml) under a hydrogen atmosphere (45 psi, or approximately 3 atmospheres) over Pd(OH)$_2$ (300 mg of 20 wt %/C, 10% wt). After 2.5 hours the reaction was filtered through a Celite pad and rinsed with methanol (30 ml). The solution was concentrated to a light brown oil which crystallized (2.42 g, 96%). (TLC 10% methanol/CH$_2$Cl$_2$ R$_f$ 0.56). APCI MS m/e 286.2 [(M+1)$^+$]. M.p. 129–131° C.

B) 1-(5,8,14-Triazatetracyclo[10.3.1.0$^{2,11}$.0$^{4,9}$]hexadeca-2(11),3,5,7,9-pentaene)-2,2,2-trifluoro-ethanone 1-(4,5-Diamino-10-aza-tricyclo[6.3.1.0$^{2,7}$]dodeca-2(7),3, 5-trien-10-yl)-2,2,2-trifluoro-ethanone (500 mg, 1.75 mmol) was stirred in THF (2 ml). This mixture was treated with H$_2$O (2 mL) and glyoxal sodium bisulfite addition compound hydrate (931 mg, 3.50 mmol) then stirred at 55° C. for 2.5 hours. The reaction was cooled to room temperature and extracted with ethyl acetate (3×40 ml). The combined organic layer was washed with H$_2$O (2×30 ml), dried (Na$_2$SO$_4$), filtered, concentrated and chromatographed on Silica gel to provide an off white powder (329 mg, 60%). (TLC 25% ethyl acetate/hexanes R$_f$ 0.40). M.p. 164–166° C.

C) 5,8,14-Triazatetracyclo[10.3.1.0$^{2,11}$.0$^{4,9}$]-hexadeca-2(11),3,5,7,9-pentaene hydrochloride 1-(5,8,14-Triazatetracyclo[10.3.1.0$^{2,11}$.0$^{4,9}$]hexadeca-2 (11),3,5,7,9-pentaene)-2,2,2-trifluoro-ethanone (320 mg, 1.04 mmol) was slurried in methanol (2.0 ml) and treated with Na$_2$CO$_3$ (221 mg, 2.08 mmol) in H$_2$O (2.0 ml). The mixture was warmed to 70° C. for 2 hours, then concentrated, treated with H$_2$O (20 mL) and extracted with CH$_2$Cl$_2$ (3×10 ml). The organic layer was dried through a cotton plug and concentrated to give a light yellow oil (183 mg, 83%) which solidified upon standing (M.p. 138–140° C.). This material was dissolved in methanol (10 mL), treated with 3M HCl/ethyl acetate (3 ml), concentrated and azeotroped with methanol (2×20 mL) to give solids which were recrystallized from methanol/Et$_2$O to afford product as a white solid (208 mg, 97%). (TLC 5% methanol/CH$_2$Cl$_2$ (NH$_3$) R$_f$ 0.26). $^1$H NMR (400 MHz, CD$_3$OD) δ8.94 (s, 2H), 8.12 (s, 2H), 3.70 (m, 2H), 3.54 (d, J=12.5 Hz, 2H), 3.35 (d, J=12.5 Hz, 2H), 2.49 (m, 1H), 2.08 (d, J=11.0 Hz, 1H). GCMS m/e 211 (M$^+$). M.p. 225–230° C.

Example 37

14-METHYL-5,8,14-TRIAZATETRACYCLO [10.3.1.0$^{2,11}$.0$^{4,9}$]-HEXADECA-2(11),3,5,7,9-PENTAENE HYDROCHLORIDE 5,8,14-Triazatetracyclo[10.3.1.0$^{2,11}$.0$^{4,9}$]hexadeca-2(11), 3,5,7,9-pentaene (207 mg, 0.98 mmol) was treated with 37% aqueous formaline solution (1 mL) and formic acid (1 mL) then warmed to 80° C. for 1 hour. The reaction was poured into water, made basic (NaOH, pH ~11) and extracted with ethyl acetate. The organic layer was dried (Na$_2$SO$_4$), concentrated and chromatographed on Silica gel to provide a yellow solid. This was stirred in methanol (2 mL) and treated with 3N HCl ethyl acetate (2 mL). After concentration the solids were recrystallized from methanol/Et$_2$O to afford product as a white solid (70 mg, 27%). (2% methanol/CH$_2$Cl$_2$ (NH$_3$) R$_f$ 0.47). $^1$H NMR (400 MHz, CDCl$_3$) δ8.71 (s, 2H), 7.80 (s, 2H), 3.37 (br s, 2H), 3.03 (m, 2H), 2.47 (m, 2H), 2.32 (m, 1H), 2.18 (br s, 3H), 1.84 (d, J=11.0 Hz, 1H). APCI MS m/e 226.2 [(M+1)$^+$]. M.p. >250° C.

Example 38

5-OXA-7,13-DIAZATETRACYCLO [9.3.1.0$^{2,10}$.0$^{4,8}$]-PENTADECA-2(10),3,6,8-TETRAENE HYDROCHLORIDE

A) 2,2,2-Trifluoro-1-(4-hydroxy-5-nitro-10-aza-tricyclo[6.3.1.0$^{2,7}$]dodeca-2(7),3,5-trien-10-yl)-ethanone 1-(4,5-Dinitro-10-aza-tricyclo[6.3.1.0$^{2,7}$]dodeca-2(7),3, 5-trien-10-yl)-2,2,2-trifluoro-ethanone (900 mg, 2.61 mmol) and potassium acetate (KOAc) (2.6 g, 26.1 mmol) were dissolved in DMSO (10 mL) and warmed with stirring to 100° C. for 16 hours. The mixture was cooled and diluted with H$_2$O (50 mL) then extracted with 80% ethyl acetate/hexanes (6×25 mL). The organic layer was washed with H$_2$O (3×20 mL), dried (Na$_2$SO$_4$), filtered and concentrated and purified by chromatography to give an oil (575 mg, 70%). (TLC 50% ethyl acetate/hexanes (NH$_3$) R$_f$ 0.56)

B) 2,2,2-Trifluoro-1-(4-hydroxy-5-amino-10-aza-tricyclo[6.3.1.0$^{2,7}$]dodeca-2(7),3,5-trien-10-yl)-ethanone 2,2,2-Trifluoro-1-(4-hydroxy-5-nitro-10-aza-tricyclo [6.3.1.0$^{2,7}$]dodeca-2(7),3,5-trien-10-yl)-ethanone (575 mg, 1.82 mmol) was hydrogenated in methanol under a H$_2$ atmosphere at (45 psi, or approximately 3 atmospheres) over 10% Pd/C (80 mg) for 1.5 hours then filtered through a Celite pad and concentrated to white solids (450 mg, 86%). (TLC 5% methanol/CH$_2$Cl$_2$ (NH$_3$) R$_f$ 0.6). $^1$H NMR (400 MHz, CD$_3$OD) δ6.67–6.59 (m, 2H), 4.12 (m, 1H), 3.73 (m, 1H), 3.73 (m, 1H), 3.51 (m, 1H), 3.07 (m, 2H), 2.24 (m, 1H), 1.94 (d, J=10.5 Hz, 1H). GCMS m/e 286 (M$^+$).

C) 2,2,2-Trifluoro-1-(5-oxa-7,13-diazatetracyclo [9.3.1.0$^{2,10}$.0$^{4,8}$]pentadeca-2(10),3,6,8-tetraene)-ethanone (Goldstein, S. W.; Dambek, P. J. *J. Het Chem.* 1990, 27, 335.)

2,2,2-Trifluoro-1-(4-hydroxy-5-amino-10-aza-tricyclo [6.3.1.0$^{2,7}$]dodeca-2(7),3,5-trien-10-yl)-ethanone (150 mg, 0.524 mmol), trimethyl orthoformate (0.19 mL, 1.73 mmol), pyridinium-p-toluenesulfonic acid (PPTS, 18 mg, 0.07 mmol) and xylenes (10 mL) were combined under nitrogen and stirred at 135° C. for 18 hours. The mixture was cooled, treated with H$_2$O and extracted with ethyl acetate. The extracts were dried (Na$_2$SO$_4$), filtered, concentrated and purified by chromatography to give an oil (110 mg, 71%). (TLC 20% ethyl acetate/hexanes R$_f$ 0.40)

D) 5-Oxa-7,13-diazatetracyclo[9.3.1.0$^{2,10}$.0$^{4,8}$]pentadeca-2(10),3,6,8-tetraene hydrochloride 2,2,2-Trifluoro-1-(5-oxa-7,13-diazatetracyclo [9.3.10$^{2,10}$.0$^{4,8}$]pentadeca-2(10),3,6,8-tetraene)-ethanone (110 mg, 0.37 mmol) was stirred in methanol (5 mL) and treated with Na$_2$CO$_3$ (78 mg, 0.74 mmol) in H$_2$O (2 mL). The stirred mixture was warmed to 80° C. for 2 hours, concentrated to solids, diluted with H$_2$O and extracted with ethyl acetate (3×40 mL). The product was extracted into aqueous 1N HCl solution (2×40 mL) which was washed with ethyl acetate then neutralized with saturated aqueous Na$_2$CO$_3$ solution to pH~10. The product was extracted with ethyl acetate (3×40 mL), dried (Na$_2$SO$_4$), concentrated and chromatographed on Silica gel to produce an oil. (TLC 5% methanol/CH$_2$Cl$_2$ (NH$_3$) R$_f$ 0.19).

The oil was dissolved in methanol and treated with 3N HCl ethyl acetate (4 mL) then concentrated, stirred in a minimum of CH$_2$Cl$_2$ and saturated with hexanes. After 18 hours, the product was collected by filtration (55 mg, 63%). $^1$H NMR (400 MHz, CD$_3$OD) δ8.47 (s, 1H), 7.70 (s, 1H), 7.65 (s, 1H), 3.41 (m, 2H), 3.30 (m, 2H), 3.10 (d, J=12.5 Hz, 2H), 2.47 (m, 1H), 2.15 (d, J=11.0 Hz, 1H). APCI MS m/e 201.03 [(M+1)$^+$].

Example 39

6-METHYL-5-OXA-7,13-DIAZATETRACYCLO [9.3.1.0$^{2,10}$.0$^{4,8}$]-PENTADECA-2(10),3,6,8-TETRAENE HYDROCHLORIDE

A) 2,2,2-Trifluoro-1-(6-methyl 5-oxa-7,13-diazatetracyclo[9.3.1.0$^{2,10}$.0$^{4,8}$]pentadeca-2(10),3,6,8-tetraene)-ethanone 2,2,2-Trifluoro-1-(4-hydroxy-5-amino-10-aza-tricyclo [6.3.1.0$^{2,7}$]dodeca-2(7),3,5-trien-10-yl)-ethanone (150 mg, 0.524 mmol), triethyl orthoacetate (0.34 mL, 1.83 mmol), pyridinium-p-toluenesulfonic acid (PPTS, 20 mg, 0.08 mmol) and xylenes (10 mL) were combined under nitrogen and stirred at 135° C. for 18 hours. Work-up, isolation and purification as in Example 38C provided the title compound (90 mg, 55%).

B) 6-Methyl-5-oxa-7,13-diazatetracyclo
[9.3.1.0$^{2,10}$.0$^{4,8}$]pentadeca-2(10),3,6,8-tetraene hydrochloride 2,2,2-Trifluoro-1-(6-methyl 5-oxa-7,13-diazatetracyclo [9.3.1.0$^{2,10}$.0$^{4,8}$]pentadeca-2(10),3,6,8-tetraene)-ethanone (90 mg, 0.30 mmol) was stirred in methanol (5 mL) and treated with $Na_2CO_3$ (61 mg, 0.58 mmol) in $H_2O$ (2 mL). The stirred mixture was warmed to 80° C. for 2 hours, concentrated to solids, diluted with $H_2O$ and extracted with ethyl acetate (3×40 mL). The solution was dried ($Na_2SO_4$), concentrated, and chromatographed on Silica gel to produce an oil. (TLC 10% methanol/$CH_2Cl_2$ ($NH_3$) $R_f$ 0.18). $^1$H NMR (free base) (400 MHz, $CDCl_3$)δ7.40 (s, 1H), 7.26 (s, 1H), 3.05–2.98 (m, 4H), 2.72 (d, J=12.8 Hz, 2H), 2.59 (s, 3H), 2.46 (m, 1H), 1.98 (d, J=10.5 Hz, 1H).

The oil was dissolved in methanol and treated with 3N HCl ethyl acetate (4 mL) then concentrated, stirred in a minimum of $CH_2Cl_2$ and saturated with hexanes. After 18 hours, the product was collected by filtration (10 mg, 13%). APCI MS m/e 215.2 [(M+1)$^+$]. M.p. >250° C.

Example 40

2-FLUORO-N-(4-HYDROXY-10-AZA-TRICYCLO [6.3.1.0$^{2,7}$]-DODECA-2(7),3,5-TRIEN-5-YL)-BENZAMIDE HYDROCHLORIDE 2,2,2-Trifluoro-1-(4-hydroxy-5-amino-10-aza-tricyclo [6.3.1.0$^{2,7}$]dodeca-2(7),3,5-trien-10-yl)-ethanone (150 mg, 0.524 mmol), 2-fluorobenzoyl chloride (0.07 mL, 0.576 mmol), pyridinium-p-toluenesulfonic acid (PPTS, 20 mg, 0.08 mmol), pyridine (0.046 mL, 0.576 mmol) and xylenes (5 mL) were combined under nitrogen and stirred at 135° C. for 18 hours. After 24 hours, additional PPTS (50 mg) was added and the material stirred at 135° C. for an additional 24 hours. Work-up as above provided crude product (145 mg, 0.375 mmol) which was combined with $Na_2CO_3$(s) (80 mg, 0.75 mmol) in methanol (5 mL) and $H_2O$ (2 mL) and heated to reflux. After 3 hours, the reaction was cooled and diluted with water then extracted with $CH_2Cl_2$ (4×40 mL), dried through a cotton plug then chromatographed to remove baseline impurity (5% methanol/$CH_2Cl_2$ ($NH_3$)). The crude material was treated with excess 3N HCl ethyl acetate and concentrated, then dissolved in a minimum of methanol and the solution was saturated with $Et_2O$ and stirred. After stirring 4 hours the product was collected by filtration (85 mg, 68%). $^1$H NMR (400 MHz, $CD_3OD$)δ7.99 (m, 2H), 7.59 (m, 1H), 7.36–7.23 (m, 2H), 6.82 (s, 1H), 2.99 (m, 4H), 2.78 (m, 2H), 2.35 (m, 1H), 1.96 (d, J=10.5 Hz, 1H). APCI MS m/e 313.1 [(M+1)$^+$]. M.p. 125–130° C. (subl.).

Example 41

4-CHLORO-10-AZATRICYCLO[6.3.1.0$^{2,7}$] DODECA-2(7),3,5-TRIENE HYDROCHLORIDE

A) 1-(4-Chloro-10-aza-tricyclo[6.3.1.0$^{2,7}$]dodeca-2 (7),3,5-trien-10-yl)-2,2,2-trifluoro-ethanone Copper(I)chloride (CuCl) was prepared as follows: $CuSO_4$ (4.3 g) and NaCl (1.2 g) were dissolved in hot $H_2O$ (14 mL). sodium bisulfite ($NaHSO_3$) (1 g) and sodium hydroxide (NaOH) (690 mg) were dissolved in $H_2O$ (7 mL) and added to the hot acidic solution over 5 minutes. The precipitated white solids were filtered and washed with water.

1-(4-Amino-10-aza-tricyclo[6.3.1.0$^{2,7}$]dodeca-2(7),3,5-trien-10-yl)-2,2,2-trifluoro-ethanone (460 mg, 1.7 mmol) was dissolved in $H_2O$ (2 mL) and concentrated HCl solution (1 mL) then cooled to 0° C. and treated with a solution of sodium nitrite ($NaNO_2$) (275 mg) in $H_2O$ (1 mL) dropwise. To the resulting solution was added a CuCl (202 mg, prepared as described above, 2.04 mmol) in concentrated HCl solution (2 mL) over 10 minutes (gas evolution observed). The resulting solution was warmed to 60° C. for 15 minutes, then was cooled to room temperature and extracted with ethyl acetate (4×30 mL). After drying over $Na_2SO_4$, the solution was filtered and concentrated to an oil which was filtered through a Silica pad to remove baseline material eluting with 50% ethyl acetate/hexanes to give an oil (470 mg, 95%).

B) 4-Chloro-10-azatricyclo[6.3.1.0$^{2,7}$]dodeca-2(7),3, 5-triene hydrochloride 1-(4-Chloro-10-aza-tricyclo[6.3.1.0$^{2,7}$]dodeca-2(7),3,5-trien-10-yl)-2,2,2-trifluoro-ethanone (470 mg, 1.62 mmol) and $Na_2CO_3$ (344 mg, 3.24 mmol) in methanol (30 mL) and $H_2O$ (10 mL) were heated to reflux. After 2 hours, the reaction was cooled and diluted with water then extracted with ethyl acetate (4×40 mL), dried ($Na_2SO_4$), filtered and concentrated to a yellow oil. The crude material was treated with excess 3N HCl ethyl acetate and concentrated, then dissolved in a minimum of $CH_2Cl_2$ and the solution was saturated with hexanes and stirred. After stirring 4 hours the product was collected by filtration (155 mg, 42%). $^1$H NMR (free base) (400 MHz, $CDCl_3$)δ7.15 (m, 2H), 7.09 (d, J=8.0 Hz, 1H), 3.00–2.94 (m, 4H), 2.68, (m, 2H), 2.38 (m, 1H), 1.92 (d, J=10.5 Hz, 1H). $^1$H NMR (HCl salt) (400 MHz, DMSO-$d_6$)δ7.30–7.20 (m, 3H), 3.30–3.15 (m, 6H), 2.37 (m, 1H), 1.89 (d, J=11.0 Hz, 1H). APCI MS m/e 194.1 [(M+1)$^+$].

Example 42

10-AZATRICYCLO[6.3.1.0$^{2,7}$]DODECA-2(7),3,5-TRIEN-4-YLCYANIDE HYDROCHLORIDE

A) 1-(4-Iodo-10-aza-tricyclo[6.3.1.0$^{2,7}$]dodeca-2(7), 3,5-trien-10-yl)-2,2,2-trifluoro-ethanone 1-(4-Amino-10-aza-tricyclo[6.3.1.0$^{2,7}$]dodeca-2(7),3,5-trien-10-yl)-2,2,2-trifluoro-ethanone (500 mg, 1.85 mmol) was dissolved in $H_2O$ (5 mL) and concentrated $H_2SO_4$ solution (0.5 mL) then cooled to 0° C. and treated with a solution of sodium nitrite ($NaNO_2$) (140 mg, 2.04 mmol) in $H_2O$ (2 mL) dropwise. Potassium iodide (460 mg, 2.78 mmol) in 1N $H_2SO_4$ solution (0.5 mL) was added over 10 minutes (reaction becomes dark red). The resulting solution was warmed to room temperature and stirred 18 hours. The reaction was quenched with $NaHSO_3$ and water (pH 2.5) then extracted with ethyl acetate (4×30 mL). After drying ($Na_2SO_4$), the solution was filtered and concentrated to a yellow oil which was chromatographed on Silica gel to provide a yellow oil. (260 mg, 37%). (TLC 30% ethyl acetate/hexanes $R_f$ 0.70). (A 5.4 g scale performed as above yielded 5 g, 67%).

B) 4-Iodo-10-aza-tricyclo[6.3.1.0$^{2,7}$]dodeca-2(7),3, 5-triene-10-carboxylic acid tert-butyl ester 1-(4-Iodo-10-aza-tricyclo[6.3.1.0$^{2,7}$]dodeca-2(7),3,5-trien-10-yl)-2,2,2-trifluoro-ethanone (5 g, 13.1 mmol) and 37% saturated aqueous NH$_4$OH solution (50 mL) were stirred in methanol (250 ml) for 2 hours then concentrated and azeotroped with methanol (2×50 mL). The resulting product was stirred in 1,4-dioxane (75 mL) and treated with saturated Na$_2$CO$_3$ solution (15 mL). To this was added di-t-butyldicarbonate (5.71 g, 26.2 mmol). After stirring 18 hours the reaction was treated with H$_2$O (50 mL) and extracted with CH$_2$Cl$_2$ (4×30 mL), dried (Na$_2$SO$_4$), filtered, concentrated and chromatographed on Silica gel (TLC 20% ethyl acetate/hexanes) to provide product as an oil (4.9 g, 98%).

C) 4-Cyano-10-aza-tricyclo[6.3.1.0$^{2,7}$]dodeca-2(7), 3,5-triene-10-carboxylic acid tert-butyl ester (Utilizing the methods described in: House, H. O.; Fischer, W. F. *J. Org. Chem.* 1969, 3626.)

CuCN (108 mg, 1.21 mmol) and NaCN (59 mg, 1.21 mmol) were combined in dry DMF (6 mL) and warmed to 150° C. under N$_2$. Solution occurs in 20 minutes. To this was added 4-iodo-10-aza-tricyclo[6.3.1.0$^{2,7}$]dodeca-2(7),3,5-triene-10-carboxylic acid tert-butyl ester (232 mg, 0.6 mmol) in DMF (3.5 mL) and the mixture was stirred for 18 hours at 150° C. The reaction was cooled and diluted with 50% saturated aqueous NaCl solution and extracted with 50% ethyl acetate/hexanes (3×30 mL). After drying (Na$_2$SO$_4$), filtration and concentration the product was isolated by chromatography (86 mg, 50%). (TLC 20% ethyl acetate/hexanes R$_f$ 0.28).

D) 10-Azatricyclo[6.3.1.0$^{2,7}$]dodeca-2(7),3,5-trien-4-yl cyanide hydrochloride 4-Cyano-10-aza-tricyclo[6.3.1.0$^{2,7}$]dodeca-2(7),3,5-triene-10-carboxylic acid tert-butyl ester was treated with 3N HCl ethyl acetate (6 mL) and warmed to reflux for 2 hours, then concentrated, dissolved in a minimum of methanol which was saturated with Et$_2$O and stirred 18 hours. The product was collected by filtration (49 mg, 73%). $^1$H NMR (400 MHz, DMSO-d$_6$)δ9.66 (br s, NH), 7.86 (br s, NH), 7.74–7.70 (m, 2H), 7.49 (d, J=7.5 Hz, 1H), 3.33–2.97 (m, 6H), 2.17 (m, 1H), 2.01 (d, J=11.0 Hz, 1H). GCMS m/e 184 (M$^+$). M.p. 268–273° C.

Example 43

3-(10-AZATRICYCLO[6.3.1.0$^{2,7}$]DODECA-2(7),3, 5-TRIEN-4-YL)-5-METHYL-1,2,4-OXADIAZOLE HYDROCHLORIDE

4-Cyano-10-aza-tricyclo[6.3.1.0$^{2,7}$]dodeca-2(7),3,5-triene-10-carboxylic acid tert-butyl ester (300 mg, 1.1 mmol) was stirred in ethanol (10 mL). To this hydroxylamine hydrochloride (382 mg, 5.5 mmol) and NaOH (242 mg, 6.05 mmol) were added and the mixture was warmed to reflux. After 45 minutes, the reaction was cooled, diluted with H$_2$O and extracted with ethyl acetate. The organic layer was dried (Na$_2$SO$_4$) and concentrated to afford a yellow solid (110 mg, 0.35 mmol). This solid was dissolved in pyridine (1 mL) and treated with acetyl chloride (0.03 mL, 0.415 mmol) and warmed to 100° C. for 18 hours. The reaction was cooled, treated with H$_2$O and extracted with ethyl acetate. The organic extracts were washed with water and saturated aqueous NaCl solution, dried (Na$_2$SO$_4$) and concentrated. Chromatography on Silica gel afforded product (50 mg, 0.15 mmol). (25% ethyl acetate/hexanes R$_f$ 0.18). This product was treated with 2N HCl methanol (10 mL), heated to 70° C. for 1 hour, cooled, concentrated and recrystallized from methanol/Et$_2$O to provide product (15 mg). APCI MS m/e 242.2 [(M+1)$^+$].

Example 44

1-(10-AZATRICYCLO[6.3.1.0$^{2,7}$]DODECA-2(7),3, 5-TRIEN-4-YL)-1-ETHANONE HYDROCHLORIDE

A) 1-(4-Acetyl-10-aza-tricyclo[6.3.1.0$^{2,7}$]dodeca-2(7),3,5-trien-10-yl)-2,2,2-trifluoro-ethanone 1-(10-Aza-tricyclo[6.3.1.0$^{2,7}$]dodeca-2(7),3,5-trien-10-yl)-2,2,2-trifluoro-ethanone (253 mg, 1.0 mmol) and AcCl (0.68 mL, 10 mmol) were dissolved in DCE (3 mL) and treated with aluminum chloride (AlCl$_3$) (667 mg, 5.0 mmol). The resulting yellow mixture was stirred for 30 minutes then poured over ice and saturated aqueous NaHCO$_3$ solution. After stirring 20 minutes the mixture was extracted with CH$_2$Cl$_2$ (3×30 mL). The organic layer was dried through a cotton plug then concentrated to a orange-yellow oil (255 mg, 86%).

B) 4-Acetyl-10-aza-tricyclo[6.3.1.0$^{2,7}$]dodeca-2(7), 3,5-triene-10-carboxylic acid tert-butyl ester 1-(4-Acetyl-10-aza-tricyclo[6.3.1.0$^{2,7}$]dodeca-2(7),3,5-trien-10-yl)-2,2,2-trifluoro-ethanone (1.3 g, 4.37 mmol) and 37% aqueous NH$_4$OH solution (10 mL) were stirred in methanol (30 ml) for 3 hours, then concentrated and azeotroped with methanol (2×50 mL). (This product could be converted to an HCl salt directly: see the next example.) The resulting product was stirred in 1,4-dioxane (20 mL) and treated with saturated aqueous Na$_2$CO$_3$ solution (5 mL). To this was added di-t-butyldicarbonate (1.91 g, 8.74 mmol). After stirring 2 hours, the reaction was treated with H$_2$O (50 mL), extracted with CH$_2$Cl$_2$ (4×30 mL), dried (Na$_2$SO$_4$), filtered, concentrated and chromatographed to provide an oil (1.3 g, 100%). (TLC 40% ethyl acetate/hexanes R$_f$ 0.56).

C) 1-(10-Azatricyclo[6.3.1.0$^{2,7}$]dodeca-2(7),3,5-trien-4-yl)-1-ethanone hydrochloride 4-Acetyl-10-aza-tricyclo[6.3.1.0$^{2,7}$]dodeca-2(7),3,5-triene-10-carboxylic acid tert-butyl ester (190 mg, 0.63 mmol) was treated with excess 3N HCl ethyl acetate and warmed to 70° C. for 1 hour then concentrated and dissolved in a minimum of methanol. The resulting solution was saturated with Et$_2$O and stirred. After 18 hours the white crystalline product was collected by filtration (81 mg, 54%). $^1$H NMR (400 MHz, DMSO-d$_6$)δ9.75 (br s, NH), 7.89 (s, 1H), 7.88 (d, J=8.0 Hz, 1H), 7.74 (br s, NH), 7.44 (d, J=8.0 Hz, 1H), 3.33 (br s, 2H), 3.22 (br s, 2H), 3.00 (br m, 2H), 2.54 (s, 3H), 2.17 (m, 1H), 2.02 (d, J=11.0 Hz, 1H). GCMS m/e 201 (M$^+$). M.p. 198–202° C.

Example 45

10-AZATRICYCLO[6.3.1.0$^{2,7}$]DODECA-2(7),3,5-TRIEN-4-OL HYDROCHLORIDE

A) Acetic acid 10-trifluoroacetyl-10-aza-tricyclo[6.3.1.0$^{2,7}$]dodeca-2(7),3,5-trien-4-yl ester 1-(4-Acetyl-10-aza-tricyclo[6.3.1.0$^{2,7}$]dodeca-2(7),3,5-trien-10-yl)-2,2,2-trifluoro-ethanone (2.5 g, 8.41 mmol) and 3-chloroperoxybenzoic acid (m-CPBA) (7.5 g, 42 mmol) were stirred in CH$_2$Cl$_2$ (20 mL) and warmed to 40° C. for 18 hours. The mixture was cooled to room temperature, then treated with dimethylsulfide (Me$_2$S) (3 mL, 40.8 mmol) and stirred 24 hours. The resulting mixture was poured into ice and saturated aqueous Na$_2$CO$_3$ solution (100 mL) then extracted with Et$_2$O (4×40 mL). The organic layer was washed saturated aqueous Na$_2$CO$_3$ solution (3×40 mL) then dried (Na$_2$SO$_4$), filtered and concentrated to afford an oil (1.83 g, 69%). (TLC ethyl acetate R$_f$ 0.80).

B) 2,2,2-Trifluoro-1-(4-hydroxy-10-aza-tricyclo[6.3.1.0$^{2,7}$]dodeca-2(7),3,5-trien-10-yl)-ethanone Acetic acid 10-trifluoroacetyl-10-aza-tricyclo[6.3.1.0$^{2,7}$]dodeca-2(7),3,5-trien-4-yl ester (900 mg, 2.87 mmol) was stirred in methanol (20 mL) and saturated aqueous NaHCO$_3$ solution (15 mL) for 48 hours. The mixture was concentrated, diluted with H$_2$O and extracted with CH$_2$Cl$_2$ (3×20 mL) then dried through a cotton plug. Chromatography on Silica gel provided pure product (420 mg, 54%). (TLC 5% methanol/CH$_2$Cl$_2$ R$_f$ 0.44). $^1$H NMR (400 MHz, CDCl$_3$)δ7.05 (m, 1H), 6.70 (m, 1H), 6.62 (m, 1H), 4.32 (m, 1H), 3.84 (m, 1H), 3.48 (m, 1H), 3.21 (br s, 1H), 3.16 (br s, 1H), 3.09 (m, 1H), 2.38 (m, 1H), 1.97 (d, J=11.0 Hz, 1H).

C) 10-Azatricyclo[6.3.1.0$^{2,7}$]dodeca-2(7),3,5-trien-4-ol hydrochloride 2,2,2-Trifluoro-1-(4-hydroxy-10-aza-tricyclo[6.3.1.0$^{2,7}$]dodeca-2(7),3,5-trien-10-yl)-ethanone (50 mg, 0.184 mmol) was dissolved in methanol/H$_2$O (3/1, 5 mL), treated with Na$_2$CO$_3$(s) (40 mg, 0.369 mmol) and warmed to 65° C. for 2 hours. The mixture was concentrated, diluted with H$_2$O and extracted with CH$_2$Cl$_2$ (3×20 mL) then dried through a cotton plug. Filtration through a Silica gel plug provided an oil (10% methanol/CH$_2$Cl$_2$) which was treated with 3N HCl ethyl acetate (3 mL) then concentrated, dissolved in a minimum of methanol which was saturated with Et$_2$O and stirred. After 18 hours the white crystalline product was collected by filtration (10 mg, 26%). $^1$H NMR (400 MHz, CDOD$_3$)δ7.16 (d, J=8.0 Hz, 1H), 6.80 (d, J=2.0 Hz, 1H), 6.72 (dd, J=8.0, 2.0 Hz, 1H), 3.32–3.28 (4H), 3.09 (dd, J=14.5, 12.0 Hz, 2H), 2.32 (m, 1H), 2.03 (d, J=11.0 Hz, 1H). APCI MS m/e 176.2 [(M+1)$^+$]. M.p. 308 (dec.)° C.

Example 46

7-METHYL-5-OXA-6,13-DIAZATETRACYCLO[9.3.1.0$^{2,10}$.0$^{4,8}$]PENTADECA-2,4(8),6,9-TETRAENE HYDROCHLORIDE

A) 1-(4-Acetyl-5-hydroxy-10-aza-tricyclo[6.3.1.0$^{2,7}$]dodeca-2(7),3,5-trien-10-yl)-2,2,2-trifluoro-ethanone Acetic acid 10-trifluoroacetyl-10-aza-tricyclo[6.3.1.0$^{2,7}$]dodeca-2(7),3,5-trien-4-yl ester (800 mg, 2.55 mmol) was combined with AlCl$_3$ (1.0 g, 7.65 mmol) and warmed to 170° C. for 2 hours. The mixture was cooled and treated with 1N aqueous HCl solution (20 mL), extracted with ethyl acetate and dried (Na$_2$SO$_4$). Chromatography affords an oil (190 mg, 24%). (TLC ethyl acetate R$_f$ 0.75). $^1$H NMR (400 MHz, CDCl$_3$)δ12.58 (s, 0.5H), 12.52 (s, 0.5H), 7.53 (s, 1H), 6.86 (s, 1H), 4.33 (m, 1H), 3.91 (m, 1H), 3.56 (m, 1H), 3.28 (br s, 1H), 3.24 (br s, 1H), 3.14 (m, 1H), 2.35 (m, 1H), 1.97 (br d, J=11.2 Hz, 1H).

B) 2,2,2-Trifluoro-1-[4-hydroxy-5-(1-hydroxyimino-ethyl)-10-aza-tricyclo[6.3.1.0$^{2,7}$]-dodeca-2(7),3,5-trien-10-yl]-ethanone 1-(4-Acetyl-5-hydroxy-10-aza-tricyclo[6.3.1.0$^{2,7}$]dodeca-2(7),3,5-trien-10-yl)-2,2,2-trifluoro-ethanone (190 mg, 0.605 mmol), hydroxylamine HCl (99 mg, 1.21 mmol) and sodium acetate (118 mg, 1.21 mmol) were combined in methanol (4 mL) and H$_2$O (1 mL) and warmed to 65° C. for 18 hours. The mixture was cooled, diluted with H$_2$O and extracted with ethyl acetate which was dried (Na$_2$SO$_4$), filtered and concentrated to provide a yellow oil (177 mg, 93%).

C) 2,2,2-Trifluoro-7-Methyl-5-oxa-6,13-diazatetracyclo[9.3.1.0$^{2,10}$.0$^{4,8}$]pentadeca-2,4(8),6,9-tetraene-ethanone The above oil, 2,2,2-trifluoro-1-[4-hydroxy-5-(1-hydroxyimino-ethyl)-10-aza-tricyclo[6.3.1.0$^{2,7}$]dodeca-2(7),3,5-trien-10-yl]-ethanone (177 mg, 0.54 mmol) was stirred in DCE (3 mL), treated with triethylamine (0.4 mL, 2.8 mmol) and acetic anhydride (Ac$_2$O) (0.3 mL, 2.8 mmol) then stirred 18 hours. The reaction was treated with H$_2$O and extracted with ethyl acetate. The extracts were dried (Na$_2$SO$_4$), filtered and concentrated to a yellow oil which was dissolved in anhydrous DMF (3 mL) and treated with 60% NaH in oil (32 mg, 1.08 mmol). After stirring 18 hours, additional 60% NaH in oil was introduced (33 mg) and the mixture was stirred 2 hours. The reaction was quenched with H$_2$O (5 mL) and extracted with 80% ethyl acetate/hexanes (3×30 mL). The organic layer was washed with H$_2$O (3×20 mL), dried (Na$_2$SO$_4$), filtered and concentrated and chromatographed to provide an oil (40% ethyl acetate/hexanes R$_f$ 0.56).

D) 7-Methyl-5-oxa-6,13-diazatetracyclo[9.3.1.0$^{2,10}$.0$^{4,8}$]pentadeca-2,4(8),6,9-tetraene hydrochloride Utilizing the methods described in Example 19C, 2,2,2-Trifluoro-7-Methyl-5-oxa-6,13-diazatetracyclo[9.3.1.0$^{2,10}$.0$^{4,8}$]pentadeca-2,4(8),6,9-tetraene-ethanone was converted to the title compound. This was treated with 3N HCl ethyl acetate (3 mL), concentrated and dissolved in a minimum of CH$_2$Cl$_2$ which was saturated with hexanes and stirred. After 18 hours the white crystalline product was collected by filtration (18 mg, 13% overall). $^1$H NMR (400 MHz, DMSO-d$_6$)δ7.72 (s, 1H), 7.63 (s, 1H), 3.42–2.98 (m, 6H), 2.50 (s, 3H), 2.23 (m, 1H), 2.08 (d, J=10.5 Hz, 1H). APCI MS m/e 215.2 [(M+1)$^+$].

Example 47

4-(2-METHYL-2H-PYRAZOL-3-YL)-10-AZA-TRICYCLO[6.3.1.0$^{2,7}$]DODECA-2(7),3,5-TRIENE HYDROCHLORIDE and 4-(1-METHYL-1H-PYRAZOL-3-YL)-10-AZA-TRICYCLO[6.3.1.0$^{2,7}$]DODECA-2(7),3,5-TRIENE HYDROCHLORIDE 1-(4-Acetyl-10-aza-tricyclo[6.3.1.0$^{2,7}$]dodeca-2(7),3,5-trien-10-yl)-2,2,2-trifluoro-ethanone (1.0 g, 3.3 mmol) and dimethylformamide dimethylacetal (DMF-DMA) (4.0 g, 33.6 mmol) were warmed to 140° C. for 18 hours. After cooling, a crystalline precipitate was filtered and rinsed with ethyl acetate (690 mg, 58%).

The above solid, 3-dimethylamino-1-(10-trifluoroacetyl-10-aza-tricyclo[6.3.1.0$^{2,7}$]dodeca-2(7),3,5-trien-4-yl)-propenone, (200 mg, 0.56 mmol) was dissolved in ethanol (2 mL) and treated with 5N HCl ethanol (0.1 mL) followed by methyl hydrazine (0.6 mmol). The resulting mixture was warmed to 70° C. for 4 hours. The mixture was cooled, diluted with water and extracted with ethyl acetate, dried (Na$_2$SO$_4$) and concentrated. Chromatography on Silica gel provided a 3/1 mixture of regioisomeric products (130 mg, 68%). (TLC 50% ethyl acetate/hexanes R$_f$ 0.40).

The above oil (130 mg, 0.388 mmol) and Na$_2$CO$_3$(s) (82 mg, 0.775 mmol) were stirred in methanol (10 mL) and H$_2$O (5 mL) for 18 hours. After cooling the reaction was diluted with water, extracted with CH$_2$Cl$_2$ dried through a cotton plug and concentrated. The product was purified by chromatography on Silica gel and concentrated to an oil. The salt was generated with 2N HCl methanol, concentrated and recrystallized from methanol/ethyl acetate to provide a 3/1 mixture of regioisomeric pyrrazoles (85 mg, 58%). (5% methanol/CH$_2$Cl$_2$ (NH$_3$) R$_f$ 0.25). TFA-precursor APCI MS m/e 336.2 [(M+1)$^+$].

Example 48

4,5-DICHLORO-10-AZATRICYCLO[6.3.1.0$^{2,7}$]DODECA-2(7),3,5-TRIENE HYDROCHLORIDE

A) 1-(4,5-Dichloro-10-aza-tricyclo[6.3.1.0$^{2,7}$]dodeca-2(7),3,5-trien-10-yl)-2,2,2-trifluoro-ethanone (Based on Campaigne, E.; Thompson, W. *J. Org. Chem.* 1950, 72, 629.)

1-(10-Aza-tricyclo[6.3.1.0$^{2,7}$]dodeca-2(7),3,5-trien-10-yl)-2,2,2-trifluoro-ethanone (539 mg, 2.1 mmol) was stirred in CH$_2$Cl$_2$ (5 mL) and treated with ICl$_3$ (s) (982 mg, 4.21 mmol). The resulting orange solution was stirred 0.5 hours, poured into saturated aqueous NaHSO$_3$ solution (25 mL), extracted with CH$_2$Cl$_2$ (3×25 mL), dried through a cotton plug and concentrated to an oil (570 mg, 84%) (TLC 50% ethyl acetate/hexanes R$_f$ 0.62).

B) 4,5-dichloro-10-azatricyclo[6.3.1.0$^{2,7}$]dodeca-2(7),3,5-triene hydrochloride 1-(4,5-Dichloro-10-aza-tricyclo[6.3.1.0$^{2,7}$]dodeca-2(7),3,5-trien-10-yl)-2,2,2-trifluoro-ethanone (570 mg, 1.75 mmol) was stirred in methanol (25 mL) and treated with Na$_2$CO$_3$(s) (5 g, 47 mmol) in H$_2$O (5 mL). The stirred mixture was warmed to 70° C. for 4 hours, concentrated to solids, diluted with H$_2$O (5 mL) and extracted with ethyl acetate (3×40 mL). The product was extracted into 1N aqueous HCl solution (2×40 mL) which was washed with ethyl acetate then neutralized with saturated aqueous Na$_2$CO$_3$ solution to pH~10. Product was extracted with CH$_2$Cl$_2$ (3×40 mL), filtered through a cotton plug and concentrated to an oil (400 mg, 100%).

The oil was dissolved in methanol and treated with 3N HCl ethyl acetate (4 mL) and concentrated, then dissolved in a minimum of methanol and which was saturated with Et$_2$O and stirred 18 hours. The product was collected by filtration (210 mg, 45%). (TLC 50% ethyl acetate/hexanes (NH$_3$) R$_f$ 0.08). $^1$H NMR (400 MHz, DMSO-d$_6$)δ7.58 (s, 2H), 3.33–2.97 (m, 6H), 2.18 (m, 1H), 1.99 (d, J=10.5 Hz, 1H). $^{13}$C NMR (100 MHz, DMSO-d$_6$)δ141.02, 130.60, 126.58, 45.54, 40.55, 38.30. GCMS m/e 227, 229 (M$^+$). M.p. 283–291° C.

Example 49

N$^4$,N$^4$-DIMETHYL-10-AZATRICYCLO[6.3.1.0$^{2,7}$]-DODECA-2(7),3,5-TRIENE-4-SULFONAMIDE HYDROCHLORIDE

A) 10-Trifluoroacetyl-10-aza-tricyclo[6.3.1.0$^{2,7}$]dodeca-2(7),3,5-triene-4-sulfonyl chloride 1-(10-Aza-tricyclo[6.3.1.0$^{2,7}$]dodeca-2(7),3,5-trien-10-yl)-2,2,2-trifluoro-ethanone (530 mg, 2.1 mmol) was added to chlorosulfonic acid (2 mL, 30 mmol) and stirred for 5 minutes. The mixture was quenched with ice, extracted with ethyl acetate, dried (Na$_2$SO$_4$), filtered and concentrated to provide an oil (640 mg, 87%). (TLC 30% ethyl acetate/hexanes R$_f$ 0.15).

B) N$^4$,N$^4$-Dimethyl-10-azatricyclo[6.3.1.0$^{2,7}$]dodeca-2(7),3,5-triene-4-sulfonamide hydrochloride 10-Trifluoroacetyl-10-aza-tricyclo[6.3.1.0$^{2,7}$]dodeca-2(7),3,5-triene-4-sulfonyl chloride (320 mg, 0.9 mmol) was stirred in THF (10 mL) and treated with 40% Me$_2$NH/H$_2$O (1.5 mL). After 10 minutes the mixture was concentrated and chromatographed on Silica gel (TLC 30% ethyl acetate/hexanes R$_f$ 0.31) to provide an oil (256 mg, 78%). This material was dissolved in methanol (6 mL) and NH$_4$OH (2 mL) and stirred 18 hours. The mixture was concentrated and azeotroped from methanol (3 times) The resulting oil was dissolved in methanol and treated with 3N HCl ethyl acetate (4 mL), concentrated, dissolved in a minimum of methanol and which was saturated with Et$_2$O and stirred 18 hours. The product was collected by filtration as a white powder (163 mg, 59%). (TLC 10% methanol/CH$_2$Cl$_2$ (NH$_3$) R$_f$ 0.54). $^1$H NMR (data, free base) (400 MHz, CDCl$_3$)δ7.64 (m, 2H), 7.41 (d, J=8.0 Hz, 1H), 3.30 (m, 2H), 3.20 (d, J=12.5 Hz, 2H), 3.07 (dd, J=12.5, 2.2 Hz, 2H), 2.69 (s, 6H), 2.45, (m, 1H), 2.00 (d, J=11.0 Hz, 1H). $^{13}$C NMR (100 MHz, CDCl$_3$)δ128.43, 124.16, 122,75, 46.67, 46.55, 42.11, 39.44, 37.81. GCMS m/e 266 (M$^+$). (data HCl salt) $^1$H NMR (400 MHz, DMSO-d$_6$)δ7.68–7.52 (3H), 3.38 (m, 2H), 3.24 (m, 2H), 3.04 (m, 2H), 2.58 (s, 6H), 2.22 (m, 1H), 2.04 (d, J=11.0 Hz, 1H). GCMS m/e 266 (M$^+$). Anal. Calcd. for C$_{13}$H$_{18}$N$_2$O$_2$HCl: C, 51.56; H, 6.32; N, 9.25. Found C, 51.36; H, 6.09; N, 9.09.

Example 50

4-(1-PYRROLIDINYLSULFONYL)-10-AZATRICYCLO[6.3.1.0$^{2,7}$]-DODECA-2(7),3,5-TRIENE HYDROCHLORIDE

The pyrrolidine analogue was prepared from 10-trifluoroacetyl-10-aza-tricyclo[6.3.1.0$^{2,7}$]dodeca-2(7),3,5-triene- 4-sulfonyl chloride (320 mg, 0.9 mmol) as by substituting pyrroline in the coupling step described in Example 49B. The TFA product was isolated as an oil (314 mg, 89%). Deprotection and conversion to the salt as in Example 49B affords a white powder (189 mg, 63%). (TLC 10% methanol/$CH_2Cl_2$ ($NH_3$) $R_f$ 0.60). (TLC 50% ethyl acetate/hexanes $R_f$ 0.65). $^1$H NMR (400 MHz, $CDCl_3$)δ7.66 (d, J=8.0 Hz, 1H), 7.64 (s, 1H), 7.37 (d, J=8.0 Hz, 1H), 3.30–3.15 (m, 8H), 3.00 (m 2H), 2.39 (m, 1H), 1.98 (d, J=11.5 Hz, 1H), 1.72 (m, 4H). $^{13}$C NMR (100 MHz, $CDCl_3$)δ146.91, 144.08, 136.65, 127.90, 124.18, 122.36, 50.43, 47.87, 46.80, 46.63, 42.11, 39.63, 25.10. APCI MS m/e 293 [(M+1)$^+$]. (data HCl salt) $^1$H NMR (400 MHz, DMSO-$d_6$)δ9.78 (br s, NH), 8.1 (br s, NH), 7.73 (d, J=1.5 Hz, 1H), 7.66 (dd, J=8.0, 1.5 Hz, 1H), 7.53 (d, J=8.0 Hz, 1H), 3.39–3.01 (10H), 2.21 (m, 1H), 2.04 (d, J=11.0 Hz, 1H), 1.66 (m, 4H). GCMS m/e 292 (M$^+$). Anal. Calcd. For $C_{13}H_{18}N_2O_2$HCl.½methanol: C, 54.07; H, 6.47; N, 8.51. Found C, 53.98; H, 6.72; N, 8.12

Example 51

5,13-DIAZATETRACYCLO[9.3.1.0$^{2,10}$.0$^{4,8}$]-PENTADECA-2,4(8),9-TRIEN-6-ONE HYDROCHLORIDE (The title compound was prepared following the procedures described in Quallich, G. J.; Morrissey, P. M. *Synthesis* 1993, 51–53, treating 4,5-dinitro-10-aza-tricyclo[6.3.1.0$^{2,7}$] dodeca-2(7),3,5-triene-10-carboxylic acid tert-butyl ester as an equivalent to an ortho fluoro phenyl moiety.) $^1$H NMR (400 MHz, DMSO-$d_6$)δ10.42 (s, NH), 9.88 (br s, NH), 7.52 (br s, 1H), 7.15 (s, 1H), 6.79 (s, 1H), 3.41 (d, J=5.0 Hz, 2H), 3.35–3.13 (m, 4H), 2.93 (m, 2H), 2.12 (m, 1H), 1.95 (d, J=11.5 Hz, 1H). APCI MS m/e 215.2 [(M+1)$^+$].

Example 52

6-OXO-5-OXA-7,13-DIAZATETRACYCLO [9.3.1.0$^{2,10}$.0$^{4,8}$]-PENTADECA-2(10),3,6,8-TETRAENE HYDROCHLORIDE (For references, see: Nachman, R. J. *J. Het. Chem.* 1982, 1545.) 2,2,2-Trifluoro-1-(4-hydroxy-5-amino-10-aza-tricyclo[6.3.1.0$^{2,7}$]dodeca-2(7),3,5-trien-10-yl)-ethanone (317 mg, 1.11 mmol) was stirred in THF (10 mL), treated with carbonyldiimidazole (269 mg, 1.66 mmol) and warmed to 60° C. for 18 hours. The mixture was concentrated, diluted with $CH_2Cl_2$ (50 mL) and washed with 1N aqueous HCl solution (3×10 mL). The organic layer was dried through a cotton plug, concentrated and chromatographed on Silica gel (50% ethyl acetate/Hexanes) to provide an oil (130 mg). This material converted to the title compound by the methods described in Example 19C. $^1$H NMR (400 MHz, DMSO-$d_6$) δ 11.78 (s, NH), 9.56 (br s, NH), 7.63 (br s, NH), 7.24 (s, 1H), 7.07 (s, 1H), 3.26 (br s, 2H), 3.16 (br t, J=9.5 Hz, 1H), 2.93 (br s, 1H), 2.18 (m, 1H), 1.97 (d, J=11.0 Hz, 1H). APCI MS m/e 217.2 [(M+1)$^+$].

Example 53

6-BENZYL-5-OXA-7,13-DIAZATETRACYCLO [9.3.1.0$^{2,10}$.0$^{4,8}$]-PENTADECA-2(10),3,6,8-TETRAENE HYDROCHLORIDE 2,2,2-Trifluoro-1-(4-hydroxy-5-amino-10-aza-tricyclo [6.3.1.0$^{2,7}$]dodeca-2(7),3,5-trien-10-yl)-ethanone and phenyl-acetyl chloride were converted to the title compound following the procedures described in Example 54. $^1$H NMR (400 MHz, $CD_3OD$) δ 7.63 (s, 1H), 7.58 (s, 1H), 7.36–7.24 (5H), 4.29 (s, 2H), 3.46 (d, J=2.5 Hz, 2H), 3.39 (d, J=12.0 Hz, 2H), 3.18 (2H), 2.42 (m, 1H), 2.15 (d, J=11.5 Hz, 1H). APCI MS m/e 291.2 [(M+1)$^+$].

Example 54

6-ETHYL-5-OXA-7,13-DIAZATETRACYCLO [9.3.1.0$^{2,10}$.0$^{4,8}$]-PENTADECA-2(10),3,6,8-TETRAENE HYDROCHLORIDE 2,2,2-Trifluoro-1-(4-hydroxy-5-amino-10-aza-tricyclo [6.3.1.0$^{2,7}$]dodeca-2(7),3,5-trien-10-yl)-ethanone and propionyl chloride were converted to the title compound following the procedures described in Example 40 and Goldstein, S. W.; Dambek, P. J. *J. Het. Chem.* 1990, 27, 335. $^1$H NMR (400 MHz, $CD_3OD$) δ 7.64 (s, 1H), 7.62 (s, 1H), 3.48 (d, J=2.5 Hz, 2H), 3.41 (d, J=12.0 Hz, 2H), 3.20 (2H), 3.01 (q, J=7.5 Hz, 2H), 2.45 (m, 1H), 2.17 (d, J=11.5 Hz, 1H), 1.42 (t, J=7.5 Hz, 3H). APCI MS m/e 229.2 [(M+1)$^+$].

Example 55

6-ISOPROPYL-5-OXA-7,13-DIAZATETRACYCLO[9.3.1.0$^{2,10}$.0$^{4,8}$]-PENTADECA-2(10),3,6,8-TETRAENE HYDROCHLORIDE 2,2,2-Trifluoro-1-(4-hydroxy-5-amino-10-aza-tricyclo [6.3.1.0$^{2,7}$]dodeca-2(7),3,5-trien-10-yl)-ethanone and isobutyryl chloride were converted to the title compound following the procedures described in Example 54. (TLC 25% ethyl acetate/hexanes $R_f$ 0.14). $^1$H NMR (400 MHz, $CD_3OD$) δ 7.65 (2H), 3.49 (br s, 2H), 3.41 (d, J=12.0 Hz, 2H), 3.33–3.19 (3H), 2.45 (m, 1H), 2.18 (d, J=11.5 Hz, 1H), 1.45 (d, J=7.0 Hz, 6H). APCI MS m/e 243.2 [(M+1)$^+$]. (HCl salt) M.p. 249–251° C.

Example 56

5,14-DIAZATETRACYCLO[10.3.1.0$^{2,11}$.0$^{4,9}$] HEXADECA-2(11),3,5,7,9-PENTAENE HYDROCHLORIDE

A) 1-(5,14-Diazatetracyclo[10.3.1.0$^{2,11}$.0$^{4,9}$]hexadeca-2(11),3,5,7,9-Pentaen-10-yl)-2,2,2-trifluoroethanone (Based on the method of Campbell. K. N.; Schaffner. I. J. *J. Am. Chem. Soc.* 1945, 67, 86.)

1-(4-Amino-10-aza-tricyclo[6.3.1.0$^{2,7}$]dodeca-2(7),3,5-trien-10-yl)-2,2,2-trifluoro-ethanone (607 mg, 1.98 mmol) was dissolved in 95% ethanol/$H_2O$ (5 mL) and treated with $FeCl_3$.6$H_2O$ (800 mg, 2.97 mmol), $ZnCl_2$ (27 mg, 0.20 mmol) in ethanol (2 mL). The mixture was warmed to 65° C. for 15 min., treated with acrolein (0.2 mL, 2.97 mmol) and warmed to reflux for 2.5 hours. The mixture was judged complete by TLC, cooled and quenched into saturated aqueous $NaHCO_3$ solution (40 mL). The mixture (pH 8.5) was extracted with $CH_2Cl_2$ (8×30 mL). The organic layer was washed with $H_2O$ and saturated aqueous NaCl solution then dried through a cotton plug. Concentration afforded a dark oil which was chromatographed on Silica gel to provide a yellow oil (105 mg, 17%). (TLC 50% ethyl acetate/hexanes $R_f$ 0.08).

B) 5,14-Diazatetracyclo[10.3.1.0$^{2,11}$.0$^{4,9}$]hexadeca-2 (11),3,5,7,9-pentaene hydrochloride 1-(5,14-Diazatetracyclo[10.3.1.0$^{2,11}$.0$^{4,9}$]hexadeca-2(11), 3,5,7,9-pentaen-10-yl)-2,2,2-trifluoro-ethanone (94.7 mg, 0.31 mmol) was converted to the title compound using methods described in Example 17 to provide a crystalline solid (36.9 mg). $^1$H NMR (400 MHz, CD$_3$OD) δ 9.19 (m, 2H), 8.33 (s, 1H), 8.27 (s, 1H), 8.10 (dd, J=8.3, 5.6 Hz, 1H), 3.78 (br s, 1H), 3.74 (br s, 1H), 3.58 (br d, J=11.4 Hz, 2H), 3.40 (M, 2H), 2.50 (m, 1H), 2.34 (d, J=11.6 Hz, 1H). APCI MS m/e 210.9 [(M+1)$^+$]; M.p. 260° C. (dec.); Anal. Calcd. for C$_{14}$H$_{14}$N$_2$.2HCl: C, 59.38; H, 5.69; N, 9.89. Found C, 59.69; H, 5.82; N, 9.79.

Example 57

6-METHYL-5,14-DIAZATETRACYCLO [10.3.1.0$^{2,11}$.0$^{4,9}$]HEXADECA-2(11),3,5,7,9-PENTAENE HYDROCHLORIDE

A) 1-((6-Methyl-5,14-diazatetracyclo [10.3.1.0$^{2,11}$.0$^{4,9}$]hexadeca-2(11),3,5,7,9-pentaen-10-yl)-2,2,2-trifluoro-ethanone Following the method described in Example 56A, 1-(4-Amino-10-aza-tricyclo[6.3.1.0$^{2,7}$]dodeca-2(7),3,5-trien-10-yl)-2,2,2-trifluoro-ethanone (686 mg, 2.00 mmol) was reacted with (E)-2-butenal (0.2 mL, 2.97 mmol) to provide a yellow oil. (335.6 mg, 52%). (TLC 75% ethyl acetate/hexanes R$_f$ 0.25).

B) 6-Methyl-5,14-diazatetracyclo[10.3.1.0$^{2,11}$.0$^{4,9}$] hexadeca-2(11),3,5,7,9-pentaene hydrochloride 1-(6-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone (308 mg, 0.96 mmol) was converted to the title compound using methods described in Example 17 to provide a crystalline solid (186 mg). $^1$H NMR (400 MHz, CD$_3$OD) δ 9.00 (d, J=8.5 Hz, 1H), 8.25 (s, 1H), 8.17 (s, 1H), 7.94 (d, J=8.5 Hz, 1H), 3.76 (br s, 1H), 3.71 (br s, 1H), 3.57 (br d, J=11.8 Hz, 2H), 3.38 (M, 2H), 3.01 (s, 3H), 2.49 (m, 1H), 2.32 (d, J=11.6 Hz, 1H). APCI MS m/e 225.2 [(M+1)$^+$]; M.p. >300° C. (dec.); Anal. Calcd. for C$_{15}$H$_{16}$N$_2$.2HCl.½H$_2$O: C, 58.83; H, 6.25; N, 9.15. Found C, 58.49; H, 6.22; N, 9.02.

Example 58

7-METHYL-5,14-DIAZATETRACYCLO [10.3.1.0$^{2,11}$.0$^{4,9}$]HEXADECA-2(11),3,5,7,9-PENTAENE HYDROCHLORIDE

A) 1-(7-Methyl-5,14-diazatetracyclo [10.3.1.0$^{2,11}$.0$^{4,9}$]hexadeca-2(11),3,5,7,9-pentaen-10-yl)-2,2,2-trifluoro-ethanone Following the method described in Example 56A, 1-(4-Amino-10-aza-tricyclo[6.3.1.0$^{2,7}$]dodeca-2(7),3,5-trien-10-yl)-2,2,2-trifluoro-ethanone (686 mg, 2.00 mmol) was reacted with 2-methylpropenal (0.25 mL, 3.00 mmol) to provide a yellow oil (94 mg, 15%). (TLC 10% methanol/CH$_2$Cl$_2$ R$_f$ 0.16).

B) 7-Methyl-5,14-diazatetracyclo[10.3.1.0$^{2,11}$.0$^{4,9}$] hexadeca-2(11),3,5,7,9-pentaene hydrochloride 1-(7-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone (86 mg, 0.27 mmol) was converted to the title compound using methods described in Example 17 to provide a crystalline solid (12.6 mg). $^1$H NMR (400 MHz, CD$_3$OD) δ 9.10 (s, 1H), 9.00 (s, 1H), 8.22 (s, 1H), 8.20 (s, 1H), 3.76 (br s, 1H), 3.72 (br s, 1H), 3.57 (br d, J=11.5 Hz, 2H), 3.39 (M, 2H), 2.71 (s, 3H), 2.48 (m, 1H), 2.32 (d, J=11.6 Hz, 1H). APCI MS m/e 225.0 [(M+1)$^+$].

Example 59

7-ETHYL-5,14-DIAZATETRACYCLO [10.3.1.0$^{2,11}$.0$^{4,9}$]HEXADECA-2(11),3,5,7,9-PENTAENE HYDROCHLORIDE

A) 1-(7-Ethyl-5,14-diazatetracyclo[10.3.1.0$^{2,11}$.0$^{4,9}$] hexadeca-2(11),3,5,7,9-pentaen-10-yl)-2,2,2-trifluoro-ethanone Following the method described in Example 56A, 1-(4-Amino-10-aza-tricyclo[6.3.1.0$^{2,7}$]dodeca-2(7),3,5-trien-10-yl)-2,2,2-trifluoro-ethanone (686 mg, 2.00 mmol) was reacted with 2-ethylpropenal (0.35 mL, 3.60 mmol) to provide a yellow oil (110 mg, 16%). (TLC 75% ethyl acetate/hexanes R$_f$ 0.32).

B) 7-Ethyl-5,14-diazatetracyclo[10.3.1.0$^{2,11}$.0$^{4,9}$] hexadeca-2(11),3,5,7,9-pentaene hydrochloride 1-(7-Ethyl-5,14-diazatetracyclo[10.3.1.0$^{2,11}$.0$^{4,9}$]hexadeca-2(11),3,5,7,9-pentaen-10-yl)-2,2,2-trifluoro-ethanone (94 mg, 0.28 mmol) was converted to the title compound using methods described in Example 17 to provide a crystalline solid (33 mg). $^1$H NMR (400 MHz, CD$_3$OD) δ 9.12 (s, 1H), 9.00 (s, 1H), 8.23 (s, 1H), 8.18 (s, 1H), 3.76 (br s, 1H), 3.72 (br s, 1H), 3.56 (br d, J=11.5 Hz, 2H), 3.37 (M, 2H), 3.05 (q, J=7.5 Hz, 2H), 2.48 (m, 1H), 2.32 (d, J=11.6 Hz, 1H), 1.44 (t, J=7.5 Hz, 3H). APCI MS m/e 239.1 [(M+1)$^+$]; M.p. 288–291° C. (dec.); Anal. Calcd. for C$_{16}$H$_{18}$N$_2$.2HCl.H$_2$O: C, 58.36; H, 6.73; N, 8.51. Found C, 57.98; H, 5.99; N, 8.41.

Example 60a

8-METHYL-5,14-DIAZATETRACYCLO [10.3.1.0$^{2,11}$.0$^{4,9}$]HEXADECA-2(11),3,5,7,9-PENTAENE HYDROCHLORIDE

A) 1-(8-Methyl-5,14-diazatetracyclo [10.3.1.0$^{2,11}$.0$^{4,9}$]hexadeca-2(11),3,5,7,9-pentaen-10-yl)-2,2,2-trifluoro-ethanone Following the method described in Example 56A, 1-(4-Amino-10-aza-tricyclo[6.3.1.0$^{2,7}$]dodeca-2(7),3,5-trien-10-yl)-2,2,2-trifluoro-ethanone (775 mg, 2.52 mmol) was reacted with 1-buten-3-one (0.32 mL, 3.79 mmol) to provide a yellow oil. (424 mg, 52%). (TLC 50% ethyl acetate/hexanes R$_f$ 0.08).

B) 8-Methyl-5,14-diazatetracyclo[10.3.1.0$^{2,11}$.0$^{4,9}$]hexadeca-2(11),3,5,7,9-pentaene hydrochloride 1-(8-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone (403 mg, 1.26 mmol) was converted to the title compound using methods described in Example 17 to provide a crystalline solid (266 mg). $^1$H NMR (400 MHz, CD$_3$OD) δ 9.01 (d, J=5.6 Hz, 1H), 8.49 (s, 1H), 8.22 (s, 1H), 7.97 (d, J=5.6 Hz, 1H), 3.76 (br m, 2H), 3.58 (br d, J=11.5 Hz, 2H), 3.40 (m, 2H), 3.06 (s, 3H), 2.48 (m, 1H), 2.33 (d, J=11.6 Hz, 1H). Anal. Calcd. for C$_{15}$H$_{16}$N$_2$.2HCl.H$_2$O: C, 57.15; H, 6.39; N, 8.89. Found C, 57.43; H, 6.44; N, 8.82.

Example 60b 5,14-DIAZATETRACYCLO[10.3.1.0$^{2,11}$.0$^{4,9}$]HEXADECA-2(11),3,7,9-TETRAEN-6-ONE HYDROCHLORIDE A) 3,3-Dimethoxypropanoic acid lithium Salt (Related to methods described in Alabaster, C. T. et al., *J. Med. Chem.* 1988, 31, 2048–2056.) 3,3-Dimethoxypropanoic acid methyl ester (14.25 g, 96.2 mmol) in THF (100 mL) was treated with LiOH.H$_2$O (2.5 g, 106 mmol) and H$_2$O (2 mL). The mixture was brought to reflux for 4 hours, cooled to room temperature and azeotropically dried from THF (4 times) to provide white solids (13.3 g).

B) 1-(4-(N-3',3'-Dimethoxy-propionamide)-10-azatricyclo[6.3.1.0$^{2,7}$]dodeca-2(7),3,5-trien-10-yl)-2,2,2-trifluoro-ethanone 3,3-Dimethoxypropanoic acid lithium salt (840 mg, 6.0 mmol) in THF (15 mL) was treated with trifluoroacetic anhydride (0.85 mL, 6.0 mmol) dropwise and stirred for 15 minutes. The resulting yellow solution was added dropwise to a vigorously stirred mixture of 1-(4-amino-10-aza-tricyclo[6.3.1.0$^{2,7}$]dodeca-2(7),3,5-trien-10-yl)-2,2,2-trifluoro-ethanone (540 mg, 2 mmol) in THF (5 mL) and saturated aqueous NaHCO$_3$ solution (2 mL). After 3 hours the reaction mixture was diluted with H$_2$O and extracted with ethyl acetate (3 times). The organic layer was washed with brine, dried over Na$_2$SO$_4$, filtered and concentrated to an oil which was purified by chromatography on Silica gel to provide a white solid (477 mg, 62%). (TLC 50% ethyl acetate/hexanes R$_f$ 0.37).

C) 1-(5,14-Diazatetracyclo[10.3.1.0$^{2,11}$.0$^{4,9}$]hexadeca-2(11),3,7,9-tetraen-6-one-10-yl)-2,2,2-trifluoro-ethanone 1-(4-(N-3',3'-Dimethoxy-propionamide)-10-aza-tricyclo[6.3.1.0$^{2,7}$]dodeca-2(7),3,5-trien-10-yl)-2,2,2-trifluoro-ethanone (460 mg, 1.19 mmol) was treated with trifluoroacetic acid (4 mL) and stirred 18 hours, concentrated, diluted with CH$_2$Cl$_2$ and H$_2$O. The aqueous layer was extracted with CH$_2$Cl$_2$ (4 times) and the organic layer was washed with saturated aqueous NaHCO$_3$ solution (40 mL) and saturated aqueous NaCl solution then dried through a cotton plug. Concentration afforded a yellow solid (320 mg, 83%).

D) 5,14-Diazatetracyclo[10.3.1.0$^{2,11}$.0$^{4,9}$]hexadeca-2(11),3,7,9-tetraen-6-one hydrochloride 1-(5,14-Diazatetracyclo[10.3.1.0$^{2,11}$.0$^{4,9}$]hexadeca-2(11),3,7,9-tetraen-6-one-10-yl)-2,2,2-trifluoro-ethanone (540 mg, 2 mmol) was converted to the title compound using methods described in Example 17 to provide the title compound a pink crystalline solid (72 mg, 71%). $^1$H NMR (400 MHz, CD$_3$OD) δ 8.42 (d, J=8.8 Hz, 1H), 7.90 (s, 1H), 7.66 (s, 1H), 6.98 (d, J=8.8 Hz, 1H), 3.59 (br s, 1H), 3.56 (br s, 1H), 3.49 (dd, J=12.4, 5.8 Hz, 2H), 3.29 (m, 2H), 2.42 (m, 1H), 2.23 (d, J=11.6 Hz, 1H). APCI MS m/e 227 [(M+1)$^+$]; M.p. 300° C. (dec.); Anal. Calcd. for C$_{14}$H$_{14}$N$_2$O.2HCl: C, 56.20; H, 5.39; N, 9.36. Found C, 56.40; H, 5.63; N, 9.25.

Example 61

6-CHLORO-5,14-DIAZATETRACYCLO[10.3.1.0$^{2,11}$.0$^{4,9}$]-HEXADECA-2(11),3,5,7,9-PENTAENE HYDROCHLORIDE

A) 1-(6-Chloro-5,14-diazatetracyclo[10.3.1.0$^{2,11}$.0$^{4,9}$]hexadeca-2(11),3,5,7,9-pentaen-10-yl)-2,2,2-trifluoro-ethanone 1-(5,14-diazatetracyclo[10.3.1.0$^{2,11}$.0$^{4,9}$]hexadeca-2(11),3,7,9-tetraen-6-one-10-yl)-2,2,2-trifluoro-ethanone (156 mg, 0.49 mmol) was treated with POCl$_3$ (5 mL) and warmed to 100° C. with stirring for 3 hours. After concentration in vacuo, the residue was diluted with CH$_2$Cl$_2$ (15 mL) and carefully treated with saturated NaHCO$_3$ solution (10 mL) with stirring. Once CO$_2$ evolution slowed the mixture was separated and the aqueous layer extracted CH$_2$Cl$_2$ (3 times). The organic layer was washed with H$_2$O and saturated NaCl solution, filtered through cotton and concentrated to a brown oil (217 mg, 93%). (TLC ethyl acetate, R$_f$ 0.3) $^1$H NMR (400 MHz, $^2$HCCl$_3$) δ 8.03 (d, J=8.5 Hz, 1H), 7.83 (s, 1H), 7.62 (s, 1H), 7.35 (d, J=8.5 Hz, 1H), 4.43 (m, 1H), 4.01 (m, 1H), 3.62 (m, 1H), 3.29 (m, 2H), 3.23 (m, 1H), 2.45 (m, 1H), 2.10 (d, J=11.6 Hz, 1H). APCI MS m/e 341.1 [(M+1)$^+$].

B) 6-Chloro-5,14-diazatetracyclo[10.3.1.0$^{2,11}$.0$^{4,9}$]hexadeca-2(11),3,5,7,9-pentaene hydrochloride 1-(6-Chloro-5,14-diazatetracyclo[10.3.1.0$^{2,11}$.0$^{4,9}$]hexadeca-2(11),3,5,7,9-pentaen-10-yl)-2,2,2-trifluoro-ethanone (26 mg, 0.076 mmol) was converted to the title compound using methods described in Example 17 to provide the title compound a solid (5.8 mg, 24%). $^1$H NMR (free base, 400 MHz, $^2$HCCl$_3$) δ 8.01 (d, J=8.5 Hz, 1H), 7.77 (s, 1H), 7.57 (s, 1H), 7.30 (d, J=8.5 Hz, 1H), 3.28 (br s, 1H), 3.24 (br s, 1H), 3.12 (br d, J=12.5 Hz, 2H), 2.96 (br d, J=12.5 Hz, 2H), 2.41 (m, 1H), 2.02 (d, J=11.6 Hz, 1H). APCI MS m/e 245.1 [(M+1)$^+$].

Example 62

6-METHOXY-5,14-DIAZATETRACYCLO[10.3.1.0$^{2,11}$.0$^{4,9}$]HEXADECA-2(11),3,5,7,9-PENTAENE HYDROCHLORIDE

A) 6-Chloro-5,14-diazatetracyclo[10.3.1.0$^{2,11}$.0$^{4,9}$]hexadeca-2(11),3,5,7,9-pentaen-10-carboxylic acid tert-butyl ester 6-Chloro-5,14-diazatetracyclo[10.3.1.0$^{2,11}$.0$^{4,9}$]hexadeca-2(11),3,5,7,9-pentaene (2.82 g, 11.53 mmol) was converted into the title compound as described in Example 22A to provide a brown oil (3.55 g, 89%). (TLC: 5% methanol/CH$_2$Cl$_2$, R$_f$ 0.37).

B) 6-Methoxy-5,14-diazatetracyclo[10.3.1.0$^{2,11}$.0$^{4,9}$] hexadeca-2(11),3,5,7,9-pentaen-10-carboxylic acid tert-butyl ester Sodium metal (~12 mg) was dissolved in methanol (1 mL) under nitrogen with stirring and treated with a solution of 6-chloro-5,14-diazatetracyclo[10.3.1.0$^{2,11}$.0$^{4,9}$]hexadeca-2(11),3,5,7,9-pentaen-10-carboxylic acid tert-butyl ester (118 mg, 0.33 mmol) in methanol (3 mL) and brought to reflux for 18 hours. The mixture was cooled, concentrated, treated with H$_2$O and extracted with CH$_2$Cl$_2$. The organic layer was washed with saturated NaCl solution and filtered through a cotton plug then concentrated to an oil (165 mg). (TLC: 5% methanol/CH$_2$Cl$_2$ R$_f$ 0.55).

C) 6-Methoxy-5,14-diazatetracyclo[10.3.1.0$^{2,11}$.0$^{4,9}$] hexadeca-2(11),3,5,7,9-pentaene hydrochloride 6-Methoxy-5,14-diazatetracyclo[10.3.1.0$^{2,11}$.0$^{4,9}$]hexadeca-2(11),3,5,7,9-pentaen-10-carboxylic acid tert-butyl ester (138 mg, 0.41 mmol) was dissolved in trifluoroacetic acid (4 mL) brought to reflux for 4 hours. The mixture was cooled and concentrated to an oil which was dissolved in ethyl acetate and treated with 3N HCl/ethyl acetate (1 mL). After concentration the residue was recrystallized from methanol/diethyl ether to provide a beige solid (51 mg, 26%). $^1$H NMR (400 MHz, CD$_3$OD) δ 8.77 (d, J=9.5 Hz, 1H), 8.01 (s, 1H), 7.90 (s, 1H), 7.54 (d, J=9.5 Hz, 1H), 4.30 (s, 3H), 3.65 (br s, 1H), 3.61 (br s, 1H), 3.50 (dd, J=12.4, 3.8 Hz, 2H), 3.29 (m, 2H), 2.44 (m, 1H), 2.24 (d, J=11.6 Hz, 1H). APCI MS m/e 241.2 [(M+1)$^+$]; M.p. 240, (darkens), 275° C. (dec.); (TLC: 10% methanol (NH$_3$)/CH$_2$Cl$_2$, R$_f$ 0.38).

Example 63

5,8,14-TRIAZATETRACYCLO[10.3.1.0$^{2,11}$.0$^{4,9}$] HEXADECA-2(11),3,7,9-TETRAEN-6-ONE HYDROCHLORIDE

A) 1-(5,8,14-Triazatetracyclo[10.3.1.0$^{2,11}$.0$^{4,9}$]hexadeca-2(11),3,7,9-tetraen-6-on-10-yl)-2,2,2-trifluoroethanone 1-(4,5-Diamino-10-aza-tricyclo[6.3.1.0$^{2,7}$]dodeca-2(7),3,5-trien-10-yl)-2,2,2-trifluoro-ethanone (536 mg, 1.88 mmol) was stirred in ethanol (4 ml). This mixture was treated with methyl-2-hydroxyl-2-methoxy acetate (0.203 mL, 2.07 mmol) and stirred at 70° C. for 2.5 hours. The reaction was cooled to room temperature and concentrated. Trituration with methanol and filtration provided light yellow solids (337 mg, 55%). (TLC 10% methanol/CH$_2$Cl$_2$ R$_f$ 0.57).

B) 5,8,14-Triazatetracyclo[10.3.1.0$^{2,11}$.0$^{4,9}$]hexadeca-2(11),3,7,9-tetraen-6-one hydrochloride 1-(5,8,14-Triazatetracyclo[10.3.1.0$^{2,11}$.0$^{4,9}$]hexadeca-2(11),3,7,9-tetraen-6-on-10-yl)-2,2,2-trifluoro-ethanone (145 mg, 0.45 mmol) was converted to the title compound by the methods described in Example 17C to provide a brown solid (26 mg, 46%). $^1$H NMR (400 MHz, D$_2$O) δ 7.94 (s, 1H), 7.58 (s, 1H), 7.18 (s, 1H), 3.39 (br s, 2H), 3.28 (br d, J=12.5 Hz, 1H), 3.12 (br d, J=12.5 Hz, 1H), 2.29 (m, 1H), 1.99 (d, J=12.0 Hz, 1H). APCI MS m/e 228.2 [(M+1)$^+$]; M.p. 296, (darkens), 310° C. (dec.); (TLC: 10% CH$_2$Cl$_2$/methanol (NH$_3$), R$_f$ 0.10).

What is claimed is:

1. A process for the preparation of any one of the compounds of formulae (Ia) and (Ib) or a mixture thereof:

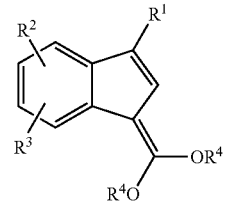

(Ia)

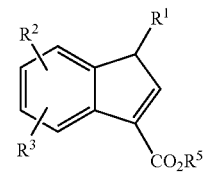

(Ib)

wherein R$^2$ and R$^3$ are independently selected from the group consisting of hydrogen, fluoro, —CF$_3$, and —OCH$_3$;

R$^1$ is an electron withdrawing group selected from cyano and phenylsulfonyl;

each R$^5$ for formula (Ia) is independently hydrogen, methyl, ethyl, or a metal cation Na$^+$, with the proviso that only one R$^5$ can be methyl or ethyl;

R$^5$ of formula (Ib) is methyl or ethyl;

comprising the step of reacting a compound of formula (III)

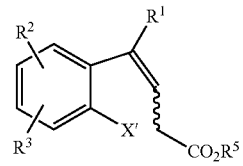

(III)

wherein R$^1$, R$^2$, R$^3$, and R$^5$ are as set forth above; and X' is bromo or chloro, in the presence of a palladium catalyst and a base.

2. A process according to claim 1 wherein R$^2$ and R$^3$ are hydrogen; R$^1$ is CN; and X' is bromo.

3. A process according to claim 1 wherein the palladium catalyst is formed from the combination of a palladium compound selected from the group consisting of palladium (II) acetate, palladium(II) chloride, bis-acetonitrile palladium(II) chloride, bis-benzonitrile palladium(II) chloride, palladium(II) bromide, and tris(dibenzylideneacetone)dipalladium(0); and a phosphine ligand selected from the group consisting of dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)-biphenyl, and 2-dicyclohexylphosphino-2'-(N,N-dimethylamino)biphenyl.

4. A process according to claim 1 wherein the base selected from sodium tert-butoxide, potassium tert-butoxide, sodium tert-pentoxide, sodium ethoxide, sodium carbonate, potassium carbonate, cesium carbonate, sodium hydride, lithium hydride and potassium hydride.

5. A process according to claim 1 further comprising the prior step of reacting a compound of formula (IV):

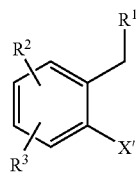
(IV)

wherein $R^1$ is an electron withdrawing group selected from cyano and phenylsulfonyl; X' is bromo or chloro; with a compound of formula (V):

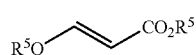
(V)

wherein $R^5$ is methyl or ethyl; in the presence of a base, resulting in the formation of the compound of formula III:

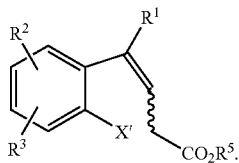
(III)

6. A processes according to claim 5 wherein $R^1$ is CN; $R^2$ and $R^3$ are hydrogen; and X' is bromo.

7. A process according to claim 5 wherein the base is selected from sodium tert-butoxide, potassium tert-butoxide, sodium methoxide, sodium ethoxide, sodium tert-pentoxide, sodium carbonate, potassium carbonate, cesium carbonate, lithium diisopropylamide, lithium bis(trimethylsilyl)amide, sodium bis(trimethylsilyl)amide, potassium bis(trimethylsilyl)amide, sodium hydride, and lithium hydride.

8. A process for the preparation of any one of compounds of the formulae (Ia) and (Ib) or a mixture thereof:

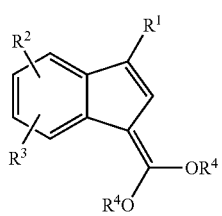
(Ia)

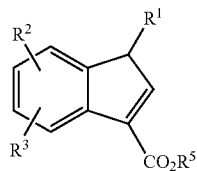
(Ib)

wherein $R^2$ and $R^3$ are independently selected from the group consisting of hydrogen, fluoro, —$CF_3$, and —$OCH_3$;

$R^1$ is an electron withdrawing group selected from cyano and phenylsulfonyl;

each $R^5$ for formula (Ia) is independently hydrogen, methyl, ethyl, or a metal cation $Na^+$, with the proviso that only one $R^5$ can be methyl or ethyl; or two R5 together form a ($C_2$–$C_3$)alkylene bridge;

$R^5$ of formula (Ib) is methyl or ethyl;

comprising the step of reacting a compound of formula (IV)

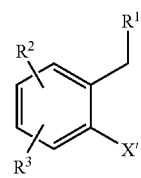
(IV)

wherein $R^1$ is an electron withdrawing group selected from cyano and phenylsulfonyl; X' is bromo or chloro; with a compound of formula (V):

wherein $R^1$ is methyl or ethyl; in the presence of a base and a palladium catalyst; and further followed by neutralization in the presence of a diol alcohol when the two $R^5$ groups of formula (Ia) is a ($C_2$–$C_3$)alkylene bridge.

9. A processes according to claim 8 wherein $R^1$ is CN; $R^2$ and $R^3$ are hydrogen; and X' is bromo.

10. A process according to claim 8 wherein the base is selected from the group consisting of sodium tert-butoxide, potassium tert-butoxide, sodium methoxide, sodium ethoxide, sodium tert-pentoxide, sodium carbonate, potassium carbonate, cesium carbonate, lithium diisopropylamide, lithium bis(trimethylsilyl)amide, sodium bis(trimethylsilyl)amide, potassium bis(trimethylsilyl)amide, sodium hydride, and lithium hydride.

11. A process according to claim 8 wherein the palladium catalyst is prepared by the addition of a palladium compound selected from palladium(II) acetate, palladium(II) chloride, bis-acetonitrile palladium(II) chloride, bis-benzonitrile palladium(II) chloride, palladium(II) bromide, and tris(dibenzylideneacetone)dipalladium(0); and a phosphine ligand selected from the group consisting of dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)biphenyl, and 2-dicyclohexylphosphino-2'-(N,N-dimethylamino)biphenyl.

12. A process for the preparation of compounds of formula (VII):

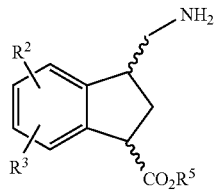

comprising the step of subjecting any one of compounds of the formulae (Ia) and (Ib) or a mixture thereof:

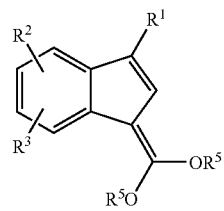

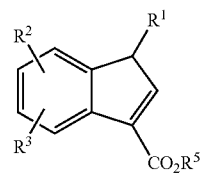

to hydrogenolysis conditions;
wherein $R^1$ is CN or phenylsulfonyl; $R^2$ and $^3$ are independently selected from the group consisting of hydrogen, fluoro, —$CF_3$, and —$OCH_3$;
$R^5$ of formula (Ib) is methyl or ethyl;
each $R^5$ for formula (Ia) is independently hydrogen, methyl, ethyl, or a metal cation $Na^+$, with the proviso that only one $R^5$ can be methyl or ethyl.

13. A process according to claim 12 wherein $R^1$ is CN; and $R^2$ and $R^3$ are hydrogen.

14. A process according to claim 12 wherein the hydrogenolysis conditions comprise a hydrogenation catalyst selected from palladium on carbon, palladium hydroxide on carbon, platinum on carbon, platinum oxide, and platinum oxide on carbon; in the presence of an acid selected from sulfuric acid, hydrochloric acid, methane sulfonic acid, toluenesulfonic acid, trifluoroacetic acid, acetic acid, formic acid, phosphoric acid and perchloric acid.

15. A process according to claim 12 wherein the hydrogenolysis conditions comprise a hydrogenation catalyst selected from 5% palladium on carbon, 10% palladium on carbon and 5% platinum on carbon; in the presence of sulfuric acid, methane sulfonic acid, or a mixture of these two acids.

16. A process according to claim 12 wherein the single hydrogenation step is replaced by the two separate steps of (a) subjecting any one of compounds of the formulae (Ia)' and (Ib)':

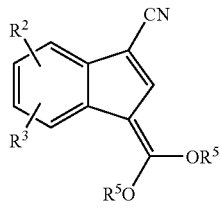

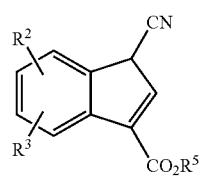

or mixtures thereof wherein $R^2$ and $R^3$ are hydrogen;
$R^5$ of formula (Ib) is methyl or ethyl;
each $R^5$ for formula (Ia) is independently hydrogen, methyl, ethyl, or a metal cation $Na^+$, with the proviso that only one $R^5$ can be methyl or ethyl;
to hydrogenation conditions to obtain a compound of formula (IX)':

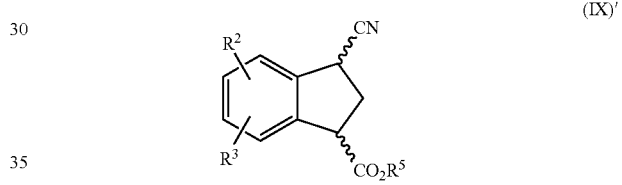

wherein $R^2$, $R^3$, and $R^5$ are as defined above; (b) and then reducing the compound of formula (IX)' to obtain a compound of formula (VII)':

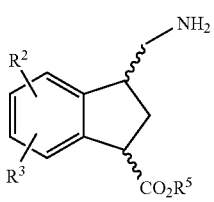

wherein $R^2$, $R^3$, and $R^5$ are as defined above.

17. A process according to claim 16 wherein the hydrogenation conditions in step (a) for the reduction of the compounds of formulae (Ia)' and (Ib)' to one of formula (IX)' comprise treatment with a hydrogenation catalyst selected from the group consisting of palladium on carbon, palladium hydroxide on carbon, platinum on carbon, platinum oxide, and platinum oxide on carbon; in the presence of an acid selected from the group consisting of acetic acid, formic acid, benzoic acid, and salicylic acid.

18. A process according to claim 16 wherein the hydrogenation conditions in step (a) comprise treatment with a hydrogenolysis catalyst that is either 5% palladium on carbon, 10% palladium on carbon or 5% platinum on carbon; in the presence of either formic acid or acetic acid.

19. A process according to claim 16 wherein the reduction conditions in step (b) for reducing the nitrile compound of formula (IX)' to one of formula (VII)' comprise treatment with a hydrogenation catalyst selected from the group consisting of palladium on carbon, palladium hydroxide on carbon, platinum on carbon, platinum oxide, and platinum oxide on carbon; in the presence of an acid selected from sulfuric acid, hydrochloric acid, methane sulfonic acid, toluenesulfonic acid, trifluoroacetic acid, acetic acid, formic acid, phosphoric acid and perchloric acid.

20. A process according to claim 16 wherein the reduction conditions in step (b) comprise treatment with a hydrogenation catalyst that is 5% palladium on carbon, 10% palladium on carbon or 5% platinum on carbon; in the presence of any of sulfuric acid, methane sulfonic acid, or a combination thereof.

n

* * * * *